(12) United States Patent
Anderson

(10) Patent No.: US 7,713,440 B2
(45) Date of Patent: May 11, 2010

(54) STABILIZED UNCOATED PARTICLES OF REVERSED LIQUID CRYSTALLINE PHASE MATERIALS

(75) Inventor: David Anderson, Ashland, VA (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 1528 days.

(21) Appl. No.: 10/889,313

(22) Filed: Jul. 13, 2004

(65) Prior Publication Data

US 2005/0077497 A1    Apr. 14, 2005

Related U.S. Application Data

(60) Provisional application No. 60/509,255, filed on Oct. 8, 2003.

(51) Int. Cl.
*C11D 1/00*    (2006.01)
(52) U.S. Cl. .................. 252/299.1; 424/489
(58) Field of Classification Search ............. 424/1.21, 424/402, 422, 426, 450, 489; 435/7; 514/254; 252/299; *A61K 9/50; B01J 13/00, 13/02*
See application file for complete search history.

(56) References Cited

U.S. PATENT DOCUMENTS

| 5,531,925 A | 7/1996 | Landh et al. |
| 6,197,349 B1 * | 3/2001 | Westesen et al. ............ 424/501 |

FOREIGN PATENT DOCUMENTS

| WO | WO 84/02076 | * | 6/1984 |
| WO | WO 93/09621 | * | 4/1993 |
| WO | WO 99/12640 | * | 3/1999 |

OTHER PUBLICATIONS

Handbook of Pharmaceutical Excipients, American Pharmaceutical Association (1986), p. 207-208 (Poloxamer).*
Alexandridis et al., A Record Nine Different Phases (Four Cubic, Two Hexagonal, and One Lamellar Lyotropic Liquid Crystalline and Two Micellar Solutions) in a Ternary Isothermal System of an Amphiphilic Block Copolymer and Selective Solvents (Water and Oil), Langmuir (1998) 14, 2627-2638.*
Drummond et al., Surfactant self-assembly objects as novel drug delivery vehicles, Current Opinion in Colloid & Interface Science 4 (2000) 449-456.*
Engstrom et al., Cubic phases for studies of drug partition into lipid bilayers, European Journal of Pharmaceutical Sciences 8 (1999) 243-254.*
The Merck Index, 14th Edition ver. 14.4. Copyright © 2006, 2009 by Merck & Co., Inc., Whitehouse Station, New Jersey, USA.*
Wikipedia, The Free Encyclopedia, http://en.wikipedia.org/w/index.php?title=Zeta_potential&printable=yes Sep. 18, 2009.*
"Zeta Potential of Colloids in Water and Waste Water", ASTM Standard D 4187-82, American Society for Testing and Materials, 1983.*

* cited by examiner

*Primary Examiner*—Yvonne L Eyler
*Assistant Examiner*—Suzanne Ziska
(74) *Attorney, Agent, or Firm*—Whitham Curtis Christofferson & Cook, PC

(57) ABSTRACT

A pharmaceutical composition comprises uncoated particles of a single thermodynamic equilibrium reversed cubic phase material containing an active agent disposed within. The uncoated particles have an anionic charge that is sufficient to stabilize them in dispersion in a liquid, e.g. a polar solvent.

29 Claims, 16 Drawing Sheets

STABILIZED UNCOATED PARTICLES OF REVERSED LIQUID CRYSTALLINE PHASE MATERIALS

CROSS REFERENCE TO RELATED APPLICATIONS

This application is claims priority to U.S. Provisional Patent Application 60/509,255 filed Oct. 8, 2003, and the complete contents are herein incorporated by reference.

BACKGROUND OF THE INVENTION

1. Field of the Invention

The invention generally relates to uncoated particles of reversed cubic phase or reversed hexagonal phase material containing an active. In particular, the invention provides uncoated particles having an ionic charge that is sufficient to stabilize the particles in dispersion in a liquid, e.g. a polar solvent.

2. Background of the Invention

Many active compounds used in pharmaceutical, nutritional, nutriceutical, environmental, and industrial uses are either insoluble in water, or perform better when delivered in some sort of protective, targetable, and/or otherwise functional matrix. In the case of pharmaceuticals, it is generally recognized that microparticles can provide robust matrices for drugs by various routes of administration, provided they are of appropriate size, stable in dispersion, and composed of excipients that are acceptable for that route. However, in addition to solubilizing and/or protecting the active compound for administration and/or in circulation, it would be advantageous for a microparticle to play an active role in the delivery and absorption of the active, a goal that has been a stumbling block for a number of potentially useful particulate and droplet-based vehicles.

For the case of pharmaceutical actives that are of low solubility in water, solubilization of such drug compounds is made challenging by the very limited selection of solvents and structured liquids that are approved by regulatory bodies for use at levels that would be required to solubilize the drug. Furthermore, water-miscible liquid excipients, most notably ethanol, are of limited value since, even when the drug is soluble in neat ethanol, for example, it will often precipitate upon contact with water, such as with either diluent water for injection or in the aqueous milieu of body fluids, such as blood.

Nanostructured lyotropic liquid crystalline phases of the reversed type—namely reversed cubic and reversed hexagonal phases—have been developed as excellent solubilizing matrices for both poorly-soluble compounds, and for such delicate compounds as proteins and other biomacromolecules. U.S. Pat. No. 6,482,517 (Anderson, Nov. 19, 2002) and U.S. Pat. No. 6,638,621 (Anderson, Oct. 28, 2003), the contents of which are incorporated in their entireties by reference, disclose, among other things, effective compositions and methods for producing such lyotropic liquid crystalline matrices. These particles are coated with solid materials.

A pioneer in surfactant phase behavior, P. A. Winsor, described particles of cubic phase coated with a nanostructured liquid phase, which in accordance with current knowledge was probably an L3 phase. See *Liquid Crystals & Plastic Crystals*, Vol. 1, eds. G. W. Gray and P. A. Winsor (1974), Ellis Horwood Ltd., page 224, as well as Balinov, Olsson and Soderman (1991) *J. Phys. Chem.* 95:5931. Larsson, in 1989, described reversed cubic phase particles with lamellar liquid crystalline phase coatings. See Larsson (1989) *J. Phys. Chem.* 93(21) 7304.

U.S. Pat. No. 5,531,925 (Landh et al., Jul. 2, 1996) likewise describes particles of reversed cubic or reversed hexagonal phase which require a surface phase of either lamellar liquid crystalline, lamellar crystalline, or L3 phase, in order to disperse the particles. The coating is referred to in that disclosure as a "surface phase", or "dispersible phase", thereby teaching, first, that it is a distinct, separate phase from the reversed liquid crystalline interior, and second, that the reversed liquid crystalline phase interior is itself not a dispersible phase. The L3 surface phase in that disclosure is described as being "anchored to the bi- or mono-layer of the interior phase" (column 7, lines 59-60).

U.S. Pat. No. 6,071,524 describes compositions in the form of dispersions containing: (a) 60 to 98% by weight of an aqueous phase and (b) 2 to 40% by weight of an oily phase dispersed in the aqueous phase, the oily phase being dispersed and stabilized by using cubic gel particles. The particles are essentially formed of 0.1 to 15% by weight (relative to the total weight of the composition) of at least one unsaturated fatty acid monoglyceride having a C16-C22 unsaturated fatty chain in a mixture with phytanetriol, and 0.05 to 3% by weight relative to the total weight of the composition of a dispersing and stabilizing agent. The agent is a surface active substance, water-soluble at room temperature, containing a linear or branched, saturated or unsaturated, fatty chain having 8 to 22 carbon atoms. The patent also describes methods of making such compositions. A minimum of three thermodynamically distinct phases are present in such a mixture, namely the aqueous exterior phase, the cubic gel particles, and the oil phase containing the active. The active substance (drug, cosmeceutical compound, etc.) is present in the dispersed oily phase, and in fact substantially localized in the oily phase. Such systems, emulsions in which lipid or surfactant monolayers, multilayers, lamellar or non-lamellar liquid crystalline domains or lamellar crystalline domains stabilize droplets of one fluid in another, suffer from poor suitability for targeting, shelf-life limitations (creaming, breaking of emulsions, etc.), and other problems well known in the art of emulsions. And emulsions or droplet systems in which each droplet is surrounded by a plurality of particles of another material or phase, all undergoing independent diffusion around the droplet (and, by definition, are separated from one another by intervening fluid layers), suffer from gaps between the particles that compromise the ability of the material to control the egress of active out of, or ingress of confounding factors into, the droplet. Furthermore, with such a system wherein the plurality of particles surrounding the droplet are derived from lyotropic liquid crystals, as in U.S. Pat. No. 6,071,524, in the body of an animal these particles can readily become independent of the droplets, such that the droplets, which contain the vast majority of the active, do not reap the potential benefits (as discussed herein) of the liquid crystalline particles. Although the "cubic gel particles" of U.S. Pat. No. 6,071,524 are designed to aggregate at the surface of the oil droplets, in a pharmaceutical application the high dilution factors and shear forces, together with the myriad of biochemical conditions and processes encountered by a droplet, could readily strip the droplets of their intended coating. Another limitation of the invention described in U.S. Pat. No. 6,071,524 is that neither the monoglycerides nor the phytanetriol (nor many of the other surfactants used in the reported embodiments) is approved for use in injectable pharmaceutical products, and indeed monoglycerides are known to be extremely toxic upon injection.

U.S. application 2002/0153509 (Lynch et al, published Oct. 24, 2002) describes compositions in which charged compounds are used as "anchors" ("tethers"), serving to anchor active compounds or targeting compounds to cubic phases, sometimes in particulate form. For example, it is stated in the disclosure of 2002/0153509 that the inclusion of an anchor such as a cationic surfactant could increase the amount of active drug in the cubic phase in proportion to the amount of surfactant (e.g., paragraph 0099), in accordance with the schematic picture shown in FIG. 2 of that disclosure which depicts an anionic ketoprofen molecule associated with the head group of a cationic surfactant (and situated on the polar side of the polar-apolar interface). The anchor's purpose is to bind a drug molecule, on a 1-to-1 molecule basis.

It would be desirable to have improved microparticles for drug solubilization and protection that are of an appropriate size, stable in dispersion, and composed of excipients that are acceptable for administration via a variety of routes. In addition, it would be desirable to have improved microparticles that also play an active role in the delivery and absorption of the drug.

SUMMARY OF THE INVENTION

As discussed in more detail herein, particles of reversed lyotropic liquid crystalline phase materials can exhibit high potential to transport active compounds across a variety of barriers such as cell membranes, particularly in the case of the reversed bicontinuous cubic phases, by virtue of their unique nanoporous structures and associated curvature properties. The reversed cubic and reversed hexagonal liquid crystalline phases can be of very low solubility in water, meaning that they maintain their integrity as vehicles upon entry into the body thus avoiding drug precipitation. Thus, with superior solubilizing and sequestration properties, as well as integrity in water, these materials show a great deal of promise in fields such drug delivery. However, this potential has remained largely untapped due to the tacit assumption that such particles must be coated in order to be stable in dispersion.

In the present invention, the full potential of this transport activity can be tapped within the context of stable particle dispersions, first through the realization that uncoated particles of such phases are highly desirable for their transport and absorption-enhancing properties, and second through the realization that ionically charged, bilayer-associated compounds with appropriate chemistries and concentrations can stabilize such particles as uncoated particles by creating strong electrostatic surface potentials-particle zeta potentials. In particular, it is taught herein that zeta potential is a key parameter for establishing such stabilization, and that a zeta potential of greater than or equal to about 25 mV, or more preferably greater than about 30 mV, in magnitude is an important requirement for such a system. Likewise, a zeta potential of less than −25 mV or less than −30 mV in magnitude is useful for stabilization.

The invention thus provides stable, uncoated particles formed of reversed lyotropic liquid crystalline materials, e.g. reversed cubic or reversed hexagonal liquid crystalline material. The particles are "uncoated" in that the liquid crystalline material of which the particles are formed is in direct contact with the medium in which the particles are dispersed, i.e. the outer periphery of an individual, dispersed particle is not shielded from the medium (for example, an aqueous liquid phase) in which the particles are dispersed. No coating intervenes between the particle and the medium, or between a particle and other particles. Rather, the particles are repelled from one another and are held in dispersion in the medium by strong electrostatic surface potentials. Such strong electrostatic surface potentials are created by proper choice of the "ingredients" which are combined to make up the liquid crystalline material of which the particles are formed, as taught herein. In general, the ratio by weight of particle to liquid phase medium is in the range of between about 1:2 to about 1:1000. The particle size is between about 10 nanometers (the order of magnitude of a single unit cell of reversed liquid crystalline material) and 100 microns, preferably between about 40 nm and 10 microns, and most preferably (at least for injectable products) submicron, meaning less than one micron in effective diameter. Particles that can be passed through a 0.22 micron filter, or extruded similarly, are especially preferred since this sterilizes the product.

In some embodiments of the invention, an active compound, typically though not always a pharmaceutical compound, is dissolved or dispersed or otherwise incorporated within the liquid crystalline phase material itself. Preferably, in this embodiment, the active compound and the liquid crystalline material form an intimately-associated, integrated unit, i.e. the active compound is part of the liquid crystal. One advantage of such a particle is that the active compound reaps the benefit of the absorption-promoting capabilities of the liquid crystal, in a manner that is superior to particle configurations described elsewhere, where the active is present primarily outside the liquid crystal, or inside a liquid crystal particle that is covered with an interfering coating. Indeed, it is envisioned that in many cases, the majority of actives will remain associated with the liquid crystal up to the point where the liquid crystal integrates with, for example, a targeted cell membrane, thereby eliminating the need for the active to dissolve in an aqueous biological fluid (e.g., blood, intestinal fluid) en route to cellular uptake. If the particle is taken up by endocytosis, then the same ability to fuse with biomembranes could play a key role in circumventing a limitation that applies to liposomes, namely that of entrapment inside endosomal compartments and resulting poor delivery to the intracellular site(s). It is also of major impact herein that this can all be accomplished within the context, and extreme restrictions, of injectable formulations including intravenous pharmaceutical formulations.

In another embodiment of the invention, the active agent or compound is not part of the liquid crystalline material that forms the uncoated particle, but is either a liquid that is embedded within the uncoated particle, or is solubilized in a liquid that is embedded, dissolved, dispersed or otherwise incorporated within the uncoated particle. In yet another embodiment, the active agent is dispersed inside the uncoated particle in the form of microcrystals of the compound.

Thus, it is an object of this invention to provide administrable active-loaded microparticles that take full advantage of the absorption-promoting and drug-solubilizing potential of reversed cubic and reversed hexagonal liquid crystalline phase microparticles, undiminished by effects of coatings.

It is an object of this invention to provide administrable active-loaded microparticles that exhibit direct, unhindered interactions with biomembranes which can strongly promote absorption and/or allow targeting.

It is another object of this invention to provide stable dispersions of such active-loaded lyotropic liquid crystalline microparticles for injection.

It is another object of this invention to provide design criteria and compositions that will yield stabilized particle dispersions of reversed liquid crystalline phase material.

It is another object of this invention to provide experimental criteria and procedures by which to determine whether a particular composition will yield stabilized particle dispersions of reversed liquid crystalline phase material.

It is another object of this invention to provide compositions with the necessary physicochemical properties to yield sufficient surface charge stabilization.

It is another object of the invention to provide methods for stabilizing uncoated particles of reversed liquid crystalline phase materials.

It is another object of this invention to provide a method for treating a mammal with a pharmaceutical or nutriceutical active compound by administering a dispersion of uncoated particles of reversed liquid crystalline phase material.

It is another object of this invention to provide nanocrystal drug formulations in which the stabilizing matrix can serve the additional functions of enhancing drug absorption and solubilizing other useful excipients for intimate association with the drug.

It is another object of this invention to provide compositions that yield charge-stabilized particles and dispersions thereof upon reconstitution with water.

Further, it is an important object of this invention to provide new compositions and methods for the delivery of cancer therapeutic agents, local anesthetic and general anesthetic agents, and anesthetic reversal agents. These include in particular propofol, alphaxalone, alfatalone, alphadolone, eltanolone, propanidid, ketamine, pregnanolone, etomidate, and other general anesthetics; bupivacaine, lidocaine, procaine, tetracaine, mepivacaine, etidocaine, oxybuprocaine, cocaine, benzocaine, pramixinine, prilocaine, proparacaine, ropivicaines, chloroprocaine, dibucaine and related local anesthetics; SN-38 and related camptothecins; paclitaxel and related taxanes; doxorubicin, idarubicin, daunorubicin and related rubicins; amphotericin B; coenzyme Q10; steroids and steroidal anti-inflammatory agents; nonsteroidal anti-inflammatories (e.g., salicylates, para-aminophenol derivatives (e.g., acetaminophen), fenomates, proprionic acid derivatives (e.g., naproxen, ibuprofen, etc.); analgesics; antipyretics; sedatives (e.g., benzodiazepines such as diazepam); hypnotics (e.g., intravenous anesthetics and barbiturates); opiates; cannabinoids; and proteins (e.g., insulin and erythropoietin)(it being understood that a wide variety of amides and esters may have application in the present invention). Of particular importance is the general anesthetic agent propofol, which is supplied in formulations that suffer from problems of burning on injection, microbial contamination, and high lipid loads.

DETAILED DESCRIPTION OF THE PREFERRED EMBODIMENTS OF THE INVENTION

Figure 1:
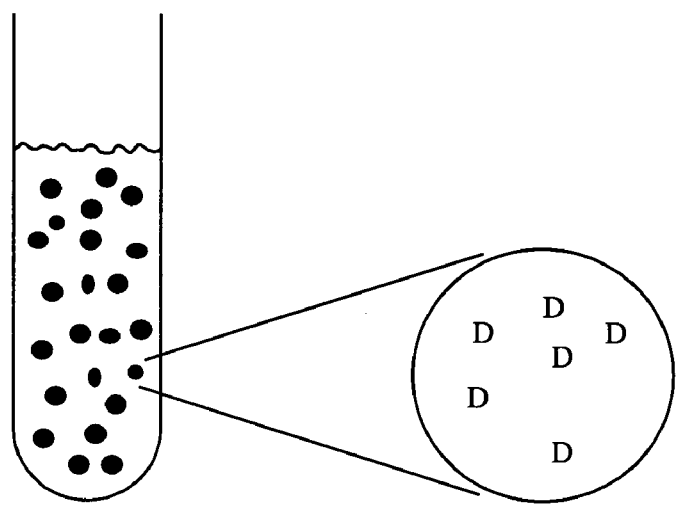
FIG. 1 shows a schematic of a dispersion according to the present invention.

The inventor has demonstrated the relationship between curvature properties of lipids, and their tendency to promote porosity in bilayers and to form reversed cubic and other reversed phases. See Anderson D. M., Wennerstrom, H. and Olsson, U., *J. Phys. Chem.* 1989, 93:4532-4542. To summarize a crucial aspect of this, if one assumes a mathematical model in which the bilayer thickness is constant, and that the bilayer midplane is twice differentiable, one can show first that, in order to minimize unfavorable curvature energies, the midplane must have zero mean curvature throughout. Next, under these conditions one can then show that if the average mean curvature at the polar-apolar interface is toward water—as it is in a reversed liquid crystalline phase—then the integral Gaussian curvature is significantly negative. Negative integral Gaussian curvature then implies porosity in the bilayer system. A conclusion of the full analysis drawn by the inventor is that, if a composition which assembles into a porous bilayer phase, such as a reversed cubic phase, begins to exchange material with a membrane, such as a biomembrane, it can induce a local tendency for reversed curvature (curvature toward water at the polar-apolar interface), and thereby induce porosity in the biomembrane. This can be of great importance in the delivery of drugs across biomembrane barriers to absorption, constituting an inherent advantage of a reversed cubic or reversed hexagonal phase over a lamellar or liposomal material in the practice of drug delivery, particularly in the delivery of anticancer drugs and other drugs where absorption barriers are very significant problems in therapeutic treatment.

In view of this relationship, the tendency to induce or form porous microstructures is viewed in the present context as being advantageous with respect to drug- and nutrient-delivery in particular, as well as in other applications, in that it promotes the integration of administered lipid-based (or surfactant-based) microparticles with biomembranes that otherwise form barriers to absorption. This is in sharp contrast with lamellar lipidic structures such as liposomes which show low curvature, and little or no porosity, and do not ordinarily show strong tendencies to integrate with biomembranes. One very important aspect of this is that it can also allow cubic phase materials to overcome efflux proteins such as P-glycoprotein (P-gp). The inventor recognizes it is crucial to provide for as intimate contact as possible between the reversed liquid crystalline phase material and any biological (or other) barriers inherent in the application of the invention. Examples of such barriers which are of particular interest as barriers that can be overcome by the present invention include: plasma membranes of cells that are sites of drug action; the blood-brain barrier; apical membranes of intestinal epithelial cells; macrophage membranes; neuronal cell membranes; intracellular membranes such as the mitochondrial membrane or the nuclear membrane; and buccal or nasal mucosal cell membranes.

However, while a number of methods have been developed for formulating microparticles of reversed liquid crystalline phases, the inclusion of a stabilizing coating phase has led to the development of particles with attenuated absorption-promoting properties, since the interactions with biomembranes are then affected by the properties of the coating, rather than the reversed liquid crystalline phase itself. Thus, while such coatings often serve a useful function, in some cases the coating may be undesirable.

In this invention, drug-loaded microparticles of reversed cubic and reversed hexagonal liquid crystalline phases are dispersed in a liquid such as water, without any coating, thus permitting direct interactions between the liquid crystal and biological barriers. In addition, this can be achieved using only components that are pharmaceutically-acceptable for injection, including intravenous injection, a necessary requirement for the use of such dispersions in certain critical drug-delivery applications. This is achieved in the present invention by compositions containing ionically charged, bilayer-associated components that yield an electrostatic potential on the particles sufficiently strong to stabilize the particle dispersions against aggregation, flocculation, and fusion; as a rule this requires a zeta potential greater than or equal to about 25 mV in magnitude, or more preferably greater than about 30 mV in magnitude. The invention thus represents a fundamental departure from particles, and teachings, of the prior art based on reversed liquid crystalline phases with a coating, i.e. in which an additional phase on the exterior of the particle stabilizes dispersions of such particles.

U.S. Pat. No. 5,531,925 provides an example of the tacit assumption to previous teachings that a coating a) is required to stabilize liquid crystalline particles, and b) does not interfere with particle function. The particles described in U.S. Pat. No. 5,531,925 are coated with surface phases comprising L3 phases and lamellar liquid crystalline phases or lamellar crystalline phases which are inherent obstructions to function. These surface phases, in close analogy with liposomes based on lamellar liquid crystalline and lamellar crystalline phases, suffer from a number of drawbacks and limitations, most notably unfavorable interactions with biomembranes that limit their ability to deliver their payload to cells. Indeed, not only do these intervening surface phases impede the entry of the vehicle into the target cell, but in addition, after entry—which typically requires endocytosis—the particle is entrapped in an endosome representing yet another barrier to delivery. Such limitations are well known in the field of liposome-based drug-delivery. They are particularly limiting in the case of injectable drug formulations, where barriers to vehicle uptake by the target cell increase the likelihood that the vehicle is taken up by unfavorable or even toxicity-eliciting alternative mechanism, such as by the liver or the immune system.

In the case of coatings consisting of L3 surface phases, the tendency for the L3 phase to exhibit only very limited absorption-favoring interactions with biomembranes is probably due to its highly dynamic structure, and/or its ability, and tendency, to very rapidly reorganize into a lamellar or lamellar-like structure, correlating with its observed shear-birefringence, the presence of a splitting in pulsed-NMR bandshape measurements, and its transformation into a lamellar phase over time (see U.S. Pat. No. 5,531,925 column 7 lines 3748 and column 15 lines 5-36). Indeed, the "lubricating" effect of the L3 phases, which is apparently what makes them effective as "dispersible phases" in the methods of U.S. Pat. No. 5,531,925, can be described as inducing a tendency for L3-coated particles coming in near-contact to avoid fusion, due in part to the fluctuating, thermally-roiled nature of the liquid L3 phase producing an effective repulsive force of considerable strength. The same repulsion appears to apply to particles coming in near-contact with the walls of a container, correlating with a lack of adhesion and "slippery" flow noted by Landh with his dispersions of L3-coated particles. By extension, it would follow that L3-coated particles should by their very nature experience a strong fluctuation-induced repulsive force when approaching a biomembrane, and thus suffer limitations that have plagued liposome technology, particularly in regard to cell entry and lack of absorption promotion. The long-circulating nature of the L3-coated particles, reported in the example of intravenous somatostatin in rabbits of U.S. Pat. No. 5,531,925 supports the notion that these particles do not tend to interact intimately with biomembranes, but rather stay in circulation by avoiding integration with membranes.

Contributing further to this fluctuation-induced force (which in the study of closely-related lamellar phases is referred to as the "undulation force", well studied by W. Helfrich) are hydration-induced forces arising from the highly hydrated L3 phase. The L3 phase quite generally exists at high water contents, nearly always at higher water contents than any cubic phase(s) that is (are) close in composition space; Landh and Larsson note in fact that when an L3 phase and cubic phase are in equilibrium, that the characteristic dimensions of the L3 phase are approximately twice those of the cubic phase, and this corresponds to considerably higher water content, a conclusion that is additionally made obvious by the phase diagram itself where the water content in the L3 phase is higher than that of the cubic phase. It is well known in the art that heavily hydrated surfaces experience a considerable repulsive force upon approaching a biomembrane. The highly polyoxyethlyated (PEGylated), high-HLB surfactants that are present in large weight-fraction proportions in the L3 phases of the reported embodiments in U.S. Pat. No. 5,531,925 are known to be very heavily hydrated at ambient or body temperatures. In the instant invention, in the case where the particles are stabilized by a negative zeta potential, this will give rise to a repulsive force upon near-contact with a typical biomembrane, but due to the low magnitude of the zeta potential of a typically biomembrane, the force will be weak in comparison with the combined fluctuation and hydration-induced forces in the L3-coated particle case. In cases of the current invention where a positive zeta potential stabilizes the particles, this will give rise to an attractive force. Hydration forces in the case of particles of the current invention can be kept weak, as evidenced by the low water contents of the reversed liquid crystalline phases even when the charged, bilayer-associated compound is incorporated directly into the liquid crystalline phase, as shown in several of the cases reported in the Examples section below.

The presence of another phase coating the surface of the aforementioned particles can not only intervene and interrupt potentially favorable interactions between the liquid crystal and biomembrane barriers to absorption, but can also create numerous practical and experimental problems. Interpretation of in vivo performance and elucidation of the mechanism of action of the formulation is of course complicated by the presence of a coating, which can be of considerable impact in the development and application of an injectable pharmaceutical formulation. In the case of L3 phase coatings, even the existence of the L3 phase is difficult experimentally to validate, much less characterize, as indicated for instance in lines 29-33 of column 15 of U.S. Pat. No. 5,531,925; furthermore, as indicated on lines 41-45 of column 7, the L3 phase is often metastable, and this can give rise to pharmaceutically-unacceptable changes in structure over time, as proven in publications dealing with particles of Landh and Larsson. See Gustafsson, Ljusberg-Wahren, Almgren and Larsson (1996), Langmuir, 12(20):4611. In addition, in the case of particles of the U.S. Pat. No. 5,531,925 patent, compositions yielding such particles are limited to those lying in 3-phase regions of the phase diagram where the interior, coating, and exterior aqueous phase are in thermodynamic equilibrium. Such 3-phase regions are often difficult to find experimentally and are typically sensitive to material purity and other intensive variables.

Another valuable aspect of the current invention over such coated particles as those of U.S. Pat. No. 5,531,925 is the fact that the reversed liquid crystalline phase is the only lipid-based matrix in the particle and thus the only location available within the particle for an active compound, in contrast with particles coated by another lipid-based (or surfactant-based) phase, particularly an L3 phase. When a second phase, the coating phase, is also available for the active, a degree of control is lost and this can compromise or even negate the effect of one or more of the features that made the reversed liquid crystalline phase the matrix of choice in the first place. For example, if the controlled poresize of the reversed liquid crystalline phase is being used to control either the efflux of a large-molecule active out of the liquid crystal, or the penetration of an adsorbing (e.g., albumin) or degrading protein (e.g., protease, nuclease, glycosidase), then this is compromised if a significant fraction of the active is present in the coating phase; the effective poresize of the L3 phase coating is known to be larger than that of the interior phase by a factor of two, typically. It is important to note in such an instance that in general, components of these liquid crystalline phases including the active diffuse around within the particle, so that the active will be located in the coating phase a certain fraction of the time, and during these periods it may be susceptible to attack.

FIG. 1 shows a schematic of a dispersion of uncoated particles according to the present invention. The letters "D" indicate that drug (or more generally, active) is present in the reversed cubic phase or reversed hexagonal liquid crystalline phase particle. In the most preferred embodiment, the drug or active D is a component of the reversed cubic phase or reversed hexagonal phase. In alternative embodiments, the drug or active D is dissolved or dispersed or embedded or otherwise incorporated within the particle. In one variation, the drug or active D may be incorporated in an oil phase that is positioned within the particle.

Figure 2:
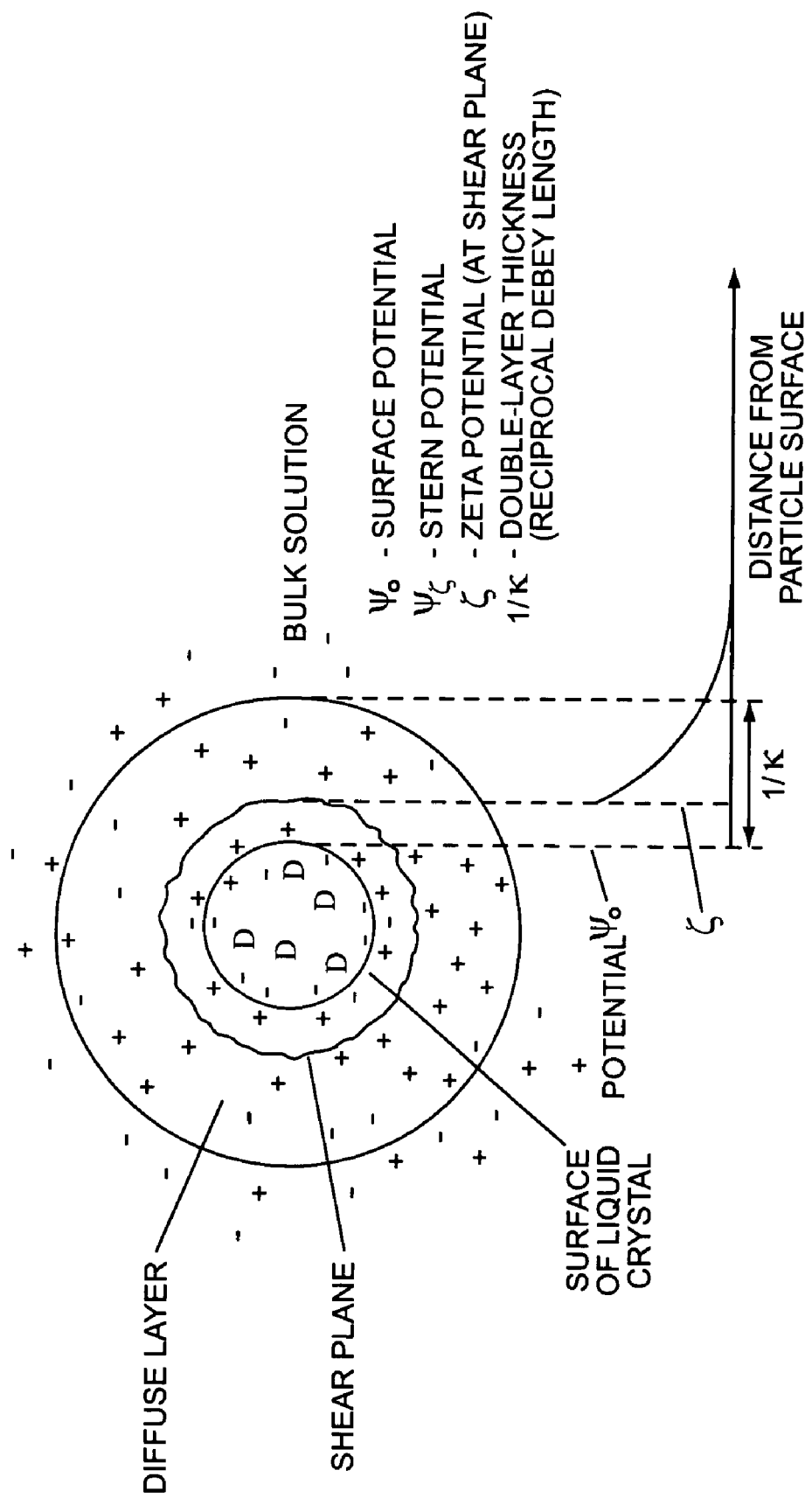
FIG. 2 shows a schematic of the electrostatic situation in a representative particle of the instant invention, with a net negative surface charge.

FIG. 2 shows a schematic of the electrostatic configuration in a representative uncoated particle of the instant invention, with a net negative surface ionic charge. The "+" signs represent cationic moieties and the "−" signs represent anionic moieties, which in this case would include the charged, bilayer-associated compounds utilized in the invention. As one moves away from the (anionically-charged) surface of the particle, the preponderance of negative charges diminishes. The zeta potential measurement measures the potential due to the excess of ionic charges (in this case, anionic) at the shear plane, which is displaced from the particle surface. Nevertheless, at least in the conditions used in the Examples below and quite broadly in the practice of this invention, the shear plane still lies within the Debye layer, which is at a distance (the Debye length) from the particle surface where there is no longer a net excess of anions.

The following definitions will be helpful.

Uncoated particle: As used herein, an uncoated particle of reversed cubic (or hexagonal) phase is a particle in which the outermost material phase of the particle is a reversed cubic (or hexagonal) phase, so that there is no other phase present exterior to and in contact with this outermost material phase except for a single liquid (usually aqueous) phase in which the particles are dispersed (dispersion phase), and wherein the material of this reversed cubic [hexagonal] phase is a single, contiguous and isolated mass of material thus defining a single particle. In this definition "isolated" means substantially not in contact with other such particles except for the normal particle-particle collisions in the course of Brownian motion.

The uncoated particle thus defined contrasts with U.S. Pat. No. 6,482,517 in which there is a crystalline coating exterior to the liquid crystalline phase, and also in contrast with U.S. Pat. No. 5,531,925 and the work of P. A. Winsor cited above in which there is a distinct L3 phase, lamellar phase, or crystalline lamellar phase exterior to (i.e. coating) the reversed liquid crystalline phase. As discussed herein, the L3 and lamellar coatings in particular are antithetical to the purpose of employing the particles in permeability enhancement for improved drug delivery, and they may furthermore introduce other limitations and practical problems.

It should be noted that this definition does not preclude the possibility that, at a scale which is small compared to the thickness of the outermost material phase (usually the radius of the particle, unless for example an oil-core is present as per U.S. application Ser. No. 10/176,112, which is herein incorporated by reference, or the particle contains an embedded crystal), the nanoscale appearance at the surface of the outermost material phase does not represent the typical appearance in the bulk of that material phase, because of surface reordering or related effects, provided there is no extraneous phase present exterior to the liquid crystalline phase in the sense of the Gibbs Phase Rule. As is well known in the art, surface energies can induce reordering at the surface of a material that can change the microscopic appearance, as for example a hemispherical end-cap covering what would be a pore opening at the end of a cylinder in the reversed hexagonal phase. However, this does not indicate the presence of another phase, in the strict thermodynamic sense of a phase. To illustrate, at a given temperature and pressure, by the Gibbs Phase Rule a two-component lipid/water mixture can only exhibit two phases at equilibrium, and while the surface of a portion or particle of reversed hexagonal phase could show a nanoscale-thickness region that is rich in hemispherical end-caps, with polar groups of the lipid in contact with an exterior water-rich phase (the second phase of the two present), this region does not constitute a third phase. (Although the term "interphase" has been used to describe such regions, even users of that term will agree that it does not represent a distinct thermodynamic phase as governed by the Phase Rule; rather, an interface, or interfacial zone, describes the surface of the outermost material phase). In general, the thickness of this surface-reordered region will be about equal to or less than the unit cell lattice parameter, in the case of reversed hexagonal phase and reversed cubic phase materials. Thus, in particular, the thickness of such a surface-reordered region (or "interphase") will generally be less than about 30 nm, and usually less than about 20 nm.

In the case of the solid-coated particles revealed in U.S. Pat. No. 6,482,517 where the interior phase is a reversed cubic or reversed hexagonal phase, it will be obvious to anyone skilled in the art that the material constituting the solid coating is a distinct phase from the liquid crystalline interior.

Polar, Apolar, Amphiphile, Surfactant, Polar-apolar interface, Bicontinuous: The terms "polar", "apolar", "amphiphile", "surfactant", "polar-apolar interface", and "bicontinuous" as used herein are taken to have the meaning given in U.S. Pat. No. 6,638,621, the complete contents of which is incorporated herein by reference.

Bilayer-associated, membrane-associated: A compound or moiety is bilayer-associated if it partitions preferentially into a bilayer over an aqueous compartment. Thus, if a bilayer-rich material such as a reversed cubic phase material exists in equilibrium with excess water and is placed in contact with excess water, and a bilayer-associated compound or moiety is allowed to equilibrate between the two phases, then the overwhelming majority of the compound or moiety will be located in the bilayer-rich phase. The concentration of the compound or moiety in the bilayer-rich phase will be at least about 100 times, and preferably at least about 1,000 times, larger than in the water phase.

It is important to note that although the reversed hexagonal phases and reversed discrete or discontinuous cubic phases do not have a true bilayer as the fundamental structural unit, in the present disclosure we will nevertheless use the term "bilayer-associated" to describe components that partition into the lipid-rich (or surfactant-rich) microdomains irrespective of whether such domains are considered "monolayers" or "bilayers". The term "bilayer-associated" is thus more directed to the partitioning of the compound in question than to the precise nature of the lipid (or surfactant) region.

Besides targeting and bilayer-charging compounds, another component of the particle that can be bilayer-associated is the drug (or more generally, active) itself. For small molecules, this is preferred, since it means that the drug will tend to remain with the particle even when the particle is exposed to large volumes of biological fluids. However, drugs that partition preferentially into the aqueous channels of the reversed liquid crystalline material, including many if not most proteins and other biomacromolecules, can be incorporated into particles of the current invention, as can drugs that localize to comparable concentrations in the aqueous and hydrophobic compartments. Indeed, one important aspect of the invention which distinguishes it over typical emulsions, for example, is the very large polar-apolar surface areas, which provide ample volume for drugs which have apolar groups or epitopes that prefer a hydrophobic milieu as well as polar groups that prefer the hydrophilic milieu of the aqueous channels and head group-rich regions.

Hydrophobe-rich droplet; hydrophobe-rich phase: In some embodiments of the instant invention, the reversed liquid crystalline phase material will contain, in its interior, a droplet of a hydrophobe-rich phase that is distinct from the reversed liquid crystalline phase; this is not to be confused with hydrophobic domains that are structural elements of the reversed liquid crystalline phase itself. This hydrophobe-rich droplet will be of size between about 20 nm and 100 microns, that will contain as a major component a hydrophobe, thus a component of low solubility in water (less than about 3%), and/or of high octanol-water partition coefficient (Kow greater than or equal to about 10, more preferably greater than about 100), in which are solubilized the active and some fraction (perhaps very small) of each of the components of the second volume.

Thus, while thermodynamics dictates that this first volume must contain at least a trace of lipid and the second volume at least a trace of the hydrophobic liquid, the defining feature of the first volume chemistry is that the ratio of hydrophobic liquid to lipid is significantly higher than in the second volume. The solubility of a given active in a mixture of hydrophobe and lipid is typically a very strongly increasing function of an increasing hydrophobe:lipid ratio, because the hydrophobe can generally be chosen specifically for its ability to solubilize the particular active whereas the choice of lipid has much more to do with its ability to form liquid crystals (in the presence of the hydrophobe, in particular). For example, whereas the solubility of the drug paclitaxel in eugenol is over 15% by weight, its solubility in a mixture of 42% egg phosphatidylcholine, 35% eugenol, and 23% water is less than 1.5%; thus the addition of phospholipid and water to the paclitaxel-in-eugenol solution induces precipitation of the paclitaxel. The presence of the first volume can thus dramatically increase the overall solubility of the active in the particle, and can yield a substantial and pharmaceutically appropriate concentration of active in cases where the solubility of active in a lipid-rich liquid crystalline phase (in the absence of the first volume) would be prohibitively low, that is, in cases where an therapeutic amount of drug could not be solubilized in a pharmaceutically acceptable amount of liquid crystal. These requirements can be phrased in terms of phase behavior as follows. There must exist a liquid crystalline phase in equilibrium with a liquid phase which is rich in a hydrophobic liquid that solubilizes the active. Furthermore, preferably there should exist a three-phase equilibrium with these two phases in equilibrium with a polar solvent-rich phase, which is usually a water-rich phase, often over 90% water.

This liquid phase will be hydrophobe-continuous, which is the generalization of the term of art "oil-continuous" to the case where the hydrophobe can be quite different chemically from what is commonly referred to as an "oil". Thermodynamically, this liquid phase can be a reversed micellar solution, a surfactant solution (whether dilute or otherwise, bearing in mind that every surfactant will have some non-zero solubility even if it is vanishingly small), an oil-rich microemulsion, or an L3 phase (of the type referred to as L3*, in publications where L3 and L3* are distinguished). These phases are well known in the art, and are discussed in detail in U.S. Pat. No. 6,482,517.

Pharmaceutically-acceptable: In the context of this invention, "pharmaceutically-acceptable" generally designates compounds or compositions in which each excipient is approved by the Food and Drug Administration, or a similar body in another country, for use in a pharmaceutical formulation, or belongs to a succinct class of compounds for which a Drug Master File is on file with a government regulatory agency, usually the FDA. This also includes compounds that are major components of approved excipients, which are known to be of low toxicity taken internally. A listing of approved excipients, each with the various routes of administration for which they are approved, was published by the Division of Drug Information Resources of the FDA in January, 1996 and entitled "Inactive Ingredient Guide". The existence of a Drug Master File at the FDA is additional evidence that a given excipient is acceptable for pharmaceutical use, at least for certain routes of administration. For injectable products, a listing of approved excipients was published in 1997. See Nema, Washkuhn and Brendel (1997) PDA *J. of Pharm. Sci. & Technol.* 51(4):166. It should be added that there are certain compounds, such as vitamins and amino acids, which are in injectable products (typically for parenteral nutrition) as "actives", and are thus known to be safe upon injection, and such compounds are considered herein as pharmaceutically-acceptable as excipients as well, for injection. A particularly important example of a succinct class of compounds where a Drug Master File (DMF) is on file is the class of Pluronic (Poloxamer) surfactants, for which BASF has a DMF on file. In this case, although only a few members of this class have explicitly been used in injectable formulations, for the purposes of this invention, the homogeneity of the class, the presence of a DMF, and the existence of approved-for-injection formulations using several members of the class is sufficient to include each of the members of the class of Pluronics as pharmaceutically-acceptable for injectable products.

Stabilized particle. For the purposes of this disclosure, for brevity the term "stabilized particle" will mean a particle that can, in plurality, form a stable dispersion in a liquid, preferably a liquid comprising a polar solvent, and most preferably comprising water or glycerol. A stable dispersion means that the particle dispersion does not show detrimental effects from flocculation or fusion over time scales of at least several days, preferably several weeks and most preferably over several months.

Target, target cell: In some cases these terms will have slightly different meanings in this disclosure as often used in the art. By "target" we mean the cell, or other moiety, to which the active must be delivered by the particle in order to be absorbed or otherwise made available-whether or not that corresponds to the ultimate site of action of the active. For example, if a drug is delivered perorally within particles of the invention, the target would typically be an absorptive intestinal epithelial cell, no matter what the site of action of the drug after systemic absorption. If the particle accomplishes the task of getting the active absorbed at the target site, then it has been successful in its pharmaceutical task.

Targeting moiety, targeting compound: In this disclosure, this term will have a meaning that is quite distinct from that of "target" or "target cell" as defined above. A targeting moiety is a chemical group that is part of the particle of the instant invention, situated either inside the liquid crystal or bound to the surface of the particle, and serves as a molecular target for some compound outside the particle in the application, typically though not always a biomolecule in the body of a mammal. A targeting compound, then, is a compound that contains a targeting moiety. It is important to point out that the targeting moiety is incorporated in the current invention without the introduction of another phase at the surface of the particle. In other words, as discussed elsewhere herein, the number of thermodynamic phases is not increased. An example of a targeting moiety would be an antibody that is attached to the particle, for example by a covalent bonding to a flexible spacer that is lipid-anchored into the particle, such that the antibody contains a targeting moiety that will bind to a biological molecule (the antigen) in the body and thus locate the particle at the desired site of action. In this case, the targeting moiety may be thought of as either a binding motif on the antibody, or the entire antibody itself.

Dissolution: By the term "dissolution" is meant that a compound under consideration is dissolving, or is "undergoing dissolution".

Solubilize: This term is meant to be essentially synonymous with the term "dissolve" or "dissolution", though with a different connotation. A compound under consideration is solubilized in a liquid or liquid crystalline material if and only if the molecules of the compound are able to diffuse within the liquid or liquid crystalline material as individual molecules, and that such material with the compound in it make up a single thermodynamic phase. It should be borne in mind that slightly different connotations are associated with the terms "dissolve" and "solubilize". Typically the term "dissolve" is used to describe the simple act of putting a crystalline compound in a liquid or liquid crystalline material and allowing or encouraging that compound to break up and dissolve in the material, whereas the terms "solubilize" and "solubilization" generally refer to a concerted effort to find an appropriate liquid or liquid crystalline material that is capable of dissolving such compound.

Chemical criteria: A number of criteria have been tabulated and discussed in detail by Robert Laughlin for determining whether a given polar group is functional as a surfactant head group, where the definition of surfactant includes the formation in water of nanostructured phases even at rather low concentrations. R. Laughlin, Advances in Liquid Crystals, pp. 341, 1978. A further discussion and listings of topics including: polar groups which are not operative as surfactant head groups; polar groups which are operative as surfactant head groups; apolar group; and single-component block copolymers; see U.S. Pat. No. 6,638,621, the complete contents of which is hereby incorporated by reference.

Reversed liquid crystalline phases, including reversed hexagonal phase and reversed cubic phase (the latter of which includes both reversed bicontinuous cubic phase and reversed discrete cubic phase) are understood to be as described in detail elsewhere (e.g. in U.S. Pat. No. 6,638,621, the complete contents of which is herein incorporated by reference). These phases are known in the art of surfactant self-association.

Methods and Materials

In this invention, the process typically begins with the selection of a liquid crystal composition that preferably solubilizes, or otherwise entraps (e.g., incorporates) the active, and has the appropriate physicochemical characteristics for the desired interactions as described herein. An active may be described as "entrapped" by the liquid crystal composition if, for example, the active is solubilized in an oil droplet that is ultimately located within the particle, or if the active is in crystalline form, and the crystals are ultimately dispersed throughout the particle. Compositions for reversed liquid crystalline phases are discussed at length in U.S. Pat. No. 6,482,517 the contents of which are incorporated herein by reference, and in U.S. patent application Ser. Nos. 09/994,937 and 10/460,659, which are herein incorporated by reference. As will be discussed in greater detail below, in the most preferred form, the active forms a component of the reversed cubic or reversed hexagonal phase.

An important consideration in the selection of a liquid crystal composition, which may not be obvious to those schooled in the traditional art, is that the composition chosen for the liquid crystal must be robust enough—in particular, must have a high enough melting point, the best single measure of this characteristic—that it can accommodate the incorporation of a charged, bilayer-associated component such as an ionic surfactant. Such components often (though not universally) have the effect of melting materials such as reversed cubic phases. When a reversed cubic phase melts, e.g., by the addition of a charged bilayer-associated component, it will usually melt into either an L2 phase, or an L3 phase, both of which suffer from limited interactions with biological barriers, as described herein.

Exceptions to the general rule that high loadings (greater than about 8%, or especially greater than 15%) of a charged surfactant usually melt the reversed liquid crystalline phases most often occur when the surfactant has two (or more) long hydrophobic chains (greater than or equal to 12 carbons each) and a polar head group of relatively low MW, in particular MW<300, particularly if the hydrophobic chains are saturated alkane chains. Thus, a double-chained surfactant such as didodecyldimethylammonium bromide will not typically cause the melting of a reversed liquid crystalline phase material, nor will a charged phospholipid molecule particularly if it is saturated. Those double-chained phospholipids which are sufficiently strongly charged for this application include phosphatidylglycerol, phosphatidylserine, phosphatidylinositol, and phosphatidic acid, but not phosphatidylcholine or phosphatidylethanolamine.

After, or concomitantly with, the selection of liquid crystal composition, one or more appropriate ionically-charged, bilayer-associated components is/are selected based on such properties as partition coefficient (generally high is best, preferably greater than about 1,000), low toxicity, favorable regulatory status (dependent on the route of administration), and solubility and compatibility with the other components of the formulation. A selection of such components is given herein.

In the course of this work it was established that once the zeta potential of a collection of these reversed liquid crystalline phase particles equals or exceeds about 25 millivolts in magnitude (that is, more positive than 25 mV or more negative than −25 mV), or preferably greater than about 30 mV in magnitude (or more negative than −30 mV), then no other mechanism is required for stabilization of the dispersion against flocculation. In some cases, other exceptional attractive forces, such as intermingling of surface-associated polymer chains, unusual ionic conditions, time-dependent redistributions within the particles, may prevent the formation of stabilized particles by this method alone.

It is generally agreed in the art that differences in zeta potentials are not significant unless they differ by approximately 5 mV or more. Phrased otherwise, with little loss of information, zeta potentials can be reported as multiples of 5 mV. Thus, the rule that 30 mV (positive or negative) or greater is sufficient for charge-stabilization will be phrased, for the purposes of this disclosure, as the criterion that a zeta potential greater than about 25 mV in magnitude is what the invention calls for as a surface charge, with a value greater than about 30 mV being especially preferred.

It is important to optimize the ratio of charged surfactant to liquid crystal, when charge-stabilizing liquid crystalline particles for injection. Eliminating or minimizing particle populations that lie below the critical zeta potential required for stabilization is important for stability and sets a minimum value for the ratio, and this is illustrated in the Examples below with quantitative measurements, as per the preferred method. It is preferred that the intensity-weighted fraction of particles with zeta potential less than 25 mV in magnitude be less than about 10%, and more preferably less than about 3%. Note that this refers to the intensity-weighted distribution as determined by a light-scattering method, and in cases where, say, 10% of the reported distribution lies below 25 mV in magnitude, it must be remembered that diffusional broadening exaggerates this reported value, and so the actual intensity-weighted population at values below 30 mV will in fact be considerably less than this.

These zeta potential requirements should be met without utilizing undue concentrations of charged surfactant. One reason for this is that the introduction of larger loadings of charged surfactant may lead to an increase in toxicity of the formulation. While ionic surfactants such as SDS, docusate, and benzalkonium chloride (a well known preservative) are currently present in FDA-approved injectable formulations, this is not to say that they are void of toxic effects at even larger doses, particularly in the case of cationic compounds. FDA policies generally recommend the use of the least amount of excipient required for the job, in this case for stabilization.

The use of surfactants with polymeric hydrophilic polar groups, particularly polyethyleneglycol (PEG), such as Pluronics (Poloxamers) or PEGylated sorbitol or glycerol esters, with HLB values greater than about 8 or total PEG molecular weight greater than about 2,000 should be minimized in the practice of this invention since they, like excessive ratios of charged surfactant to cubic phase, have a strong tendency to induce L3 or lamellar phase coatings. Such surfactants are also known to exhibit a "stacking effect" on surfaces; quasielastic light scattering measurements on particles dispersed with high-HLB Pluronics, for example, show an increase in particle diameter as the concentration of the high-HLB Pluronic increases, indicating the stacking of surfactant molecules at the particle surface, which will clearly interfere with particle-cell interactions as discussed herein.

Incorporation of active. There are three general forms in which active can be incorporated in the uncoated particle of the instant invention. These are now described.

First form: In this form—the preferred form—the active is dissolved in the reversed liquid crystalline phase material. Phrased more precisely, the active is one of the components which, together with the other components, form the liquid crystal under the conditions used (temperature, pressure, etc.), as a thermodynamic equilibrium phase. Note that this is not necessarily the same as saying that the active is "added to" the reversed liquid crystalline phase, because the phase to which the active is added could be entirely different before the addition of the active; addition of the active may promote formation of the reversed liquid crystalline phase. For example, in Examples given herein involving propofol the active propofol is solubilized in the liquid crystal as a "first form" i.e. the propofol is solubilized in the reversed liquid crystalline phase material, and is one of the components that form the liquid crystalline material.

Second form: In this form, the active is dispersed in the reversed liquid crystalline phase material, in the form of either crystals, which are preferably submicron, or an amorphous solid form. In this case, by definition, the portion of active that is dispersed, and not dissolved, does not affect the phase behavior of the liquid crystalline material. This type of embodiment can be realized in at least three ways. In the preferred method, the active is physically mixed with the reversed liquid crystalline phase material, and the resulting material is then dispersed in water as disclosed elsewhere herein. Prior to mixing, the active may be subjected to micronization, or even made submicron. If this requires the use of surfactant or other stabilizer, then it must be checked that this stabilizer will not disrupt the reversed liquid crystalline phase, at the levels used. Methods for producing submicron crystals of drug material in a pharmaceutically-acceptable manner have been described, for example in the U.S. Pat. No. 5,510,118 cited above. In a second method of this form, solid active particles are dispersed along with the reversed liquid crystalline phase, with the intention that the liquid crystal will cover the solid active due to a lower interfacial tension, a more favorable sum of interactions between the solid active and liquid crystal, and liquid crystal and polar liquid continuous phase. In the third method, the active is first solubilized, either in the liquid, preferably a polar solvent, or, preferably, in the liquid crystal or a precursor thereof, at, for example, elevated temperature or a favorable pH, and then conditions are changed to precipitate or crystallize the active, preferably in the interior of the liquid crystalline matrix.

Third form: the active is in liquid form, either as a liquid active (for example, in the case of a liquid drug) or as a solution of drug in a liquid phase that is (necessarily) distinct from and interior to the liquid crystalline phase material. This liquid is embedded in the liquid crystalline material, surrounded by a contiguous and continuous matrix of the liquid crystalline material.

Combinations of these three forms are possible. For example, a portion of the active could be solubilized in the liquid crystal, whereas the remainder might be in crystalline form dispersed in the liquid crystal.

In the First Form as just described, where the active is dissolved in the reversed cubic or reversed hexagonal liquid crystalline phase, it is highly desirable that in the final dispersion, the majority of the active is localized in the liquid crystalline phase, that is in the particles, as opposed to in the aqueous exterior. In this way, the use of the invention can take full advantage of the features of the reversed liquid crystalline phase as described herein: the sequestration and protection of the drug both in storage and against attack from biological components of the body; the intimate interactions between the particles and biological membranes; any targeting capabilities built into the particles such as antibodies or lectins; any antioxidant (e.g., tocopherol) or otherwise protective components in the particles; favorable and more physiological conformation and presentation of bioactive compounds especially proteins; biomimetic nature of the vehicle as relate to biomembranes, etc. Furthermore, as discussed herein, a number of drugs are believed to exhibit a harmful effect (e.g., stinging on injection) when present, even in tiny amounts, in the aqueous exterior phase of a microdroplet or microparticulate system, yet not when localized inside a hydrophobic particle or droplet. It is in fact generally preferred in these embodiments that over about 90% of the drug be preferentially located in the particles, and—as seen in Example 18 and the discussion surrounding it—especially preferred if over about 99% of the drug is preferentially located in the particles (see Example 18), particularly in the case where the drug is propofol.

In the Third Form, where the active is a liquid embedded in the liquid crystalline material, surrounded by a contiguous and continuous matrix of the liquid crystalline material, one can reasonably expect that the drug will remain associated with the liquid crystalline material in the body and so reap the advantages of the association. This should be contrasted with U.S. Pat. No. 6,071,524 in which cubic gel particles are situated at the interface between oil microdroplets and the aqueous exterior phase. With the huge surface area of oil-water interfaces in the body, and this topologically weak spatial relationship between the gel particles and the oil droplets, there is good reason to believe (and no evidence given to the contrary in U.S. Pat. No. 6,071,524) that the gel particles will be stripped from the oil droplets in their course through the body, in a pharmaceutical application of U.S. Pat. No. 6,071,524. Nor is there compelling reason to believe that the oil droplets will be transported across a biomembrane barrier even if the cubic gel particles themselves are.

Incorporation of a charged, bilayer-associated component. A key aspect of the invention is the incorporation of an ionically-charged, bilayer-associated compound that induces a charge throughout the bilayer, and creates a surface charge on particles of the liquid crystalline material. There are two general methods for incorporating this charged compound, although the net result is typically not affected by the choice of method. In one method, the charged compound is mixed together with the liquid crystalline material—or in some cases, the reversed liquid crystalline phase requires the presence of the charged compound. In another method, the charged compound is present in the liquid phase, preferably solubilized therein, and the liquid crystal is dispersed in this mixture. In the end, the components will tend toward equilibration, which will tend to minimize the difference between these approaches, such that the charged component will partition between the liquid crystalline particles and the polar phase according to a distribution that eventually would come to an equilibrium, or near-equilibrium, distribution.

The charged, bilayer-associated compound will often, though not always, be a charged surfactant, either an anionic surfactant or, more rarely, a cationic surfactant. Examples of such surfactants, pharmaceutically-acceptable for various routes of administration, are given below. In many embodiments of the invention, however, the charged compound will not satisfy the definition (given above) of a surfactant, but will nonetheless be perfectly well suited as a charged, bilayer-associated compound capable of yielding particles of the instant invention. The charged bilayer associated compound may be the active.

Anionic bilayer-associated compounds. For formulations intended for administration by injection or other non-oral routes, especially preferred anionic moieties for binding the drug are: docusate, dodecylsulfate, deoxycholic acid (and related cholates, such as glycocholate), tocopherol succinate, stearic acid and other 18-carbon fatty acids including oleic, linoleic, and linolenic acids, gentisic acid, hydrophobic amino acids including tryptophan, tyrosine, leucine, isoleucine, aspartic acid, cystine, and their N-methylated derivatives, particularly N-acetyltryptophan, phosphatidylserine, phosphatidylinositol, phosphatidylglycerol (particularly dimyristoyl phosphatidylglycerol), and other anionic and acidic phospholipids. The person with skill in the art will recognize docusate as the anionic moiety of the surfactant docusate sodium (also known as Aerosol OT), and dodecylsulfate as the anionic moiety of the surfactant sodium dodecylsulfate, or SDS. Surface-active polypeptides and proteins, such as casein and albumin, may also be used, although careful attention must be paid to the pH which will have an effect on the charge of the molecule.

For formulations intended for oral administration, the above anionic compounds can be used, but in addition there are a number of other compounds that can provide the anion. These include ascorbyl palmitate, stearoyl lactylate, glycyrrhizin, monoglyceride citrate, stearyl citrate, sodium stearyl fumarate, JBR-99 rhamnolipid (and other biosurfactants from Jeneil Biosurfactant), glycocholic acid, taurocholic acid, and taurochenodeoxycholic acid.

Especially preferred anionic surfactants are: sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps of the form $IC_n$, where the chain length n is between 8 and 20 and I is a monovalent counterion such as sodium, potassium, ammonium, etc.

Cationic bilayer-associated compounds. As discussed herein, currently the selection of pharmaceutically-acceptable cationic surfactants for injection is primarily limited to myristyl-gamma-picolinium chloride and benzalkonium chloride. However, a number of other cationic lipids and surfactants are currently under investigation as pharmaceutical excipients for injectables, including: tocopheryl dimethylaminoacetate hydrochloride, Cytofectin gs, 1,2-dioleoyl-sn-glycero-3-trimethylammonium-propane, cholesterol linked to lysinamide or ornithinamide, dimethyldioctadecyl ammonium bromide, 1,2-dioleoyl-sn-3-ethylphosphocholine and other double-chained lipids with a cationic charge carried by a phosphorus or arsenic atom, trimethyl aminoethane carbamoyl cholesterol iodide, O,O'-ditetradecanoyl-N-(alpha-trimethyl ammonioacetyl)diethanolamine chloride (DC-6-14), N-[(1-(2,3-dioleyloxy)propyl)]-N—N—N-trimethylammonium chloride, N-methyl-4-(dioleyl)methylpyridinium chloride ("saint-2"), lipidic glycosides with amino alkyl pendent groups, 1,2-dimyristyloxypropyl-3-dimethylhydroxyethyl ammonium bromide, bis[2-(11-phenoxyundecanoate)ethyl]-dimethylammonium bromide, N-hexadecyl-N-10-[O-(4-acetoxy)-phenylundecanoate]ethyl-dimethylammonium bromide, 3-beta-[N—(N',N'-dimethylaminoethane)-carbamoyl.

Other useful bilayer-associated compounds. Other suitable charged bilayer-associated compounds for use in the instant invention, which can take up a charge under at least some conditions, include: fatty acids, phenolic compounds such as eugenol, isoeugenol, quinolines, hydroxyquinolines and benzoquinolines, tricyclics such as carbazole, phenothiazine, etc., pigments, chlorophyll, certain natural oil extracts particularly those which are phenolic (such as clove oil, ginger oil, basil oil), biosurfactants (such as Jeneil's "JBR-99"), a wide range of dyes. Amphiphilic proteins and polypeptides can be used, including gramicidin, casein, albumin, glycoproteins, lipid-anchored proteins, receptor proteins and other membrane proteins such as proteinase A, amyloglucosidase, enkephalinase, dipeptidyl peptidase IV, gamma-glutamyl transferase, galactosidase, neuraminidase, alpha-mannosidase, cholinesterase, arylamidase, surfactin, ferrochelatase, spiralin, penicillin-binding proteins, microsomal glycotransferases, kinases, bacterial outer membrane proteins, and histocompatibility antigens. As is well known, every protein has a net charge except at its isoelectric point (pI), and thus a pharmaceutically-acceptable membrane-associated protein is suitable for use in the present invention as long as the pH is away from its isoelectric point. A few such proteins are currently accepted as inactive ingredients for pharmaceutical preparations, at least under some conditions, and these include gluten, casein, and albumin.

Surfactants and lipids. Low-toxicity, especially pharmaceutically-acceptable, lipids and surfactants form the basis of the lyotropic liquid crystalline phases that are a fundamental building block of the current invention. Preferred surfactants which are FDA-approved as injectables and other low-toxicity surfactants and lipids, which are of at least relatively low solubility in water, that are preferred for the present invention for products intended for a number of routes of administration, include those listed in U.S. Pat. No. 6,638,621, the complete contents of which is herein incorporated by reference. The inventor has found the following pharmaceutically-acceptable surfactants to be particularly useful in forming insoluble reversed cubic and hexagonal phases: phosphatidylcholine, phosphatidylethanolamine, Arlatone G, Tween 85, glycerol monooleate and other long-chain unsaturated monoglycerides, sorbitan monooleate, zinc and calcium docusate, and Pluronics with less than about 30% PEO groups by weight, especially Pluronic L122 and to a lesser extent L101; Pluronic P123 (and likewise Pluronic 103) also forms reversed cubic and hexagonal phases but has a significant solubility in water which can limit its usefulness in some applications. The low-MW ethoxylated surfactants OE-2 and OE-5 (oleyl alcohol ether-linked to either 5 or 2 PEG groups) are useful in this respect but their approval in drug formulations is limited, depending on the route of administration.

Polar solvent. Polar solvents are required in the present invention for the creation of the lyotropic liquid crystalline phase material, and preferred as a continuous phase for dispersing said material. Usually, at least in the case of a bicontinuous cubic phase, which is the preferred embodiment, the polar solvent composition in the liquid crystal and in the continuous (exterior) phase will ultimately be equal, or nearly equal, because the two are essentially in hydraulic continuity. It should also be noted that the choice of a non-volatile polar solvent like glycerol can be important in processes such as spray-drying. The polar solvent may be: water; glycerol; formamide, N-methyl formamide, or dimethylformamide; ethylene glycol or other polyhydric alcohol; ethylammonium nitrate; other non-aqueous polar solvents such as N-methyl sydnone, N-methyl acetamide, dimethylacetamide, pyridinium chloride, etc.; or a mixture of two or more of the above, with water-glycerol being the most important of the mixtures.

For the case of drug-delivery, the preferred polar solvents are water, glycerol, N,N-dimethylacetamide, and N-methylacetamide, as well as mixtures thereof. Water-glycerol mixtures are of extremely low-toxicity and are very compatible with many surfactants including phospholipids. Dimethylacetamide-glycerol mixtures are excellent for dissolving difficultly-soluble pharmaceutical compounds.

It can be advantageous in certain circumstances to use, as an alternative form of this invention, a composition that yields a charge-stabilized dispersion of reversed liquid crystalline phase particles upon contact with water (or more rarely, other polar solvent or liquid)—whether or not this dehydrated composition itself is a reversed liquid crystalline phase (i.e., a reconstitutable material that forms uncoated particles when combined with medium (water or some other fluid) where the particles thus formed have an ionic charge which stabilizes them as a solution or dispersion in a liquid (e.g., water). In particular, this contact with water or a water-containing mixture could be either during a reconstitution step, or during the application of the particle, when the particle contacts an aqueous solution such as blood, extracellular fluid, intracellular fluid, mucous, intestinal fluid, etc. This can be in the form of particles, or a precursor liquid, as seen in Example 17, or a solid or semisolid matrix. There are several reasons why this may be advantageous, including the following without limitation: to protect hydrolytically unstable actives or excipients; to limit premature release of water-soluble actives; and as a natural result of a production process such as spray-drying or freeze-drying that can induce dehydration. Removal of most, or all, of the water from a reversed liquid crystalline phase will often yield another nanostructured liquid or liquid crystalline phase, but can sometimes yield a structureless solution, precipitate, or a mixture of these with one or more nanostructured liquid or liquid crystalline phases. In any case, for many applications, it is the hydrated form that is important in the application of the particles, and thus if this hydrated form is a reversed liquid crystalline phase, then the composition of matter falls within the scope of the current invention.

Preferred methods of making. The preferred method of practicing the current invention is as follows, focusing on the case of a pharmaceutical active. One can choose to employ either the reversed bicontinuous cubic phase liquid crystalline material, or less preferably, a reversed hexagonal phase material (less preferable both because of less favorable interactions with biomembranes, and increased risk of toxic and/or antigenic effects). A liquid crystal containing the active is prepared by mixing the active, a surfactant or lipid, water, and if necessary a solubilizing excipient, and mixing thoroughly such that the resulting material is optically isotropic and of high viscosity. Methods for locating and mixing the appropriate composition to achieve this are given in detail in U.S. Pat. Nos. 6,482,517 and 6,638,621 together with U.S. application Ser. Nos. 09/994,937 and 10/460,659 the contents of which are incorporated by reference. To summarize, these methods involve the development of phase diagrams with the aid of polarizing optical microscopy and small-angle x-ray scattering, the application of solubilization-aiding components that are non-paraffinic and typically contain one or more polar groups that are not operative as surfactants (in combination with true surfactants which are, of course, necessary for liquid crystalline behavior), and judicious use of techniques useful for speeding dissolution such as heating, sonication, vigorous stirring/kneading, etc. The concentration of active should be high enough that an effective therapeutic amount (a "dose", to generalize a term from pharmaceutics) requires no more than about 10 grams of liquid crystal, and more preferably no more than about 2 grams. If the surfactant or lipid is not strongly charged—and this will typically be the case in pharmaceutical applications, especially injectable formulations, because most of the FDA-approved surfactants and lipids approved for relatively high concentration use (as needed in the liquid crystal) are not highly charged—then a relatively small amount of charged, bilayer-associated compound must be incorporated, and this is preferably a charged surfactant. For the cases where this additive is needed (that is, where the cubic phase itself does not have a charged surfactant as its main surfactant component), the weight ratio of the charged, bilayer-associated compound to the liquid crystal should be between about 0.01:1 and 0.15:1, or more preferably between about 0.02:1 and 0.08:1. Weight ratios larger than 0.08:1, and especially ratios larger than 0.15:1, will have a tendency to induce an L3 phase or lamellar phase that can become an interfering coating. Ratios lower than 0.01:1 will not yield sufficient surface potential to stabilize the particles in dispersion. Although the preferred method of incorporating a charged surfactant additive—provided it is water-soluble—is by dissolving it in the water that is used to disperse the cubic phase, it should first be checked that the cubic phase is not melted by the addition of small amounts of the surfactant.

The cubic phase is then dispersed in the surfactant solution, or in the other case the charged cubic phase is dispersed in water or some sort of buffer/aqueous solution, using homogenization or other mechanical means, preferably followed by microfluidization. In the production of particles of this invention and their size-reduction, a number of emulsification methods could be used as energy inputs. These include sonication, microfluidization, valve homogenization, blade stirring, etc. When submicron particles are required (e.g., in intravenous applications), microfluidization is the preferred method since the shear rates and temperature spikes can be best controlled in that method. Filtration or extrusion, in combination with these methods, can be of great help in reducing particle size, and can serve a sterilization purpose at the same time. Homogenization of the particle size down to a few microns followed by filtration at 0.45 or 0.2 microns is another preferred means of producing fine particles of this invention. In cases where the stiffness of the reversed liquid crystal interferes with filtration, it can help to raise the temperature so as to perform the filtration at a temperature where the liquid crystal melts into a liquid phase (typically L2, L3 or microemulsion phase), making the sizing by filtration easier, and then reducing the temperature back to ambient to return the particles to the liquid crystalline form.

Sterilization of the finished product can be either by filtration, preferably at 0.2 microns, or by other methods known in the art, such as UV or pulsed UV light, gamma irradiation, e-beam sterilization, steam sterilization, or when possible by terminal heat sterilization. Since many of the components used in the practice of this invention will be liquids at or near ambient temperature (e.g., many of the Pluronics, tocopherol, essential oils, aqueous solutions, and L2 phases that result from mixing cubic phase compositions minus water or other liquid component), there is also the possibility of starting with sterilized liquid components (e.g., by sterile filtration) and processing under sterile conditions.

Supercritical fluids can also provide other means by which to make the invention, with supercritical carbon dioxide being the preferred solvent. Methods that apply sonication and other high-frequency energy to compositions dissolved in supercritical carbon dioxide, with the carbon dioxide coming off as a gas leaving microparticles, can be used.

Validation and quantification of charge stabilization. In the context of the instant invention, measurement of surface charge, preferably in the form of particle zeta potential, is crucial to validating that particles of the invention are indeed present, predicting long-term stability characteristics, and to quantifying the electrostatic repulsion. In particular, as discussed above, in the course of this work it was established that once the zeta potential of a collection of these reversed liquid crystalline phase particles equals or exceeds about 25 mV, or more preferably 30 millivolts, in magnitude (or is less than −25 mV or −30 mV in magnitude), then no other mechanism is required for stabilization of the dispersion against flocculation, provided that there are no exceptional attractive forces, such as intermingling of surface-associated polymer chains, unusual ionic conditions, time-dependent redistributions within the particles, etc.

In the present art, historical microscopy-based estimates of electrophoretic mobilities have been largely replaced by more quantitative light-scattering methods. This is not to say that microscopy-based methods are useless, but in the present context, with the focus on submicron and even nanoscale microparticles, light-scattering methods are far better suited. This is notwithstanding the fact that for systems containing larger particles, such as subcutaneous formulations, microscopy-based determinations using electrophoretic observation cells can be very useful and yield more direct, intuitive information, and such methods can even extend down to submicron particles particularly with specialized optics such as Differential Interference Contrast (DIC, also known as Nomarski optics). In any case, The DELSA 440SX measurements reported herein have been crucial to optimizing the compositions used in the present invention, particularly the ratio of charged surfactant to liquid crystal, and especially in the task of eliminating or minimizing particle populations that lie below the critical zeta potential required for stabilization without utilizing undue concentrations of charged surfactant.

In the Examples given herein, the conditions/settings typically applied were representative of the preferred procedure for determining zeta potential. The samples were loaded into a silver-coated sample cell, undiluted or only mildly diluted, which is important because dilution can affect zeta potentials by a number of effects. Conductivities were typically on the order of 0.1 mS/cm, and the current in milliamps was set to a value somewhat larger than half the value of the conductivity in mS/cm; for example, in one Example, the conductivity was 0.311 mS/cm and the current was set to 0.2 mA. The frequency shift was first set to 500 Hz, and if the measurement indicated that a setting of 250 Hz would be acceptable then a second measurement was taken at 250 Hz. At the latter frequency shift, instrumental broadening was often considerably reduced compare to the 500 Hz reading; however, particularly at the higher angles of measurement, the peak shape could appear to have a tail at the higher zeta magnitude end, due to the so-called "homodyne" effect.

This instrument measures zeta potential at up to four angles simultaneously: 8.9, 17.6, 26.3 and 35.2 degrees. As is well known in the art of light-scattering, smaller angles emphasize larger particles, and vice versa. This means that at the larger angles, since smaller particles are emphasized more, diffusional broadening is more pronounced.

The presence of a sharp peak at an indicated zeta potential of zero, in the present context at least, is nearly always due to material that is either stuck to the walls of the cell, or settled to the bottom. In the Examples of the present disclosure, this has much more to do with the particle size than any other parameter, except for the fact that cationic particles have a slightly larger tendency to stick to quartz (the material of the DELSA sample cell) due to an interaction with the weak anionic charge of quartz at the pH values investigated herein.

The simultaneous measurement at different angles is also important in validating the measurement. In short, since this measurement (as with nearly any scientific or engineering measurement) has noise associated, the question of whether or not a given peak or feature is real or artifact can be made easier and more substantial by checking whether or not the peak or feature is present in only one curve, or several (and preferably all) curves corresponding to the different angles of measurement.

Dry or Reconstitutable Systems

Dry, partially dry, reconstitutable and other materials that form or revert to particles of the type disclosed herein are within the spirit and scope of the present invention. Such systems can be prepared by a number of methods. For one, they may be obtained by freeze-drying liquid crystalline particles, or drying such particles by other means involving vacuum and/or heat input. Spray-drying, fluid-bed dryers and similar techniques can also be applied to either aqueous dispersions of particles, or to precursor solutions of the nonaqueous components of the particles dissolved in a volatile organic solvent. All of the three forms of the invention discussed above can be dehydrated by at least some of these means to produce reconstitutable systems.

This approach is especially useful when one can take advantage of the fact that many reversed lyotropic liquid crystals become solids upon removal of their water. Examples of surfactants and lipids that form reversed liquid crystalline phases upon hydration but are (effectively) solid in dried form are monoelaidin, sodium docusate (and other salts of docusate), certain phospholipids depending on acyl chain unsaturation, and mixtures of didodecyldimethylammonium bromide with tetradecanol.

Alternatively, drying a dispersion can produce a reconstitutable system of several sorts. If there are relatively small amounts of non-volatile components in the exterior phase of the dispersion, then drying will leave either a fused mass—essentially the original contiguous liquid crystal—or a collection of distinct particles that can, at least in principle, be redispersed with a relatively low input of energy. The latter scenario can be promoted by selection of a higher melting point surfactant or other component.

By incorporating a non-volatile additive in the exterior phase, preferably dissolved but alternatively dispersed, drying can result in particles that are kept from liquid crystal-liquid crystal fusion by the presence of an intervening solid. Selecting an additive that is oppositely-charged from the liquid crystalline particles can aid in establishing the proper localization of the resulting solid. Since the solid is either soluble, or readily dispersible, in the original liquid (usually water), then addition of this liquid will generally result in prompt reconstitution of a dispersion. Particle size of the reconstituted dispersion may be the same as that of the original dispersion, but in the event it is larger, then simple methods as described herein can be used to reduce the particle size; in particular, in many cases a filtration or extrusion step will induce the desired particle size while sterilizing as well, and a syringe filtration step is a well-accepted procedure even in the case of a bedside reconstitution.

Reversed Liquid Crystalline Phase Induction

In some instances, the active of interest is such that it induces a reversed liquid crystalline phase in a selected lamellar-forming lipid-water or surfactant-water system. As a particularly important and preferred case of this, the lipid-water system is a phospholipid-water system, especially a phosphatidylcholine-water system in which the phospholipid is sufficiently unsaturated to form a lamellar liquid crystalline system at or near ambient temperature. Phosphatidylcholine purified from most plant sources, as well as a number of synthetic PC's with unsaturated chains, are well known to form lamellar liquid crystalline phases at room temperature. However, it is much less well known that the addition of certain hydrophobic or amphiphilic compounds can induce the lamellar phase to convert to a reversed cubic, or less commonly reversed hexagonal, phase. Many solubilizing oils, such as a number of essential oils (indeed, the majority of these), induce reversed cubic phases, typically at levels between about 10 and 35% of the final composition. Certain actives, including pharmaceutical actives such as propofol, also induce cubic phases in phosphatidylcholine-water systems, as the current inventor has found. These surprising cases, where the drug—or a drug/diluent combination, such as a mixture of propofol and tocopherol—is found to induce a reversed liquid crystalline phase in an otherwise lamellar-forming surfactant-water mixture, are especially well-suited for this invention. This is illustrated by the large loadings (29% by wt.) that are achievable in the PC-propofol-water cubic phase in the Examples shown below, which resulted in low levels of excipients being delivered in the course of treating a mammal with the formulation.

Applying the Invention.

The uncoated particles of the present invention have application in a variety of fields. The particles may be adapted to absorb one or more materials from a selected environment, adsorb one or more materials from a selected environment or, most preferably, to release one or more materials, such as active agents, into a selected environment.

With respect to absorption, the particles may be used, for example, to harvest products or scavenge waste in biological or chemical reaction processes; or to remove toxins, antigens or waste products in medical applications.

With respect to adsorption, for example, the particles may be used as chromatographic media and as adsorbents. In applications where the active agent is a target molecule that is capable of capturing an analyte, such as a biologically or chemically important molecule or other compound from the surrounding medium, the uncoated particles of this invention have an advantage over coated particles of any sort in that the liquid crystal is presented directly to the medium with the least amount of interference.

With respect to release, the particles may be used for the controlled release of pharmaceutical agents such as anticancer agents or photodynamic therapy agents, local and general anesthetic agents, anesthetic reversal agents, or cosmetic, nutritional, nutriceutical, or cosmeceutical materials. An active agent may be located within the particles for release upon the triggering of release.

One very valuable aspect of the invention applies in particular to highly insoluble actives, insoluble drugs in particular. A major focus in drug development is the water solubility of drug candidates, and considerable resources are spent measuring, optimizing, and evaluating this solubility, even in cases where it is very low. The prevalent conception is, in fact, that this is a crucial parameter because, at some point in the path to absorption, the drug will have to dissolve in water en route to the target cell membrane. However, it is recognized in this invention that uncoated particles as disclosed herein, which interact intimately with target membranes, can greatly reduce or even circumvent the need for diffusion of "naked" drug (drug that is no longer in the particle core) across aqueous paths to reach the target membrane—aqueous paths which themselves represent barriers, effectively. Indeed, it is envisioned that from the moment a drug molecule is dissolved in a particle of the present invention, to the point it is located in the target cell membrane, it need never cross over an aqueous path; the particle can incorporate the active as a component up to the target cell, at which point the reversed liquid crystalline phase can fuse and integrate with the target cell membrane, depositing the drug directly into the cell membrane.

Proteins, polypeptides, nucleic acids, polysaccharides, lectins, antibodies, receptors and other biomacromolecules are actives that can be particularly well suited for the current invention. The reversed liquid crystalline phase can provide the absorption enhancement properties discussed herein—which can be especially important in the case of macromolecules—while at the same time providing protection against degrading proteins (proteases, nucleases, glycosidases, antibodies, etc.) and cells that would otherwise inactive or sequester the active; such protection can in fact be provided by the effect of the controlled pore size of the reversed liquid crystalline phases, or by virtue of the lack of accessible pores in the discrete (non-bicontinuous) cubic phase though this phase is less effective than the bicontinuous cubic phase at enhancing transport. The uniform poresize in the reversed bicontinuous cubic phase and the reversed hexagonal phase can likely be utilized to release a large molecule in response to a physiological or other condition (e.g., temperature or hydration, in a laundry detergent application) that induces a microstructure with poresize large enough to release the macromolecule. As with small molecules, release of the active can also be triggered by changes in ionic conditions, such as a change in pH, salinity, divalent ion concentration, hydrogen bonding species, or even cleavage of bonds between the active and a component of the liquid crystal by either chemical or biochemical (e.g., enzymatic) action. In some cases, it will not be necessary to release the active, if it is a reactive or catalytic compound, particularly a protein, provided the substrate or other reactant(s) is able to pass through the pores of the reversed liquid crystalline phase material. In the case of nucleic acids in particular, but also in other cases, particles of the current invention could be of great utility in delivering actives to intracellular sites, such as the nucleus or nuclear membrane, the Golgi apparatus, the endoplasmic reticulum, the mitochondria, etc., and in such a case the transport-enhancing properties of the reversed liquid crystalline phase materials, particularly the reversed bicontinuous cubic phases, can be of high utility in the context of an uncoated particle.

In cases of pharmaceutical application of the invention where the drug is disposed in the particle in crystalline form (as opposed to solubilized), within a reversed liquid crystalline microparticle, and thus surrounded by a contiguous and continuous matrix of the liquid crystalline material, and particularly when the particles are also submicron in size, then the reversed liquid crystalline material portion of the particle can serve a number of functions simultaneously, including but not limited to: stabilizing the particles in dispersion; enhancing absorption by improving interactions with biomembranes and other barriers; serving as a matrix for the solubilization of other excipients or co-factors; serving as a matrix for the solubilization of efflux protein inhibitors in particular; providing a means by which to modulate, and even reverse, the effective charge on the drug; provide improved compatibility with certain drug formulation approaches; provide for modulation of the deposition characteristics of drugs by the presence of a bioadhesive and/or high-viscosity matrix; provide for poresize-selective protection from, or access of, biomacromolecules (e.g., albumin, proteases, nucleases, esterases) to the solid drug; in the case of a prodrug, provide for drug targeting or controlled release delivery by permselective access and/or controlled dissolution of the matrix; and provide for improved stabilization of the drug dispersion in biological fluids by the use of liquid crystals that have much lower solubilities than most of the surfactants previously used in nanocrystal stabilization.

One particularly important potential application of the invention is for hosting molecules, such as antibodies, receptors, ligands, nucleic acids, oligosaccharides, or other compounds that can bind an analyte molecule in a diagnostic situation. In a preferred embodiment of such an application, a target compound capable of binding a chemical of interest is partitioned into a particle of the current invention. In a competitive assay or simple segregation application of the invention, the chemical of interest will diffuse into the porous reversed liquid crystalline particle and bind to the target. In competitive assays, a displaceable chemical such as an enzyme group or the like will be displaced by the chemical of interest and will diffuse out of the porous reversed liquid crystalline particle and react with a marker compound to indicate binding has occurred within the particle; see in particular U.S. application Ser. No. 10/170,214. Thus, the nanostructured liquid crystalline particle keeps the enzyme or other displaceable groups separate from the marker compound until it is released from the target, thereby allowing accurate detection without complex washing, aspiration and other processes used in many equipment-intensive automated immunoassay analyzers. This allows clinicians to conduct tests quickly and accurately, without sophisticated training or instrumentation. In a sandwich assay application of the invention, a ligand is bound to the target within the porous reversed liquid crystalline particle, or can become bound to the target by diffusion through the porous liquid crystalline material. In addition, a second target that can diffuse through the reversed liquid crystalline material is added which binds to another epitope of the ligand. Once the second target is bound, an indication is provided demonstrating the binding. In such applications wherein the target must bind a molecule from a milieu of interest, again the presence of a coating is intrusive, even a porous L3 phase because of its tendency (described above) to form lamellar phase domains, which can be of very low permeability to a wide range of compounds. Indeed, this is the reason why nature uses bilayers to compartmentalize cells.

Alternative uses of the invention are in chemical isolation and clean up, or in the delivery of enzymes, or other bioactive agent, e.g., radioactive agents and chemical toxins. In the chemical isolation application, the particles of the present invention are brought into contact with a medium in which segregation and isolation of a chemical of interest is desired. Over a period of time, and with or without operations such as stirring, agitation, etc., the chemical diffuses within the porous reversed liquid crystalline particle and is bound by the target. This process may be used in the clean up of contaminated water, or in the ex vivo clean up of blood, for example. In the delivery mode, the porous liquid crystalline particle would incorporate a chemical to be delivered (e.g., an agonist, antagonist, medicament, toxin, etc.). This chemical would be protected from the environment, e.g., the body in an in vivo application, by the porous liquid crystalline particle, until it is in position for delivery of the chemical. Once in position, a compound from the environment will diffuse through the porous liquid crystalline particle, competitively interact with the target and displace the chemical to be delivered, and, thereafter, the chemical to be delivered will diffuse out of the porous reversed liquid crystalline particle and into the environment in which it should act.

Various other applications of microparticles in general are known, including those listed in U.S. Pat. No. 6,638,621, the complete contents of which are herein incorporated by reference.

In view of the demanding requirements for the delivery of pharmaceuticals, the advantages and flexibility of the present invention make it particularly attractive in the delivery and release of many pharmaceutical compounds, particularly for the delivery and release of therapeutic amounts of such substances. Pharmaceutical compounds that are particularly well-suited for incorporation as actives in the instant invention, and suffer from problems or limitations in the currently-marketed formulations, include propofol, alphaxalone, alphadolone, eltanolone, propanidid, ketamine, pregnanolone, etomidate, and other general anesthetics; bupivacaine, lidocaine, procaine, tetracaine, mepivacaine, etidocaine, oxybuprocaine, cocaine, benzocaine, pramixinine, prilocaine, proparacaine, ropivicaines, chloroprocaine, dibucaine, and related local anesthetics; SN-38 and related camptothecins; paclitaxel and related taxanes; doxorubicin, idarubicin, daumorubicin and related rubicins; amphotericin B; coenzyme Q10; steroids and steroidal anti-inflammatory agents; nonsteroidal anti-inflammatories (e.g., salicylates, para-aminophenol derivatives (e.g., acetaminophen), fenomates, proprionic acid derivatives (e.g., naproxen, ibuprofen, etc.); analgesics; antipyretics; sedatives (e.g., benzodiazepines such as diazepam); hypnotics (e.g., intravenous anesthetics and barbiturates); opiates; cannabinoids and proteins (e.g., insulin and erythropoietin)(it being understood that a wide variety of amides and esters may have application in the present invention). In addition, various antineoplastic agents and other pharmaceutical compounds listed in U.S. Pat. Nos. 6,638,537 and 6,638,621, the complete contents of which are herein incorporated by reference We note that the current invention is also very well suited for the incorporation of functional excipients, such as essential oils that improve absorption of poorly-absorbed drugs, in some cases by inhibiting drug efflux proteins. As discussed in more detail elsewhere herein, there are a number of sites within, and at the surface of the particles, where actives, excipients, and functional excipients can be localized within the context of this invention.

In the area of pharmaceutics and nutriceutics, the particles of the present invention may be administered to a mammal (including a human), or other animal, by any of a variety of routes of administration which are well established and well known to those of skill in the art. These include but are not limited to oral (e.g., via pills, tablets, lozenges, capsules, troches, syrups and suspensions, and the like) and non-oral routes (e.g. parenteral, intravenous, intraperitoneal, intrathecal, intramuscular, subcutaneous, intra-arterial, rectal, intravaginal, sublingual, intraocular, transdermal, intranasal, via inhalation, in a suppository, and the like). The compositions of the present invention are particularly suited for internal (i.e., non-topical) administration, but, in some applications may be topically provided. The present invention is especially useful in applications where a difficultly soluble pharmaceutical active is to be delivered internally (i.e., non-topical), including orally and parenterally, wherein said formulation is to be mixed with a water continuous medium such as serum, urine, blood, mucus, saliva, extracellular fluid, etc. In particular, an important useful aspect of many of the structured fluids of focus herein is that they lend themselves to formulation as water continuous vehicles, typically of low viscosity.

It should be noted that, in the case of injectable formulations, the compositions of this sort reported in U.S. Pat. Nos. 5,756,108 and 6,071,524, in particular, are not applicable, because they are centered around the use of unsaturated monoglycerides, which are highly toxic on injection and not approved for use in injectable formulations. Similarly, U.S. application 2002/0153509 teaches away from injectable particles with its nearly exclusive focus on monoolein.

Incorporation of targeting groups and bioactive compounds. In the present invention it can be very effective to incorporate chemicals or chemical groups—often proteins or other biomacromolecules—that can be invoked to target particles temporally and spatially, for example, to target particles to specific sites in the body. Similarly, other bioactive compounds incorporated on or in the particles could serve important functions, such as: absorption enhancers such as menthol could be present so as to increase permeability of absorption barriers (lipid bilayers, gap junctions) prior to or concomitant with the release of drug; proteins or other adsorption-modulating materials could be incorporated that would inhibit unfavorable binding of endogenous proteins such as albumin; adjuvants could be incorporated that would enhance the effect of vaccine components or other immune modulating materials. Antibodies, steroids, hormones, oligo- or polysaccharides, nucleic acids, vitamins, immunogens, and even nanoprobes are all examples of a wide range of materials that could be attached to particles of the instant invention, either by solubilization or compartmentalization in the liquid crystalline material, or by covalent bonding, ionic bonding, coordinate bonding, hydrogen bonding, adsorption, specific biochemical interactions (such as avidin-biotin binding), or other chemical interactions with components in the particle.

While it is not always crucial for a given application to know the exact localization (or more precisely, the spatial probability distribution) of a targeting moiety within or in association with a particle, this may be an important consideration in the design of a particle-targeting moiety combination, and the instant invention lends itself to a good deal of flexibility and power in this respect. Typically, targeting moieties could be substantially localized at one or more of the following sites in reference to the microparticle:

1) in the particle, i.e., dissolved or dispersed in the reversed liquid crystalline phase interior; this locality can offer the distinct advantage of providing a "biomimetic" milieu for the targeting moiety, a milieu which can comprise a lipid bilayer as well as hydrophilic domains each of which can be tuned to optimize the environment; also, this is the preferred location in the case where the microparticle is used in the diagnostic methodology described in U.S. patent application Ser. No. 10/170,214;

2) at the surface of the particle; and/or 3) attached to, but at a distance from, the surface of the particle, through attachment via a flexible spacer, e.g., a polymer that is attached (e.g. by covalently bonding) at one end to a component of the particle and at the other end to the targeting moiety. Experience with other types of microparticles in the art has shown that this is generally an excellent approach for achieving good targeting because it preserves important conformational and diffusional degrees of freedom that are sometimes required for good docking of a targeting moiety with a receptor or target.

It is also possible in the present invention to create a responsive targeting moiety by tuning the conditions of the formulation such that the targeting moiety is located preferentially in the protective interior of the particle until such time as it is needed for its targeting task, at which point local conditions such as pH or ligand concentrations could induce the moiety to leave the interior of the particle and present itself at, or outside of (via a spacer) the particle surface. For example, if a targeting moiety had a net charge, say cationic, at the pH values encountered during product shelf and even in transit to the site of action, thereby sequestering the target moiety in the interior of the particle where anionic compound(s) are present; during application, upon reaching the site of action, a change in pH, ionic strength, specific ion concentration, surfactancy, ligand concentration or other parameter could release the targeting moiety by interrupting the ionic binding or otherwise releasing the moiety (possibly by mass action), such that the moiety could come to the particle surface and become available for binding to the target. Sequestration of the moiety could greatly enhance the stability of the moiety particularly in view of the small pore-sizes of reversed liquid crystalline phases, which are sufficiently small to occlude the passage of certain large molecules such as proteases, nucleases, etc.

A number of compounds could potentially be used as targeting moieties in a pharmaceutical application of particles of the instant invention. To begin with, certain lipids, such as Lipid A, have very specific interactions with components of the immune system, for example, and can be incorporated into the particles. Similarly, block copolymers in which one of the blocks could have targeting potential, such as glycogen and heparin, may be utilized. Small molecules that could be present in the particle to achieve a degree of targeting include sterols, fatty acids, gramicidin, fragments or simulants of appropriate protein epitopes, and amino acids including aspartic acid, cysteine, tryptophan, leucine and others.

The ability of the reversed liquid crystalline phases of the instant invention to provide for solubilization and stabilization of biomolecules, such as the targeting moieties of focus here, has been described above, where a number of examples of membrane proteins are given (receptor proteins, such proteins as proteinase A, amyloglucosidase, enkephalinase, dipeptidyl peptidase IV, gamma-glutamyl transferase, galactosidase, neuraminidase, alpha-mannosidase, cholinesterase, arylamidase, surfactin, ferrochelatase, spiralin, penicillin-binding proteins, microsomal glycotransferases, kinases, bacterial outer membrane proteins, and histocompatibility antigens), many of which could serve a targeting role if incorporated in particles of the instant invention.

In yet another embodiment of the invention, "externally-directed targeting" of the particles may be achieved. This may be accomplished by directing particles containing certain magnetically responsive materials (e.g., ferric oxide), dispersed in the particle or tethered to it, through the application of magnetic fields.

Antibodies are broadly useful for targeting to specific sites or molecules in the body or other environments, and can be incorporated at various sites in a particle as discussed above. In particular, intact antibodies with their more hydrophobic Fc fragment are prone to partitioning into matrices of the type used in this invention, and furthermore it is well known that antibodies can be adsorbed or attached (including covalently) to surfaces with retention of binding and binding specificity. Commercial sources supply a plethora of antibody types, for example, those listed in U.S. Pat. No. 6,638,621, the complete contents of which is herein incorporated by reference, and others which are continually under development.

Alternatively, many substances (e.g. folate, P-gp, cytochrome P450, and EGF) may in and of themselves be useful as targeting substances and may be incorporated into the particles of the present invention.

It is important to point out that in addition to targeting compounds per se, active compounds, functional excipients such as absorption enhancers, and other bioactive materials as gleaned from the lists of materials given herein can be incorporated in any of these localization sites.

In addition to the targeting of particles to specific sites for release of drug, as mentioned above particles incorporating certain radiopaque or optically dense materials could themselves be used for imaging, and when coupled to targeting compounds as described herein could target specific sites in the body and allow their visualization. As an example, somatostatin receptors are known to be localized at certain tumor sites, so that the attachment of a target to particles as per the instant invention that would bind selectively to somatostatin receptors could target a tumor and allow visualization via, e.g., x-ray, MR imaging, or radioimaging. To extend this idea, a similarly targeted particle could then carry a radioactive material that would emit radiation intended to induce necrosis of the tumor.

Polymerized liquid crystals as phases. U.S. Pat. No. 5,244,799 (the contents of which are hereby incorporated by reference in entirety) reports the polymerization of nanostructured cubic and hexagonal phase liquid crystals, with retention of their nanostructure. The retention of structure was demonstrated by small-angle x-ray scattering (SAXS) and transmission electron microscopy (TEM).

The possibility of polymerizing the cubic phase of a particle of the instant invention opens up a number of possibilities, particularly as relate to increasing the stability of the reversed liquid crystalline phase and modulating its interaction with the body, and cell membranes in particular. For an example of the latter, whereas an unpolymerized cubic phase might be expected to molecularly disperse when coming into contact with a biomembrane, polymerization might create a particle that would retain its integrity throughout its interaction with the same biomembrane, and this could have dramatic consequences as to the fate of the particle and to a drug inside the particle. Furthermore, the retention of a bilayer-bound drug (hydrophobic small molecule, membrane protein, etc.) might be increased tremendously by polymerization, yielding a slow-release particle. And the presence of a more permanent, precisely-defined pore structure, with precisely tunable poresize, might make possible improved controlled release of a drug, and/or sequestration of the drug from degradative or other enzymes by size-exclusion from the pores of the polymerized matrix.

Partitioning control. In the context of this invention, it is sometimes possible to adjust the partitioning of one or more compounds, the active in particular, into or out of the particles—so as, for example, to significantly reduce the levels of free drug in the exterior, aqueous phase. Examples of pharmaceutical compounds where this is important include diazepam, and propofol, where the presence of propofol in the exterior phase is believed to be responsible for the burning that is experienced by many upon injection. This is in spite of the fact that, in the case of propofol, the amount of drug which is in the aqueous phase is less that 1% of the amount of propofol that is in the particles—that is, in the cubic phase—in all cases (see Example 18 in particular), or, phrased otherwise, that over 99% of the propofol is in the particles. Other cases would include where the active compound is sensitive to hydrolysis, oxidation, electrolysis, cavitation, or broadly any form of chemical attack from species (ions, nucleophiles, electrophiles, radicals, etc.) which are more polar and localize preferentially in the aqueous phase. The general approach is to dilute the drug in the particles with a compound, preferably a liquid or at least a low-melting compound, that has a high partition coefficient, preferably greater than about 10, more preferably greater than about 100, and most preferably greater than about 1,000. This increases the volume of hydrophobic material in the particles and in the dispersion relative to the mass of drug, irregardless of whether the diluent compound has a particular affinity or solubilization potential for the drug (provided that the drug is soluble in, or miscible with, the diluent). What makes this approach work effectively and efficiently in the context of this invention is the fact that the high-$K_{ow}$ diluent can be chosen such that it mimics the molecular polar-to-apolar group ratio of the drug, so that the reversed cubic or reversed hexagonal phase can be found with the diluent-drug combination at the same, or similar, volume fraction as that in the system without diluent. For instance, in Example 19 below, a reversed cubic phase in the Pluronic L-122/propofol/water system is found with the drug propofol at approximately 19% by volume, or alternatively, in the system with diluent, at a total propofol (10%) plus tocopherol (9%) volume fraction also of approximately 19%. Similarly, in Example 20, a reversed cubic phase in the phosphatidylcholine/propofol/water system is found with the drug propofol at approximately 29% by volume, or alternatively, in the system with diluent, at a total propofol (10%) plus tocopherol (19%) volume fraction also of approximately 29%. This is particularly important in cases where the extent of the desired liquid crystalline phase region in composition space (i.e., the phase diagram) is relatively small. In making this dilution, it is highly preferable when the diluent is chosen so as to mimic the drug molecule in terms of the ratio of polar groups to apolar groups. For example, tocopherol, with its benzopyranol group (2 oxygens) as part of a 430-MW compound is similar in polar/apolar ratio to propofol, with its single phenolic group (I oxygen) as part of a 178-MW molecule. Polar groups such as hydroxyls are believed to bind strongly to the polar-apolar interface of surfactant-water systems, and since this has important implications for phase behavior [see, for example, P. Strom and D. M. Anderson, *Langmuir* (1992) 8:691-702], the diluent should preferably have a similar content of similar polar groups, to the extent possible.

In cases where the active is propofol, and with other drugs and nutrients which are given to patients for whom the intake of lipids must be controlled, it is an important advantage of many of the formulations reported herein that the lipid loads can be made very low. Particularly in the Pluronic-based cubic phase formulations, reported in Examples 1-4, and 13-17, the lipid load is significantly lower than in the currently marketed formulations, and furthermore this can reduced by incorporating up to 19% propofol in the cubic phase without any alpha-tocopherol. Particularly in applications of propofol where it is used repeatedly or continuously over time as a sedative, lipid loads from the formulation can significantly interfere with the patient's nutritional regiment or even cause serious complications.

Alpha-tocopherol, or other forms of vitamin E such as tocopherol acetate and tocopherol succinate, is a highly preferable choice as a high-partition-coefficient diluent for injectable products because of its long history of safe use in injectable products, as well as the interface-bound OH group cited above. Other preferred diluents include essential oils of plant origin, as well as a number of other liquids that are listed on FDA's list entitled Inactive Ingredients for Currently Marketed Drug Products and/or the appropriate sections of the Food Additives Status List. Among these are: benzyl benzoate, cassia oil, castor oil, cyclomethicone, polypropylene glycol (of low MW), polysiloxane (of low MW), cognac oil (ethyl oenanthate), lemon balm, balsam of Peru, cardamom oleoresin, estragole, geraniol, geraniol acetate, menthyl acetate, eugenol, isoeugenol, petigrain oil, pine oil, rue oil, trifuran, annato extract, turmeric oleoresin, and paprika oleoresin. Essential oils from plant sources (including their extracts and components, and mixtures thereof) comprise a rather large and chemically diverse group of liquids that include many low-toxicity hydrophobes with polar groups. The term "essential oils" is intended to include essential oils from the following sources: allspice berry, amber essence, anise seed, arnica, balsam of Peru, basil, bay, bay leaf, bergamot, bois de rose (rosewood), cajeput, calendula (marigold pot), white camphor, caraway seed, cardamon, carrot seed, cedarwood, celery, german or hungarian chamomile, roman or english chamomile, cinnamon, citronella, clary sage, clovebud, coriander, cumin, cypress, eucalyptus, fennel, siberian fir needle, frankincense (olibanum oil), garlic, rose geranium, ginger, grapefruit, hyssop, jasmine, jojoba, juniper berry, lavender, lemon, lemongrass, lime, marjoram, mugwort, mullein flower, myrrh gum, bigarade neroli, nutmeg, bitter orange, sweet orange, oregano palmarosa, patchouly, pennyroyal, black pepper, peppermint, petitegrain, pine needle, poke root, rose absolute, rosehip seed, rosemary, sage, dalmation sage, santalwood oil, sassafras (saffrole-free), spearmint, spikenard, spruce (hemlock), tangerine, tea tree, thuja (cedar leaf), thyme, vanilla extract, vetivert, wintergreen, witch hazel (hamamelia) extract, or ylang ylang (cananga). The following components of essential oils are also preferred: 2,6-dimethyl-2,4,6-octatriene; 4-propenylanisole; benzyl-3-phenylpropenoic acid; 1,7,7-trimethylbicyclo[2.2.1]heptan-2-ol; 2,2-dimethyl-3-methylenebicyclo[2.2.1]heptane; 1,7,7-trimethylbicyclo[2.2.1]heptane; trans-8-methyl-n-vanillyl-6-nonenamide; 2,2,5-trimethylbicyclo[4.1.0]hept-5-ene; 5-isopropyl-2-methylphenol; p-mentha-6,8-dien-2-ol; p-mentha-6,8-dien-2-one; beta-caryophyllene; 3-phenylpropenaldehyde; 3,7-dimethyl-6-octenal; 3,7-dimethyl-6-octen-1-ol; 4-allylanisole; ethyl 3-phenylpropenoic acid; 3-ethoxy-4-hydroxybenzaldehyde; 1,8-cineole; 4-allyl-2-methoxyphenol; 3,7,11-trimethyl-2,6,10-dodecatrien-1-ol; 1,3,3-trimethylbicyclo[2.2.1]heptan-2-ol; 1,3,3-trimethylbicyclo[2.2.1]heptan-2-one; trans-3,7-dimethyl-2,6-octadien-1-ol; trans-3,7-dimethyl-2,6-octadien-1-yl acetate; 3-methyl-2-(2-pentenyl)-2-cyclopenten-1-one; p-mentha-1,8-diene; 3,7-dimethyl-1,6-octadien-3-ol; 3,7-dimethyl-1,6-octadien-3-yl acetate; p-menthan-3-ol; p-menthan-3-one; methyl 2-aminobenzoate; methyl-3-oxo-2-(2-pentenyl)-cyclopentane acetate; methyl 2-hydroxybenzoate; 7-methyl-3-methyl-ene-1,6-octadiene; cis-3,7-dimethyl-2,6-octadien-1-ol; 2,6,6-trimethylbicyclo[3.1.1]hept-2-ene; 6,6-dimethyl-2-methylenebicyclo[3.1.1]heptane; p-menth-4(8)-en-3-one;

p-menth-1-en-4-ol; p-mentha-1,3-diene; p-menth-1-en-8-ol; ethyl methylphenylglycidate; and 2-isopropyl-5-methylphenol.

Especially preferred diluents, due to a favorable combination of good drug-solubilizing properties, low toxicity, low water solubility, useful temperature range as a liquid, history of use, and compatibility with (or induction of) cubic and hexagonal phases, are: tocopherols, benzyl benzoate, estragole, eugenol, isoeugenol, linalool, strawberry aldehyde, terpineol, and the following essential oils: balsam of Peru, basil, bay, bois de rose (rosewood), carrot seed, clove-bud, eucalyptus, ginger, grapefruit, hyssop, lemon, mugwort, myrrh gum, bitter orange, oregano, palmarosa, patchouly, peppermint, petitgrain, rosemary, santalwood oil, spearmint, thuja (cedar leaf), thyme, vanilla, and ylang ylang (cananga). Of these, the present inventor has found tocopherols, linalool, and strawberry aldehyde (ethyl methylphenylglycidate) to be the most preferred in the case of injectable products.

Example 18 shows an experimental result which indicates that the exterior-phase concentration of the general anesthetic drug propofol in several cubic phases equilibrated with water is strongly reduced by replacing approximately half of the propofol with alpha-tocopherol. In Examples 19 and 20, propofol formulations of the instant invention in which the same tocopherol-propofol mixture was used in the cubic phase particles were injected intravenously in dogs, and no discomfort on injection was noted in any of the animals. As noted above, the consensus in the art is that the stinging on injection of many propofol formulations is due to the propofol present in the aqueous phase. This underscores the importance of control of oil-water partitioning that is possible in the current invention, by a simple means. The same method is also applicable to other systems containing surfactants or lipids, such as liposomes, coated liquid crystal particle dispersions, microemulsions, and emulsions. It is not necessary that the diluent have any particular affinity for the drug, as illustrated by the examples herein where tocopherol is the diluent, since this compound has no special affinity for propofol (nevertheless, as discussed above, propofol and tocopherol share one structural similarity that is important in the context of this invention). Rather the effect is the mathematical result of the increased ratio of hydrophobic volume to drug mass. As seen by the data in Example 18, increasing the ratio of hydrophobic volume (volume fraction of hydrophobic domains) to drug content (volume fraction of drug) by 50%, or more preferably by 100%, can have a strong effect on the concentration of drug in the exterior phase. Tocopherols are particularly useful as diluents in a wide range of possible systems because of their long hydrophobic chains, low melting points, and safe, non-allergenic nature. While the use of oily diluents is known in the art of emulsions, their use in the context of liposomes and liquid crystal-based dispersions has been virtually unknown, particularly in the field of pharmaceutics, with the exception of certain patent disclosures of the current inventor (U.S. application Ser. No. 10/176,112 and 60/387, 909).

Another surprising finding in the course of preparing the samples reported herein was that the oxidation of propofol over time was strongly reduced by the use of the tocopherol diluent method described above. This could be due to a combination, perhaps a synergistic one, of several factors. The tocopherol itself can act as an antioxidant, and in particular can protect the propofol when it is in the hydrophobic domains of the dispersion. In addition, the reduction of aqueous propofol by the diluent method can reduce the rate of oxidation due to the slower oxidation kinetics in the hydrophobic domains as compared to the aqueous phase, due to higher viscosity and/or lower concentration of oxygen. The second factor would apply even in cases where the diluent were not specifically an antioxidant.

Tonicity Adjustment. In the course of this invention, the inventor has found that soluble amino acids, e.g. glycine, praline, and valine, in particular, are excellent tonicity adjusters for formulations that incorporate surfactants containing polyethyleneoxide (or PEG) polar groups, such as Poloxamers (Pluronics), particularly in the case of propofol formulation. The reasons that soluble, and especially neutral hydrophilic, amino acids are particularly useful in these cases are: 1) they do not suffer from the tendency to precipitate particles incorporating PEGylated surfactant, as do ionic salts; 2) they do not appreciably increase, and in fact they can decrease, the concentration of propofol in the exterior aqueous phase, which as discussed herein is important in reducing burning on injection; and 3) they appear to have the effect of improving the compatibility of the reversed cubic and hexagonal phases with the aqueous phase. Example 18 demonstrates the reduction of aqueous propofol with the addition of glycine to make the dispersion isotonic (about 300 mOsm/L). In contrast, it was found that saccharides which are commonly used to adjust tonicity, such as dextrose, increased aqueous levels of propofol. Even 0.8% sodium chloride had the effect of precipitating Pluronic L-122/deoxycholate particles of the present invention over a period of about one week. Glycine was also discovered to yield a more transparent cubic phase, indicating more perfect long-range order, in these experiments. Glycine and valine and proline were found to have no adverse effects on propofol-containing, L-122 based cubic phase particles of the current invention. Glutamine and asparagine were disruptive of the same formulation. Glycine is used in large amounts (greater than 100 mg/Kg) in injections of the pharmaceutical product Humate-P, and a single dose of the injectable nutritional product Nephramine contains more than 2 grams of the valine, making both especially preferred for parenteral products. Preferred amino acids for this purpose, in decreasing order of preference, are: glycine, alanine, proline, serine, glutamine, valine, asparagine; the acidic, basic, and hydrophobic amino acids are much less preferred (and some of these are not soluble in water to tonicity-adjusting levels), as are sulfur-containing amino acids because of hypersensitivity issues. The amino acids listed as preferred also have a pH-stabilizing effect, and can act as antioxidants to some extent. The use of glycine at levels between about 1 and 3%, and more preferably between about 1.3 and 2.2%, is preferred for adjusting tonicity, unless other components are present that add to the osmolality in which case lower levels can be useful. The synergy between the various functionalities of these amino acids—namely their compatibility with PEG head groups, their positive effect on drug partitioning (at least in the case of phenolic drugs such as propofol), and their tonicity, buffering, and antioxidant activity is particularly important in the case of pharmaceutical products, where the impetus is high to keep the number of components in the formulation to a minimum. Tonicity might also be achieved with the use of zwitterions, including phoshpatidylcholine.

An especially useful method of producing particles of the present invention involves related phases of lower viscosity. In particular, and as illustrated in Example 17 below, it is often the case that when water is removed from a reversed cubic or hexagonal phase, a much lower-viscosity, liquid L2 phase is formed, or in rarer cases a liquid L3 phase. This is, in some cases, merely a reflection of the fact that surfactant head groups require hydration in order for the segregation into hydrophobic and hydrophilic domains to be pronounced enough, energetically speaking, for full-blown liquid crystalline phase behavior to develop. Since the liquid L2 phase is of low viscosity it is much more easily dispersed in water, and after the resulting droplets hydrate with water, they undergo the phase change into the sought-after reversed liquid crystalline phase. This hydration is generally a rapid process because the diffusion times are greatly reduced, assuming a reasonably fine L2-phase droplet size is achieved, preferably less than about 100 microns and more preferably less than about 20 microns. The same charged moiety that induces the charge stabilization in the final liquid crystalline particle dispersion can likewise provide charge stabilization of the liquid droplets in dispersion. Other methods can be used to convert the precursor liquid (usually L2, or in other cases L3 phase) droplets into liquid crystalline phase particles. These include, for example, incorporating a low-partition-coefficient compound into the liquid crystal causing it to liquify, where the low $K_{ow}$ implies that the compound will preferentially leave the liquid droplets upon dispersing, inducing the liquid to revert to a liquid crystal as a particle. Such a compound can easily be found simply by adding sufficient quantity of a low-$K_{ow}$ compound to a liquid crystal until the liquid crystal liquifies, which is not a difficult endeavor in view of the typically small composition range of reversed liquid crystalline phases.

Stability studies reported in Example 22 demonstrate that particles of the instant invention are stable long-term in dispersion, with very little aggregation or particle size growth over time, as shown by dynamic light scattering measurement, which is well known to be very sensitive to particle aggregation. It should be noted that this stands in contrast with the cubic gel particles of U.S. Pat. No. 6,071,524 which are in fact designed to aggregate at the surface of the oil droplets in that invention. Stability studies with particle sizing results over time were not provided in U.S. Pat. No. 6,071,524.

The following examples illustrate the present invention but are not to be construed as limiting the invention.

EXAMPLES

Example 1

A reversed cubic phase containing the anesthetic propofol was first prepared by mixing 0.952 grams (gms) of propofol (obtained from Albemarle Corporation), 1.308 gm of distilled water (all references to water in this section mean distilled water), and 2.756 gm of the surfactant Pluronic L122 (obtained from Ethox Corporation). After thoroughly mixing this composition, it was checked that the material was optically isotropic and of high viscosity. Next, 0.319 gm of the anionic surfactant sodium docusate (also known as Aerosol OT, or simply AOT) was dissolved in 100 ml of water, Then 1.088 gm of the cubic phase was added to a 100 ml beaker containing 20 ml of the surfactant solution, and the mixture homogenized using a Brinkmann PT 10/35 homogenizer, after which the homogenized dispersion was microfluidized in a Microfluidics Model 110 L high-pressure microfluidizer, using three runs of 30 seconds each at approximately 10,000 psi. Observation in an Olympus BHC phase contrast microscope demonstrated that a particle size on the order of 300 nanometers (nm) had been achieved. The dispersion was then analyzed using a Beckman-Coulter DELSA 440SX for Doppler Electrophoretic Light Scattering Analysis, set in zeta potential measurement mode.

Figure 3:
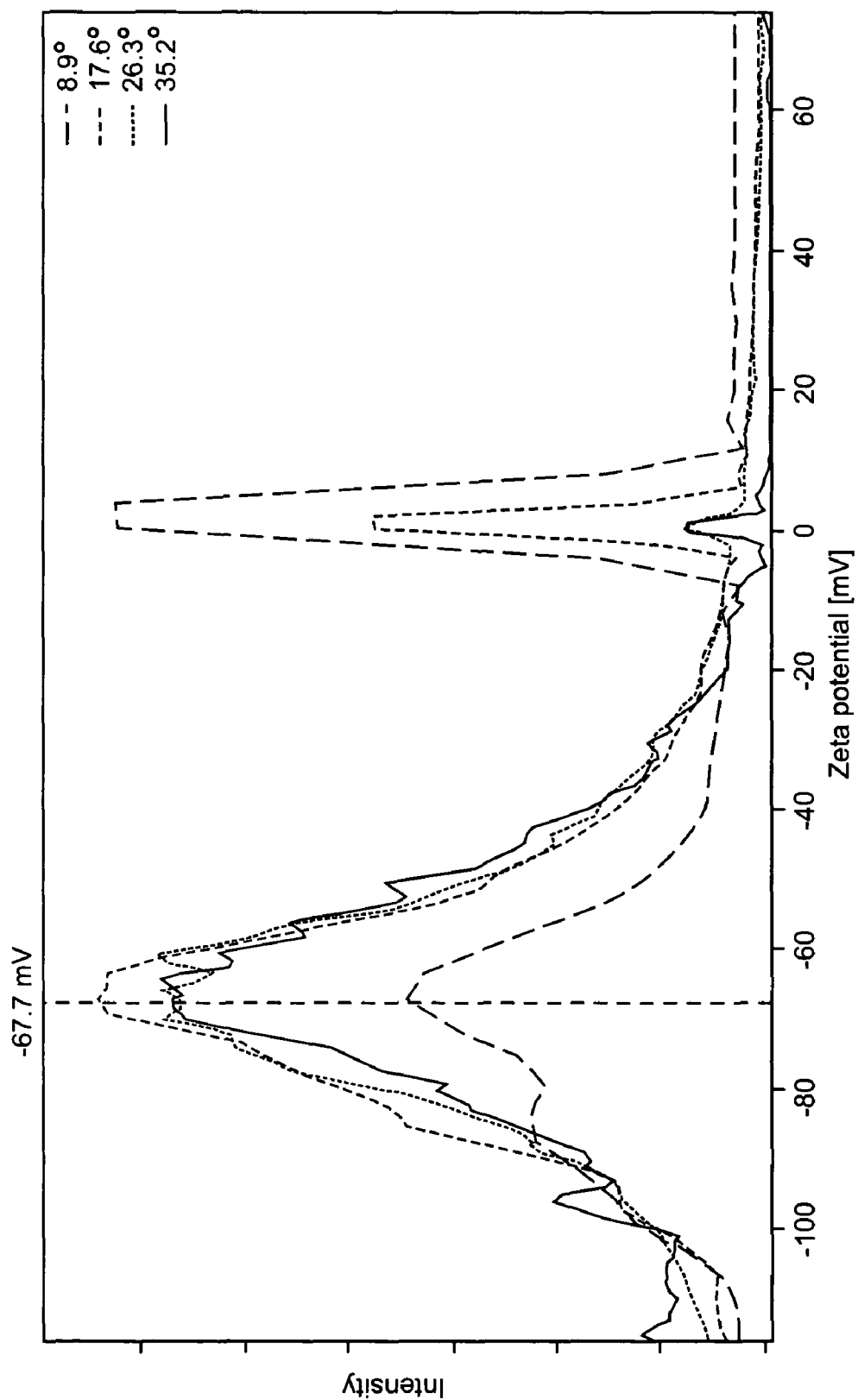
FIG. 3 shows the resulting measured zeta potential distribution, using three angles of measurement for the dispersion described in Example 1.

FIG. 3 shows the resulting measured zeta potential distribution, using three angles of measurement. At all three angles, the distribution is centered around −67 mV, which is a strong enough zeta potential to produce a stable dispersion. It should be noted that although there is a spread to the distribution, significant contributions to this reported spread come from instrumental broadening, and diffusional broadening. Therefore the distribution is in fact significantly narrower than indicated. Particularly with this in mind, the fraction of particles with a zeta potential less than 30 mV in magnitude is quite small.

The ratio of surfactant (docusate) to cubic phase in this Example was 0.06:1, and a stable dispersion resulted, with an average zeta potential of −67 mV. When this ratio was decreased to 0.02:1, keeping everything else constant, the average zeta potential moved to approximately −20 mV, and that dispersion was not stable.

Example 2

The general anesthetic and hypnotic agent propofol, in the amount 0.57 grams, was combined with 0.78 gm sterile water and 1.65 gm of Pluronic L122 (in which the weight fraction of polyoxyethylene chains is 20%), working in a laminar flow hood. After mixing this to form a reversed cubic phase, 0.105 gm of sodium deoxycholate were dissolved in 40 ml of sterile water. An amount 2.1 gm of the cubic phase were then dispersed in the 40 ml of solution, first using the Brinkmann homogenizer, then using the Microfluidics microfluidizer for a total of 15 minutes of high-pressure microfluidization. The dispersion, referred to below as "Lyotropic/PF1", was filtered with a 0.8 micron syringe filter before using in the animal tests described in Example 4 below.

Figure 4:
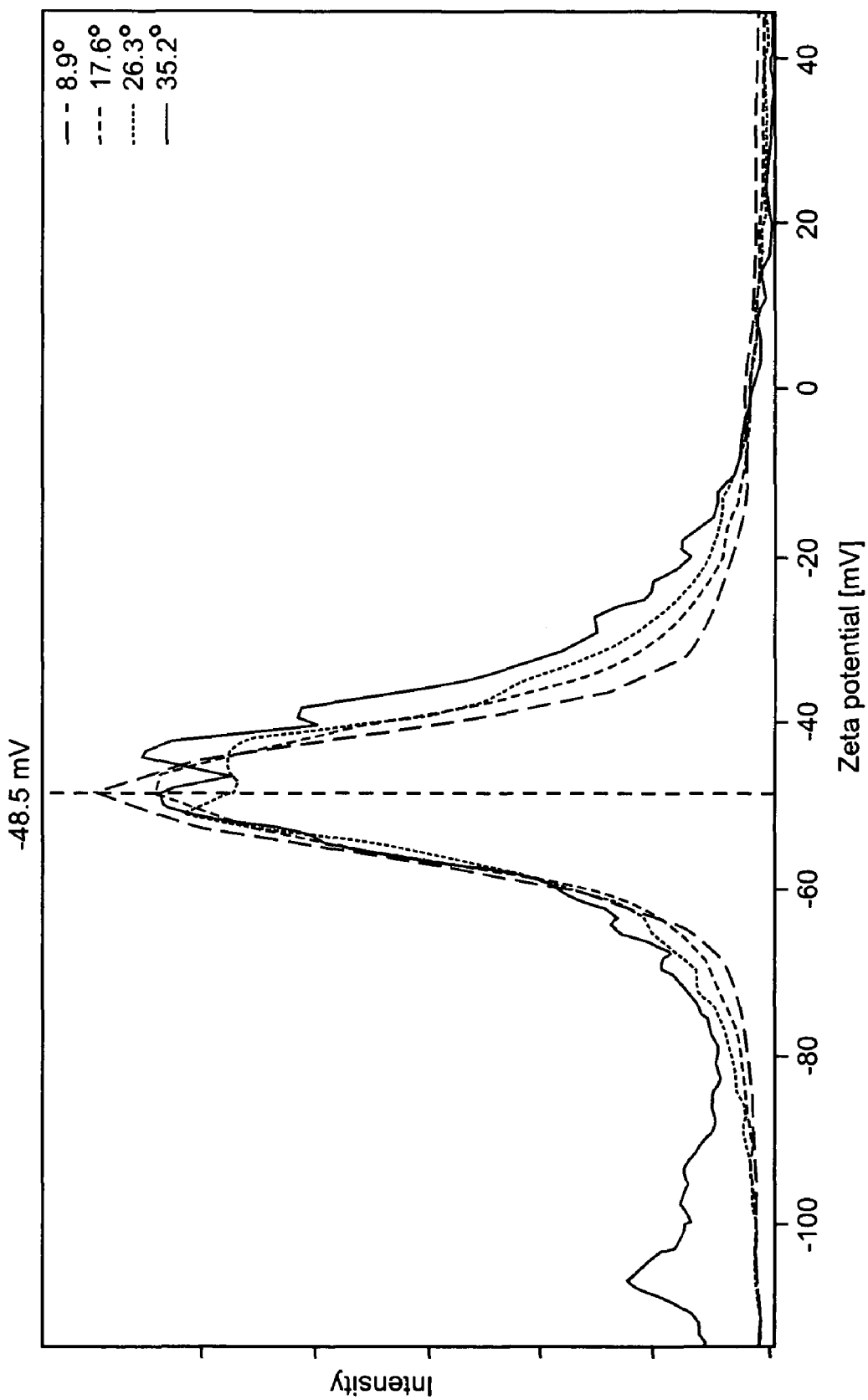
FIG. 4 shows the zeta potential distribution measured for a dispersion in the presence of excess water described in Example 2.

FIG. 4 shows the zeta potential distribution measured for this dispersion. The average zeta potential, namely about −48 mV, is greater in magnitude than 30 mV and thus consistent with stabilization due primarily to the surface potential.

Figure 5:
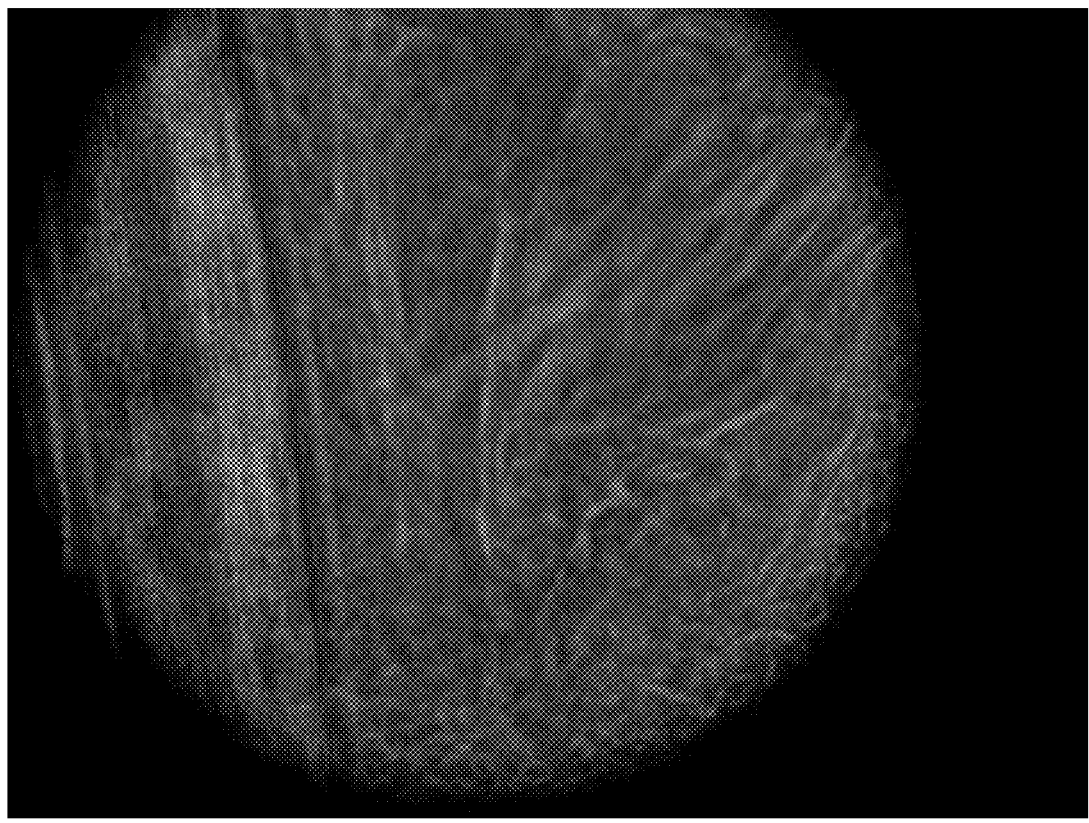
FIG. 5 shows the phase behavior in the presence of excess water as analyzed with a polarizing optical microscope for the dispersion described in Example 2.

A mixture was also prepared with only 1 ml of water but the same amount of sodium deoxycholate. Thus, all the ratios were the same as in the previous paragraph, except the amount of water. The purpose of this is to check the phase behavior in the presence of excess water (this is enough to give an excess), but without the dispersing/diluting effect that comes with the normal 20:1 water:cubic phase ratio. This means that if any L3 or lamellar phase were present, while it might be difficult to detect in the dilute dispersion, it would be far easier to detect in this concentrated form. This was analyzed in an Olympus BHC polarizing optical microscope, and the result shown in FIG. 5. On the left is a thick line of birefringence, which is a single strand of hair, deliberately placed in the field of view to show what a birefringent material would appear like under these optical/photographic conditions. The contrast clearly shows that material of this invention is non-birefringent. Neither was there birefringence when the sample was sheared between glass and coverslip, showing that there is no L3 present. In addition, when the sample was centrifuged, there did not appear to be any signs of a separate L3 in the centrifuged sample, rather it appeared to be simply a mixture of cubic phase plus excess aqueous solution.

Example 3

Propofol, in the amount 0.57 grams, was combined with 0.78 gm sterile water and 1.65 gm of Pluronic P123 (in which the weight fraction of polyoxyethylene chains is 30%), working in a laminar flow hood. After mixing this to form a reversed cubic phase, 0.105 gm of sodium deoxycholate were dissolved in 40 ml of sterile water. An amount 2.1 gm of the cubic phase were then dispersed in the 40 ml of solution, first using the Brinkmann homogenizer, then using the Microfluidics microfluidizer for a total of 15 minutes of high-pressure microfluidization. The dispersion, referred to below as "Lyotropic/PF4" was filtered with a 0.8 micron syringe filter before using in the animal tests described in Example 4 below. DELSA analysis shown a unimodal zeta potential distribution centered at approximately −36 mV.

Example 4

In this Example, rats were dosed with the formulations reported above in Examples 2 and 3, and these formulations were found to outperform a currently marketed, emulsion-based formulation of propofol, yielding a faster return to normal awareness after anesthesia, in contrast to the slower return noted for the marketed brand. A total of 18 Sprague Dawley rats were administered Lyotropic/PF1, Lyotropic/PF4 or Propoflo® (the commercially available propofol formulation) via the lateral tail vein once at dose levels ranging from 0.5 to 12 mg/kg in an up-down fashion. The rats were housed in stainless steel cages with wire mesh floors suspended over flush pans and identified by a unique number marked on their tail with indelible ink in addition to a cage card inscribed with the animal number, study number, group number and color-coded dose level. The animals were maintained in an isolated temperature (16-23 C) and humidity (53%-71%) controlled animal room with a filtered air supply (10-15 air changes/hour) and cycled lighting (12 hours daily). PMI Certified Rodent Diet (5002) and tested tap water were available ad libitum. Food was withheld overnight prior to dosing. Rats used in this study were acclimated to laboratory conditions for at least 5 days prior to animal phase initiation. The rats were selected on the basis of pretest body weight and general appearance and randomly assigned to the following groups:

| Group Number | Test Article | Doses mg/kg | Dose Conc. mg/mL | No. of Rats/Dose Level |
|---|---|---|---|---|
| CBF1 | Lyotropic/PF1 | 0.5, 1, 2, 4, 8 | 1 or 10* | 2 |
| CBF3 | Propoflo ® | 4, 8 | 10 | 2 |
| CBF4 | Lyotropic/PF4 | 2, 4, 8 | 10 | 2 |

*For rats dosed at 0.5, 1 and 2 mg/mL, the test article was diluted with Sterile Water for Injection for a final dose concentration of 1 mg/mL. The final dose concentration for rats dosed at 4 and 8 mg/mL was 10 mg/mL.

Body weights were obtained just prior to dose administration and were used as the basis for dosing. The animals were observed immediately postdose and continuously up through 30 minutes, and again at approximately 1, 2 and 24 hours postdose for general health, physical appearance and for signs of clinical effect, including behavioral changes. Parameters for evaluation included postdosing observations and gross observations at necropsy.

No mortality occurred during the 24-hour postdosing observation period. Relevant signs of effect included ataxia, comatose, decreased activity, and squinting of the eyelid(s), which were all resolved by 24 hours postdosing. In most cases, the time of the comatose condition was rapid following intravenous injection and generally increased in a dose-dependent manner. Gross necropsy observations revealed no remarkable findings. In particular, no signs of pulmonary emboli were found in any of the test animals, including those treated with the cubic phase dispersion formulations.

Significantly, the animals dosed with Lyotropic/PF1 appeared, to an observer trained in anesthesiology, to emerge from the coma with greater clarity and "clearheadedness" than the animals dosed with Propoflo®. Without wishing to be bound by theory, it is believed that this was due to the integration of the uncoated reversed cubic phase vehicle with biomembrane structures in the body, resulting in the elimination of the vehicle as a "depot", or reservoir, for drug. In contrast, the marketed emulsion formulation is believed to suffer from effects due to a lingering reservoir effect from the oil droplets.

The Body Weight and Dosing Records (Table 1), Individual Postdose Clinical Signs (Table 2) and Time of Comatose Condition (Table 3) are given below.

TABLE 1

Body Weight and Dosing Records

| Animal No. Prefix: CBF | Body Weight (g) | Dose (mg/kg) | Dose Concentration (mg/mL) | Dose Volume (mL/kg) |
|---|---|---|---|---|
| Lyotropic/PF1 | | | | |
| 1M1 | 259.2 | 0.5 | 1 | 0.5 |
| 1F17 | 222.5 | 0.5 | 1 | 0.5 |
| 1M5 | 265.5 | 1 | 1 | 1 |
| 1F21 | 221.1 | 1 | 1 | 1 |
| 1M9 | 265.4 | 2 | 1 | 2 |
| 1F25 | 231.9 | 2 | 1 | 2 |
| 1M13 | 273.1 | 4 | 10 | 0.4 |
| 1F29 | 235.8 | 4 | 10 | 0.4 |
| 1M33 | 299.1 | 8 | 10 | 0.8 |
| 1F34 | 203.2 | 8 | 10 | 0.8 |
| Propoflo ® | | | | |
| 3M3 | 237.7 | 4 | 10 | 0.4 |
| 3F19 | 220.1 | 4 | 10 | 0.4 |
| 3M7 | 253.8 | 8 | 10 | 0.8 |
| 3F23 | 222.5 | 8 | 10 | 0.8 |
| Lyotropic/PF4 | | | | |
| 4M12 | 275.3 | 2 | 10 | 0.2 |
| 4F28 | 229.2 | 2 | 10 | 0.2 |
| 4M16 | 271.8 | 4 | 10 | 0.4 |
| 4F32 | 242.0 | 4 | 10 | 0.4 |
| 4M35 | 283.3 | 8 | 10 | 0.8 |
| 4F36 | 215.3 | 8 | 10 | 0.8 |

TABLE 2

Individual Postdose Clinical Signs

| Animal No. Prefix: CBF | Test Article | Dose (mg/kg) | 0-30 Min Post-dosing | 1 Hour Postdosing | 2 Hours Postdosing | 24 Hours Postdosing* |
|---|---|---|---|---|---|---|
| 1M1 | Lyotropic/PF1 | 0.5 | DA, ES | NR | NR | NR |
| 1F17 | Lyotropic/PF1 | 0.5 | DA, ES | NR | NR | NR |
| 1M5 | Lyotropic/PF1 | 1 | DA | NR | NR | NR |

TABLE 2-continued

Individual Postdose Clinical Signs

| Animal No. Prefix: CBF | Test Article | Dose (mg/kg) | 0-30 Min Post-dosing | 1 Hour Postdosing | 2 Hours Postdosing | 24 Hours Postdosing* |
|---|---|---|---|---|---|---|
| 1F21 | Lyotropic/PF1 | 1 | DA | NR | NR | NR |
| 1M9 | Lyotropic/PF1 | 2 | DA | NR | NR | NR |
| 1F25 | Lyotropic/PF1 | 2 | DA | NR | NR | NR |
| 1M13 | Lyotropic/PF1 | 4 | CT, DA | NR | NR | NR |
| 1F29 | Lyotropic/PF1 | 4 | CT, DA | NR | NR | NR |
| 1M33 | Lyotropic/PF1 | 8 | AT, CT | NR | NR | NR |
| 1F34 | Lyotropic/PF1 | 8 | AT, CT | NR | NR | NR |
| 3M3 | Propoflo ® | 4 | AT | NR | NR | NR |
| 3F19 | Propoflo ® | 4 | AT,CT | NR | NR | NR |
| 3M7 | Propoflo ® | 8 | AT, CT | NR | NR | NR |
| 3F23 | Propoflo ® | 8 | AT, CT | NR | NR | NR |
| 4M12 | Lyotropic/PF4 | 2 | DA | NR | NR | NR |
| 4F28 | Lyotropic/PF4 | 2 | DA | NR | NR | NR |
| 4M16 | Lyotropic/PF4 | 4 | AT, DA | DA | NR | NR |
| 4F32 | Lyotropic/PF4 | 4 | AT, CT | NR | NR | NR |
| 4M35 | Lyotropic/PF4 | 8 | AT, CT, DA | NR | NR | NR |
| 4F36 | Lyotropic/PF4 | 8 | AT, CT | NR | NR | NR |

Key to observations:
AT = Ataxia
CT = Comatose
DA = Decreased activity
ES = Eyelid(s) squinting
NA = Not applicable
NR = Not remarkable
*Just prior to necropsy

TABLE 3

Length of Comatose Condition

| Animal No. Prefix: CBF | Test Article | Dose (mg/kg) | Time of Comotose (min) |
|---|---|---|---|
| 1M13 | Lyotropic/PF1 | 4 | 3 |
| 1F29 | Lyotropic/PF1 | 4 | 4 |
| 1M33 | Lyotropic/PF1 | 8 | 4.5 |
| 1F34 | Lyotropic/PF1 | 8 | 5.5 |
| 3F19 | Propoflo ® | 4 | 1 |
| 3M7 | Propoflo ® | 8 | 5 |
| 3F23 | Propoflo ® | 8 | 5.5 |
| 4M35 | Lyotropic/PF4 | 8 | 4 |
| 4F36 | Lyotropic/PF4 | 8 | 8 |
| 4F32 | Lyotropic/PF4 | 4 | 2 |

Example 5

Figure 6:
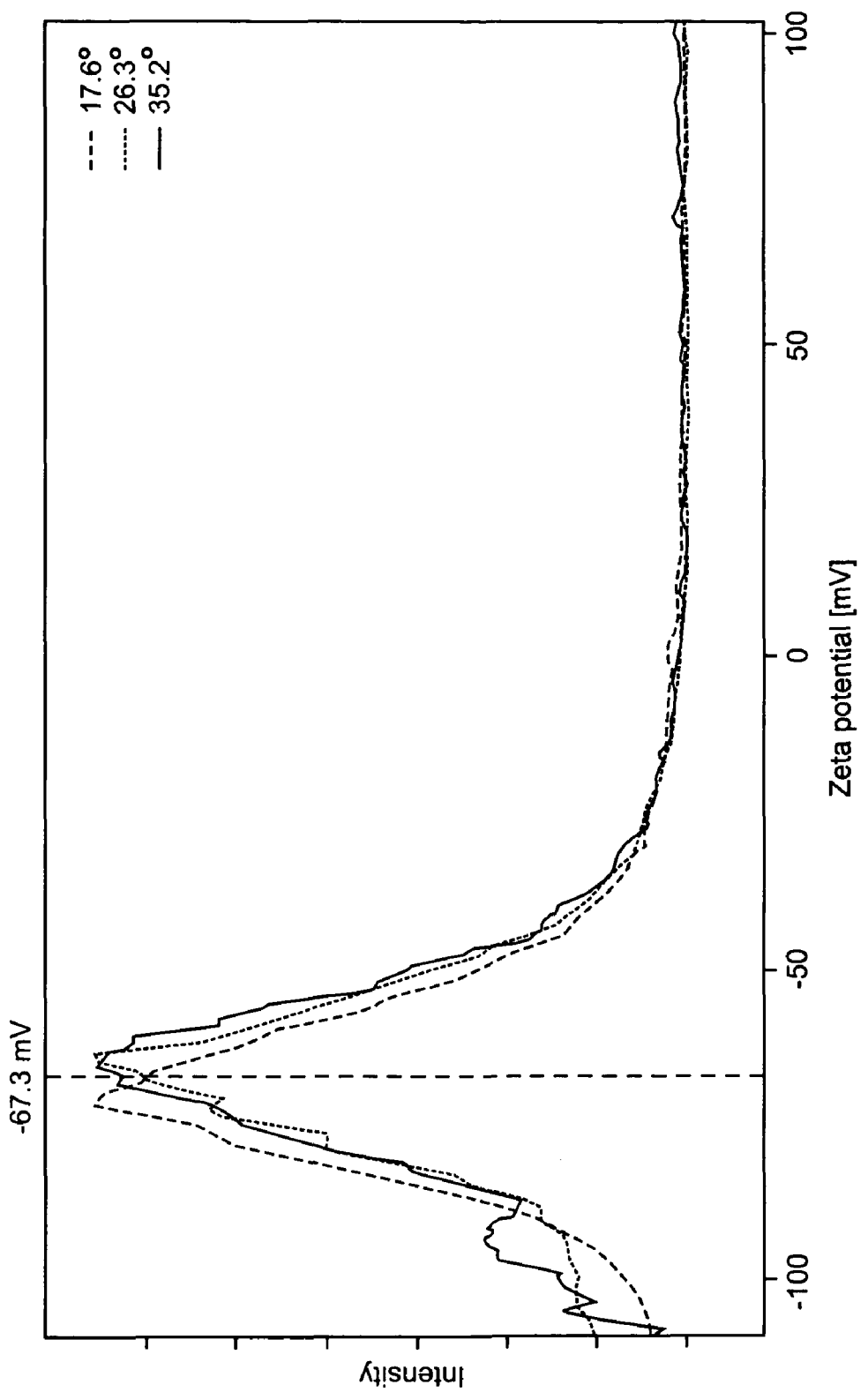
FIG. 6 shows the zeta potential data for the dispersion described in Example 5.

A reversed cubic liquid crystalline phase was prepared by thoroughly mixing 0.962 gm of propofol, 0.706 gm water, and 1.329 gm of soy phosphatidylcholine (from Avanti polar lipids). An amount 1.002 gm of this cubic phase was placed in a 100 ml beaker containing 20 ml of aqueous sodium docusate (Aerosol OT), wherein the ratio of docusate to cubic phase was 0.06:1. The mixture was homogenized at high speed for 45 seconds, then microfluidized for 6 minutes, producing a fine dispersion, with a substantial submicron population. This was analyzed with the DELSA instrument and found to have an average zeta potential of about −67 mV, as shown in FIG. 6. It should be noted that under the conditions (in particular, pH) used, the phosphatidylcholine/propofol/water cubic phase would, as in the previous Examples, be substantially uncharged, so that the docusate is required for the attainment of a charge-stabilized cubic phase particle dispersion. Indeed, it is impossible to disperse this cubic phase without the use of a charged, bilayer-associated compound even at the highest shear rates possible with this instrumentation. Quickly after any attempt, no matter how vigorous, to disperse this cubic phase, the cubic phase material agglomerates back into macroscopic clumps. All of the components (except the drug) in this formulation are on the FDA list of approved excipients for injectable products.

Example 6

Figure 7:
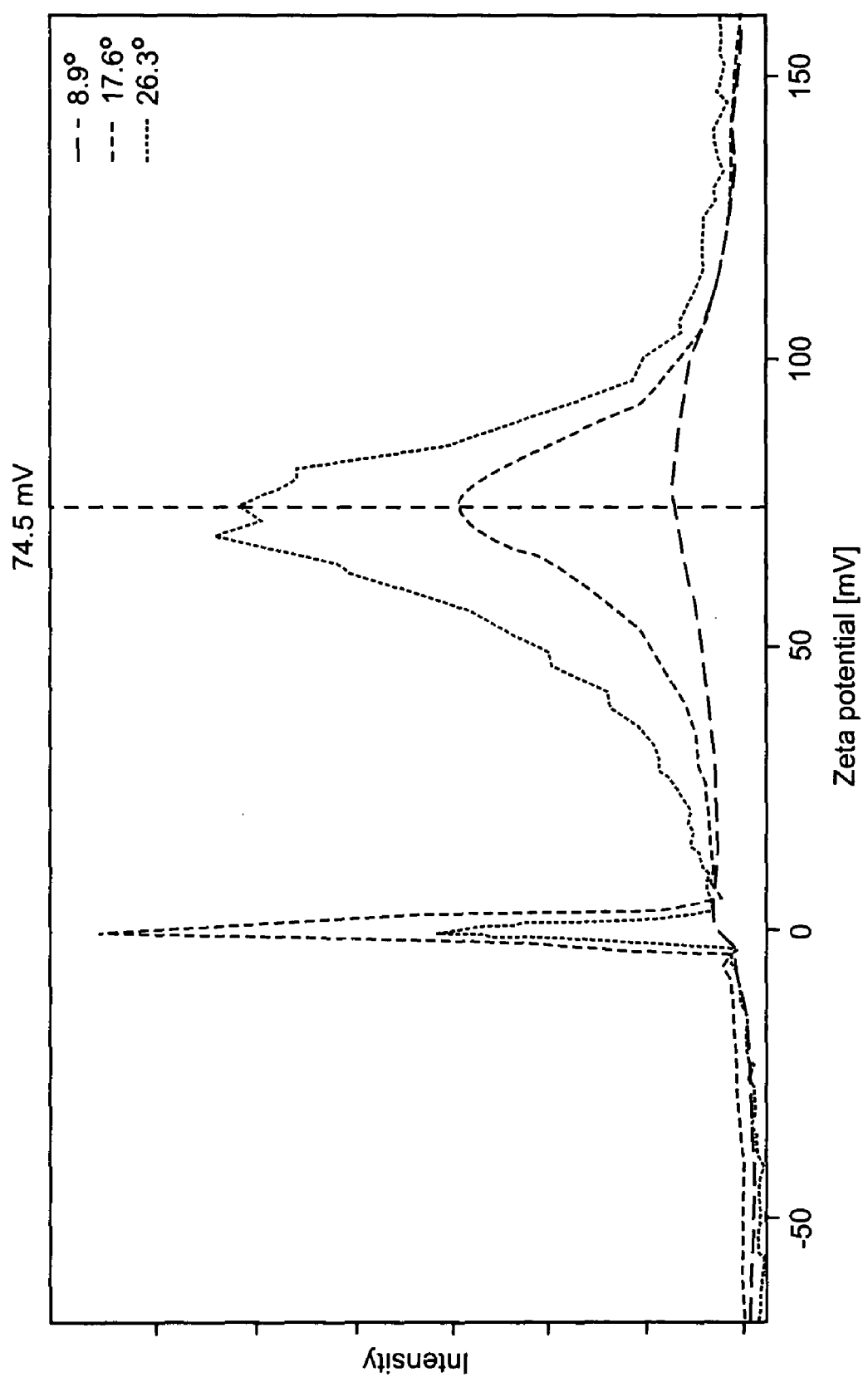
FIG. 7 shows the zeta potential data for the dispersion described in Example 6.

Another 1.002 gm of the cubic phase from Example 5 was dispersed in 20 ml of a solution of benzalkonium chloride using the same methodology as in Example 5. The average zeta potential was then measured and found to be about +74 mV, as shown in FIG. 7.

Example 7

Figure 8:
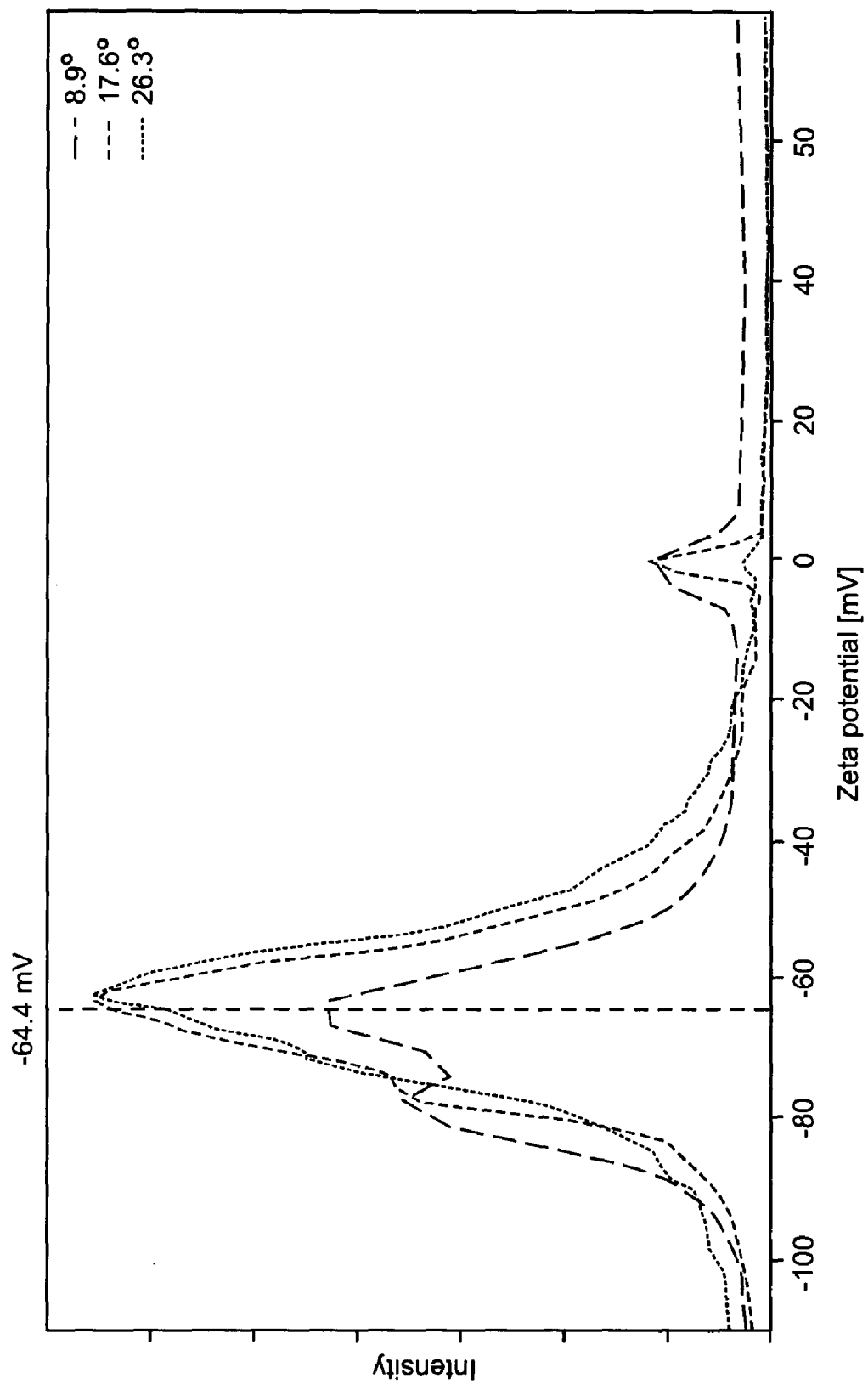
FIG. 8 shows the zeta potential data for the dispersion described in Example 7.

The local anesthetic bupivacaine, in its free base form, and in the amount 0.176 gm, was combined with 0.700 gm linalool, 0.333 gm santalwood oil, 1.150 gm water, and 2.65 gm of the surfactant Pluronic L122. The resulting cubic phase is thus composed of excipients of very low toxicity; even santalwood oil has been shown to be of low toxicity by injectable routes (though it is not strictly speaking approved for use in injectable products). Using the methodology of the previous Examples, this cubic phase was dispersed using sodium docusate (at a 0.06:1 ratio), and the zeta potential measurement taken. FIG. 8 shows the result, which indicates a distribution centered around −64 mV, and nearly all particles more negative than −30 mV.

Example 8

Figure 9:
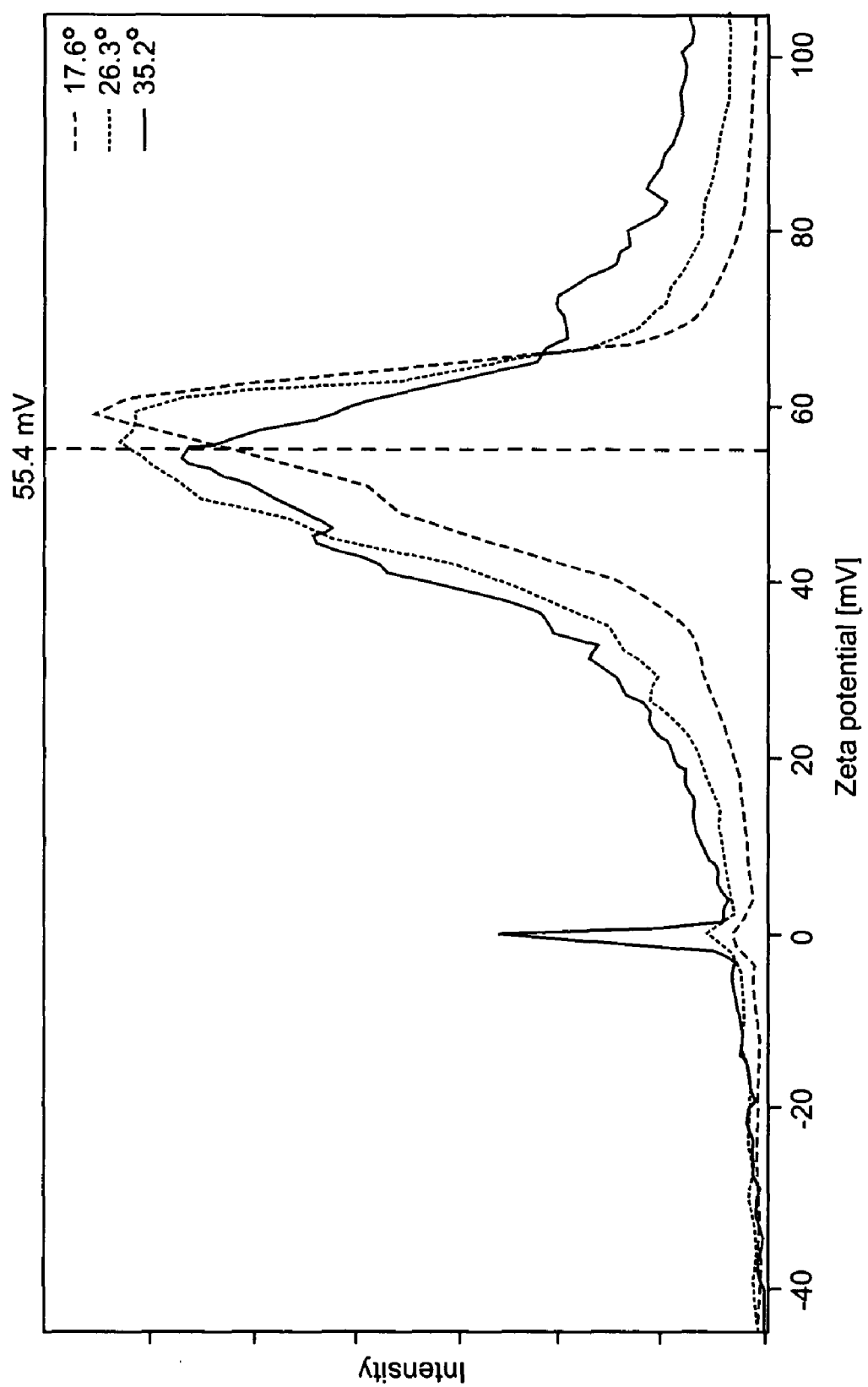
FIG. 9 shows the zeta potential data for the dispersion described in Example 8.

The cubic phase from Example 7 was dispersed, using similar physical methods, using the cationic surfactant benzalkonium chloride. The resulting zeta potential distribution, shown in FIG. 9, was centered around +55 mV, for the dispersion of charged-stabilized particles.

Example 9

A cubic phase containing the active vitamin E was prepared by mixing 1.12 gm of vitamin E (alpha-tocopherol), 1.593 gm of soy phosphatidylcholine, and 0.788 gm of water. This was dispersed using benzalkonium chloride, and a zeta potential average of roughly +70 mV was recorded.

Example 10

The same cubic phase as in Example 9 was stirred vigorous together with one-tenth its weight in sodium dantrolene, a skeletal muscle relaxant. This was then dispersed in aqueous benzalkonium chloride, with a 20:1 ratio of water to cubic phase, and a 0.06:1 ratio of surfactant to cubic phase. This was homogenized at high speed for 3 minutes.

Zeta potential is particularly meaningful in this case, since the drug is anionic, whereas the dispersed cubic phase (as in Example 9) is cationic. Therefore, if "free" dantrolene is present then a peak will appear with a negative zeta potential, together with the peak from the cationic-stabilized particles, indicating that particles of this invention have not been produced.

Figure 10:
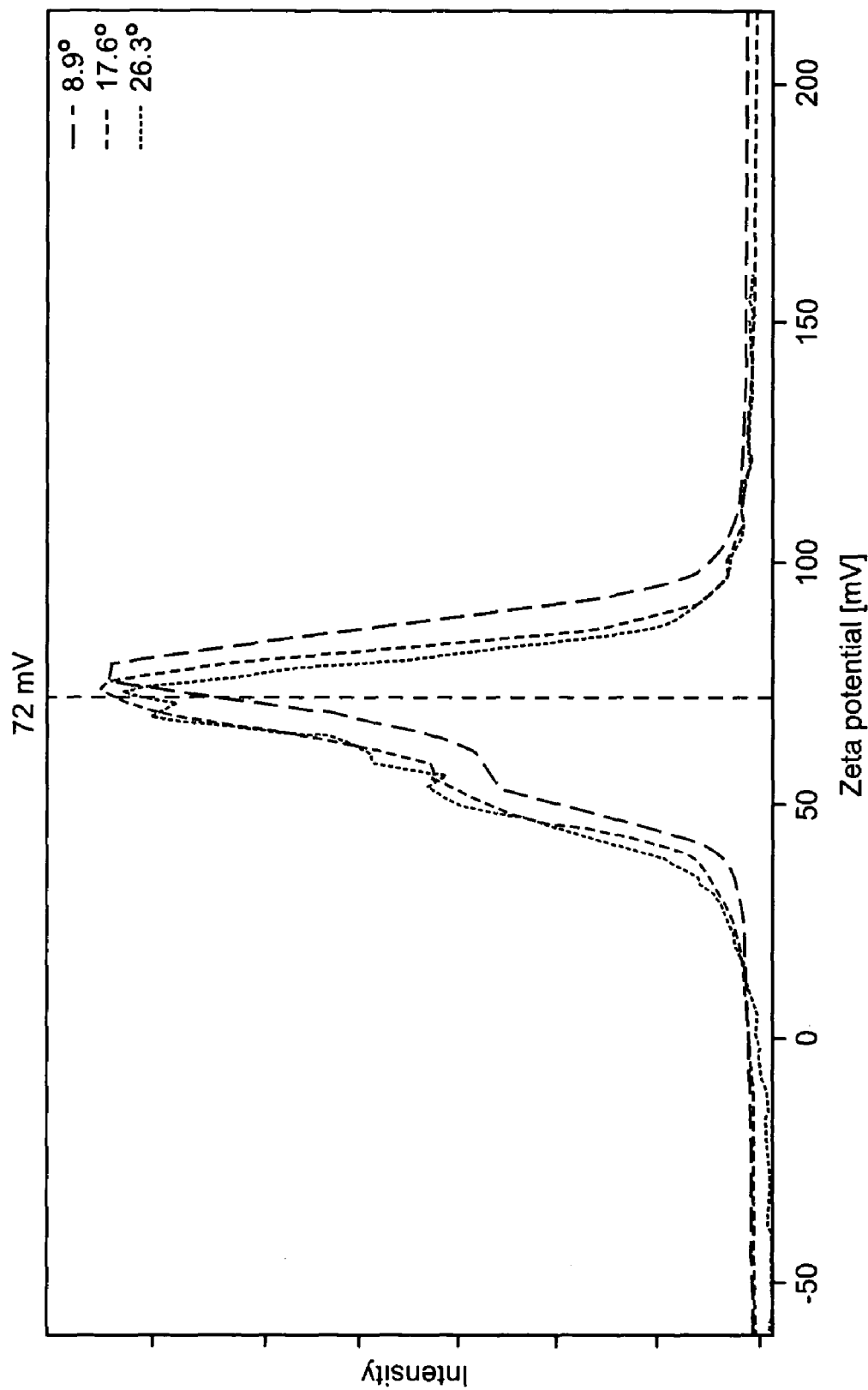
FIG. 10 shows the zeta potential data for the dispersion described in Example 10.

In fact, the strongly-colored (from the dantrolene sodium) dispersion was analyzed with the DELSA, and no peak was found at negative zeta potential. FIG. 10 shows the analysis, with a single peak (at all four angles) centered at +72 mV. Thus, particles of the present invention were indeed produced, with nanosized crystals of the poorly-soluble skeletal muscle relaxant stabilized by their being embedded in a cationically-stabilized cubic phase particle of the current invention.

Figure 11:
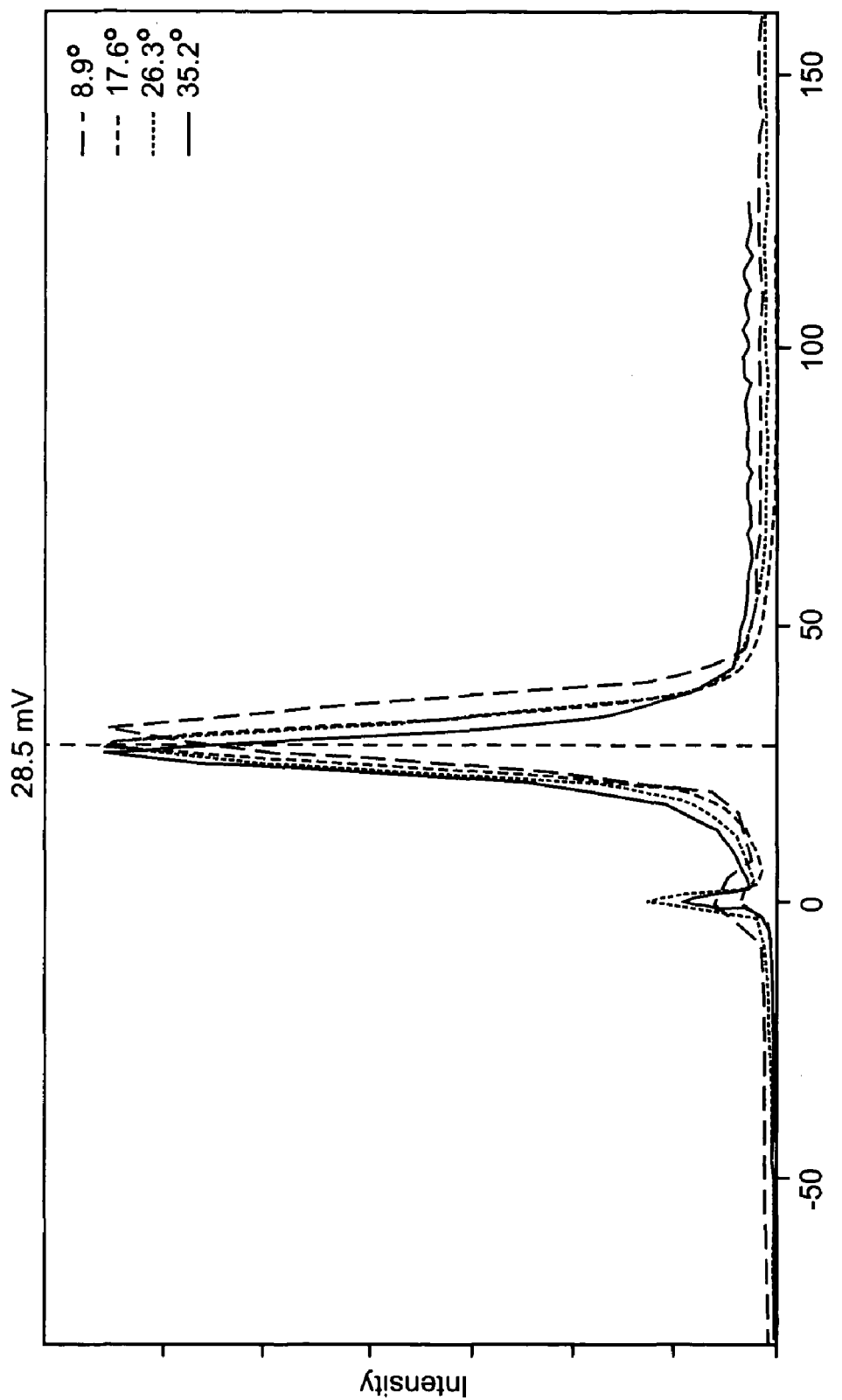
FIG. 11 shows the zeta potential data for dantrolene sodium with only benzalkonium (i.e. no cubic phase is present) as described in Example 10.

An attempt to disperse dantrolene sodium with only the benzalkonium chloride, not using the cubic phase or any other liquid crystal, was made in order to evaluate the importance of the cubic phase in this Example. Thus, dantrolene sodium was dissolved in the aqueous phase at the same concentration, resulting in a 0.06:1 ratio of surfactant to dantrolene sodium, and the same homogenization protocol was applied. The DELSA measurement, shown in FIG. 11, clearly shows a much smaller zeta potential than in the case where the cubic phase was used. This greatly increased charge in the case of the cubic phase particle is probably related to the much higher benzalkonium loading possible with the cubic phase (as expressed at the particle surface) as compared to the dantrolene sodium surface.

Dantrolene sodium is presently used in the treatment of malignant hyperthermia, a life-threatening, crisis situation. The currently marketed formulation must be reconstituted one vial at a time, with as many as 36 vials being required for a single treatment. Patient deaths have been reported caused by the physician being unable to reconstitute and inject this many vials during the mounting MH crisis. The present invention may provide a means by which a stable, concentrated dispersion of the drug could be injected in place of the current formulation. While other methods of stabilizing nanocrystals of compounds such as dantrolene are available, the current invention can have advantages over these in cases where the absorption-enhancing properties of the current invention are desirable. All of the components of this formulation are pharmaceutically-acceptable for intravenous injection.

Example 11

Figure 12:
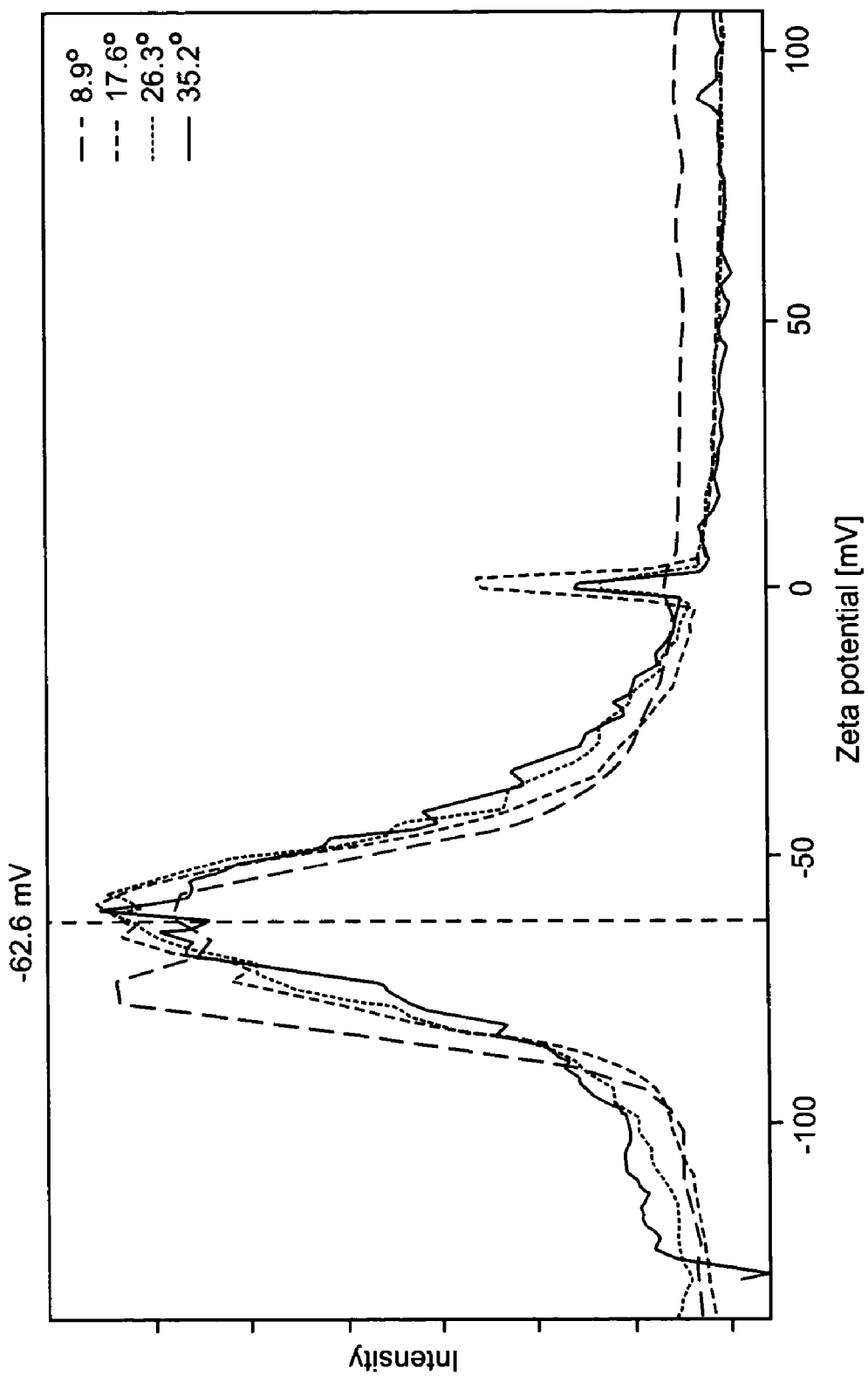
FIG. 12 shows the zeta potential data for the dispersion described in Example 11.

An amount 0.999 grams of the L122/propofol/water cubic phase used in Example 1 was dispersed in a solution of sodium dodecylsulfate (SDS), at an SDS:cubic phase ratio of 0.06:1. This produced a stable dispersion of microparticles with a zeta potential centered at approximately −63 mV, as shown in FIG. 12. SDS is not only a very low toxicity surfactant, which is approved for use in injectable products, but is also one of the most, if not the most, well-studied and characterized surfactants available.

Example 12

Figure 13:
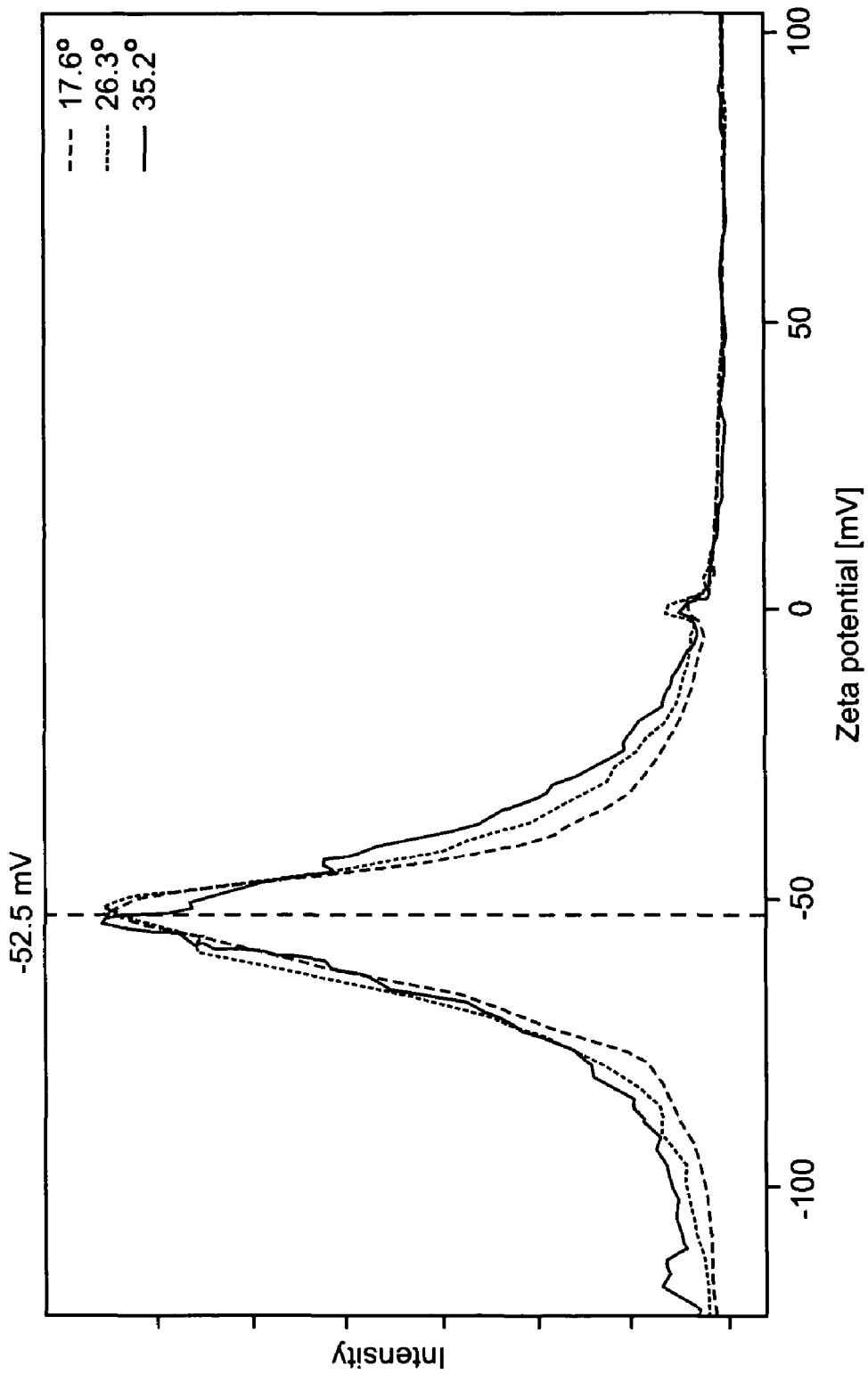
FIG. 13 shows the zeta potential data for the dispersion described in Example 12.

The antineoplastic drug paclitaxel, in the amount 40 mg, was combined with 0.372 gm of santalwood oil and 0.725 gm of strawberry aldehyde, then heated to dissolve the paclitaxel. This was then combined with 1.855 gm of Pluronic L122 (HLB=4) and 0.905 gm of water, and mixed to form a reversed cubic phase. This was then then dispersed in an aqueous solution of sodium docusate at a docusate:cubic phase ratio of 0.06:1, by homogenizing at high speed for 30 seconds, then microfluidizing for 1.5 minutes, and finally centrifuging for 5 minutes in a table-top centrifuge at about 5,000 rpm. DELSA analysis (using a current of 0.18 mA, and a frequency shift of 500 Hz) then indicated a zeta potential distribution centered around −53 mV, as shown in FIG. 13. This cremophor-free formulation of paclitaxel could be well-suited for a number of routes of administration, including bladder instillation, intraperitoneal, peroral, or possibly by injection.

Example 13

A reversed cubic phase containing the anesthetic propofol was first prepared by mixing 0.9501 grams of propofol (obtained from the Albemarle Corporation), 1.2970 gm of distilled water, and 2.7575 gm of the surfactant Pluronic P-123 (a poloxamer surfactant obtained from the BASF Corporation). After thorough mixing, the composition was checked to ensure that it had high viscosity and was optically isotropic. It was then loaded into a 10 mL disposable syringe to facilitate weighing of a 1 gm sample. In another beaker, 0.3192 gm of Aerosol OT (AOT, also called docusate sodium) were dissolved in 100 mL of distilled water. A stir bar was placed in the beaker and the solution was stirred for 1 hour using a Fischer Thermix Model 210T. An amount of 1.0199 gm of the cubic phase was then added to the solution of AOT and water in an amount equivalent to 0.0638 gm AOT and 20.0 gm of distilled water. This resulted in a 0.06:1 surfactant to cubic phase ratio and a 20:1 distilled water to cubic phase ratio. The mixture was homogenized using a Brinkman PT 10/35 homogenizer on high for 20 seconds. The homogenized dispersion was then microfluidized with a Microfluidics M110L for 3 runs, each of which lasted for 30 seconds. Next, the dispersion was collected in a test tube and centrifuged for 2 minutes using a tabletop centrifuge. The dispersion was viewed under an Olympus BHC microscope to check for particle appearance and size.

Figure 14:
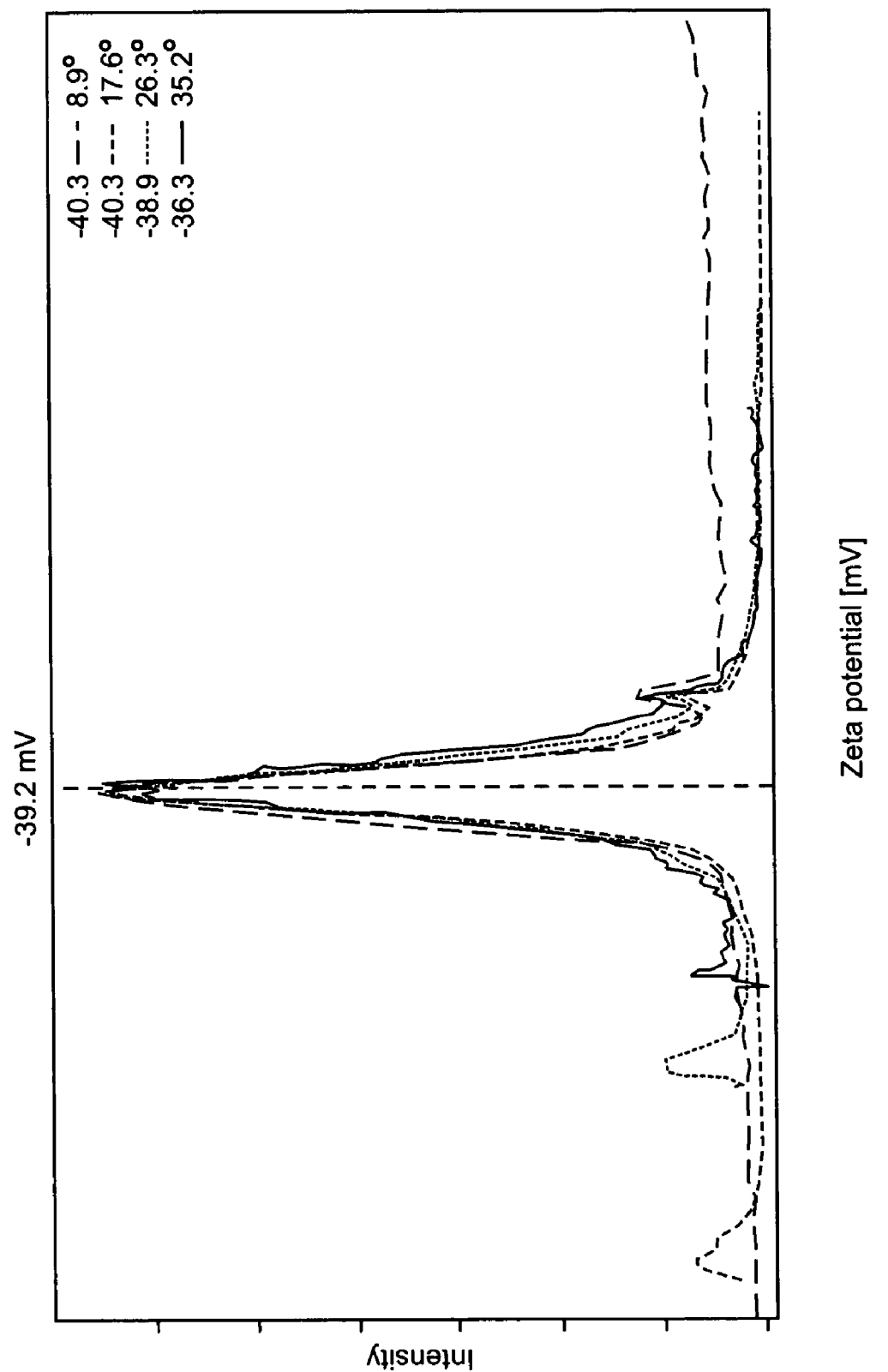
FIG. 14 shows the zeta potential data for the dispersion described in Example 13.

The dispersion was then analyzed by using the Beckmann-Coulter DELSA 440SX for Doppler Electrophoretic Light Scattering Analysis, with electrophoretic mobilities converted to zeta potentials by the standard equations, as seen in FIG. 14. Four scattering angles of measurement were reported, with the distribution in each case centered around negative 39 mV. This electrophoretic mobility analysis was run at a frequency shift, as per the Beckmann-Coulter DELSA methodology, of 500 Hz, with a runtime of 180 seconds. Docusate appears on the 1996 FDA's Inactive Ingredients Guide as approvable for use in injectable products.

Example 14

Using methods similar to those employed in preparing Example 13, an amount of 1.0135 grams of the cubic phase identical to that from Example 13 were added to an equivalent of 0.0638 gm Sodium Dodecyl Sulfate (SDS) (obtained from the EM Science Corporation) and 20.0 gm of distilled water as described in Example 13.

Again, using similar methods to Example 13, the dispersion was homogenized, microfluidized, and analyzed under the microscope. The zeta potential was found to be negative 41 mV, as measured from four angles at 500 Hz for 180 seconds. It should be noted that SDS has been used in the injectable pharmaceutical product Proleukin.

Example 15

Again, using methods similar to those employed in Example 13, an amount of 1.0001 grams of the cubic phase identical to that from Example 13 were added to an equivalent 0.0638 gm of Benzalkonium Chloride (obtained from the Sigma Corporation) and 20.0 gm of distilled water as described in Example 13. Benzalkonium chloride has been used in the injectable product Celestrone Soluspan.

Following the methods described in Example 13, the dispersion was homogenized, microfluidized, and analyzed under the microscope. The zeta potential for this dispersion was found to be 36 mV and thus indicated charge stability. It was run at 500 Hz for 180 seconds from four different scattering angles.

Example 16

The same methods as were used for the preceding Example were used here to prepare a similar cubic phase except 0.9520 grams of Pluronic L-122 were used in place of the 0.9501 gm of Pluronic 123. An amount of 0.9989 gm of the cubic phase were then added to 0.0638 gm of benzalkonium chloride (obtained from the Sigma Corporation) and 20.0 gm of distilled water.

Methods similar to those utilized in Example 13 were used to microfluidize, homogenize, and analyze the dispersion under the microscope. The zeta potential of the dispersion, taken at four different angles and run at 500 Hz for 180 seconds, averaged +47 mV which indicated charge stability as per the instant invention.

Example 17

This Example illustrates the method of production discussed above, in which a low-viscosity liquid phase precursor to the reversed liquid crystalline phase is prepared and dispersed, and the particles convert to the liquid crystalline phase after contact with water. An L2 phase was first prepared by mixing 2.2009 grams of propofol, 1.9883 grams of alpha-tocopherol, and 12.0964 grams of the poloxamer surfactant Ethox L-122 into a 50 mL test tube and vortexing until it was all one phase. The liquid L2 phase that formed was clear but yellow and of low viscosity. In a 150 mL beaker were placed 0.9032 grams of sodium deoxycholic acid, 2.0017 grams of glycine, 70 mL of distilled water, and 13.345 grams of the L2 phase. This was homogenized until the material was dispersed. Under observation in Differential Interference Contrast (DIC) in a Reichert-Jung Polyvar microscope, it was evident that the L2 phase had turned to a viscous and rigid cubic phase, with irregularly-shaped, angular particles in contrast with liquid droplets which are quite generally round. This was then further homogenized for 60 more minutes, and the particle size then was small enough that the material could be filtered through a 0.22 micron filter easily. The zeta potential distribution measured as described above was unimodal and centered at approximately −34 mV.

Example 18

Four reversed cubic phases were prepared with propofol (Albemarle Corporation), alpha-tocopherol (Vitamin E, from Aldrich Chemical Company), distilled water and Pluronic L122 (Ethox Corporation). The propofol and vitamin E were combined in various ratios by weight to total 19%, the water was held constant at 26% and the Pluronic L-122 at 55%. The ingredients were combined in 8 mL test tubes and thoroughly mixed until optically isotropic and of high viscosity. A total of three grams of each of the following compositions were prepared (all weights listed in grams):

|  | 10% propofol | 13% propofol | 16% propofol | 19% propofol |
| --- | --- | --- | --- | --- |
| propofol | 0.302 | 0.388 | 0.478 | 0.570 |
| vitamin E | 0.273 | 0.189 | 0.105 | 0 |
| distilled water | 0.777 | 0.792 | 0.786 | 0.784 |
| pluronic L122 | 1.657 | 1.649 | 1.658 | 1.647 |

A thin layer of each reversed cubic phase was smeared onto the inside wall of four test tubes, and an appropriate amount of solvent (either distilled water or 2.2% glycine solution—the later prepared by adding 48.9 mL of distilled water to 1.1 g of glycine, Spectrum Chemical Company) was added to each tube to obtain an overall 1% or 2% propofol concentration. Thus, the following sixteen combinations resulted:

|  | 1% overall propofol concentration | | | |
| --- | --- | --- | --- | --- |
|  | Q | glycine soln | Q | water |
| 10% propofol | 0.51 | 4.50 | 0.51 | 4.50 |
| 13% propofol | 0.41 | 4.65 | 0.41 | 4.65 |
| 16% propofol | 0.32 | 4.69 | 0.31 | 4.71 |
| 19% propofol | 0.29 | 4.72 | 0.28 | 4.73 |

|  | 2% overall propofol concentration | | | |
| --- | --- | --- | --- | --- |
|  | Q | glycine soln | Q | water |
| 10% propofol | 1.01 | 4.08 | 1.01 | 4.06 |
| 13% propofol | 0.77 | 4.32 | 0.78 | 4.28 |
| 16% propofol | 0.62 | 4.38 | 0.60 | 4.42 |
| 19% propofol | 0.53 | 4.48 | 0.55 | 4.48 |

Each tube was allowed to sit overnight at room temperature (approximately 23 degrees Celsius), during which time the reverse cubic phases surrounded by water turned opaque white, while the reverse cubic phases surrounded by glycine remained clear and transparent. Each tube was then inverted twice, and the liquid contents transferred to separate 50 mL volumetric flasks and diluted to volume with mobile phase (50% acetonitrile, 40% water, 10% methanol, 0.5% phosphoric acid, all HPLC grade solvents). The samples were mixed thoroughly and a portion of each was transferred to separate HPLC vials. A standard solution was prepared by dissolving 59.4 mg of Propofol reagent into 100 mL of mobile phase, mixing well, and transferring to vials. A check solution for the standard was prepared in the same manner, using 52.1 mg of Propofol.

The standards and samples were analyzed on a Shimadzu SCL-10A VP HPLC system with the following chromatographic conditions: 25 cm×4.6 mm Phenomenex Luna C18 column, 2.0 mL/minute isocratic flow rate, 20 uL injection volume, 14 minutes run length (propofol elution at 12 minutes), and uv detection at 270 nm.

The system proved suitable for quantification with less than 0.5% relative standard deviation of five replicate injections of the standard solution and all subsequent standard injections. Additionally, the check standard assayed at 100% of the standard solution.

The concentration of propofol in the aqueous phase was calculated with the following equation:

$$\left(\frac{sample\,peak\,area}{avg\,std\,peak\,area}\right) \times \left(\frac{conc\,of\,std\,solution\left(\frac{59.4\text{ mg}}{100\text{ mL}}\right)}{\frac{volume\,of\,aqueous\,solution}{50\text{ mL volumetric flask}}}\right) \times 100 = \frac{ug}{mL}\,propofol$$

These data were graphed as micrograms/mL propofol in the aqueous phase versus percent propofol in the cubic phase. The value for 13% propofol in the cubic phase at 1% with glycine is clearly an outlier.

| % prop in Q | 1% (gly) | 2% (gly) | 1% (water) | 2% (water) |
|---|---|---|---|---|
| 10 | 18.6 | 19.3 | 25.1 | 19.5 |
| 13 | (34.9) | 25 | 29.6 | 28.8 |
| 16 | 30.1 | 29.3 | 39.1 | 34.2 |
| 19 | 35.5 | 35.9 | 46.9 | 45.6 |

This Example thus shows that the level of aqueous propofol can be substantially reduced by the use of high partition coefficient (high-Kow) diluent as described above, as well as showing the surprising result that the use of glycine can not only reduce the level of aqueous drug, but also improve the compatibility of the reversed cubic phase with the aqueous phase, as evidenced by the clarity of the glycine samples in contrast with the non-glycine samples which showed significant turbidity in the cubic phase.

Example 19

In this Example, dogs were dosed with the formulation reported in Example 1 above, and this formulation was found to perform as well as, and similarly to, a currently marketed, emulsion-based formulation of propofol, Propoflo®. The cubic phase formulation, however, offers the advantages of being essentially free of microbial growth-supporting components.

On 3 consecutive days, six beagle dogs (approximately 1.5-3.5 years of age) were dosed with Propoflo® (a commercially available propofol formulation) and Lyotropic PF1 in a 3-way crossover design. The dogs were on a controlled feeding schedule, receiving approximately 500 grams of Certified Canine Diet (5507) for approximately 7 days prior to the initiation of dosing. Food was withheld overnight prior to each dosing session. Levels of contaminants known to be present in the feed and water were thought to be incapable of interfering with this study. Young adult used in this study were acclimated to laboratory conditions for at least 14 days prior to animal phase initiation. Six dogs were selected on the basis of general appearance and assigned to the following groups:

| Group Number | Test Article | Dose mg/kg | Dose Conc. Mg/mL | No. of Animals |
|---|---|---|---|---|
| CBG1 | Lyotropic PF1 | 6.0 | 10 | 2 |
| CBG3 | Propoflo ® | 6.0 | 10 | 2 |

The cubic phase dispersion (Lyocell®") test articles of the instant invention were stored at approximately 2-8C and protected from light. The Propoflo® was obtained from Abbott Laboratories and stored at room temperature. Body weights were obtained just prior to dose administration and were used as the basis for dosing. Clinical observations for mortality and general appearance were performed at least twice a day following dose administration. Parameters for evaluation included postdosing observations. All animals were constantly attended from the induction of anesthesia until emergence (i.e. standing on all four paws). The length of time from injection (start to finish; approximately 30 seconds) to induction, time to emergence, and time to rising to four paws was recorded for each dog. The animals were continually monitored to assess level of anesthesia using jaw tone, palpebral and toe pinch reflexes.

No mortality occurred during the dosing or post dosing periods. Relevant respiration characteristics or disturbances included the occurrence of irregular respiration, apnea, dyspnea, and mild regurgitation (in 2 dogs only). However, none of these disturbances could be considered to be test article specific since all of these occurred at an equal frequency with all three test articles. After the start of the injection, induction of anesthesia occurred within 1 minute after the start of the injection and could be described as a smooth induction regardless of test article. In most cases, dogs injected with the cubic phase preparations behaved similar (i.e., respiration characteristics, reflex events, and postdosing observations) to those injected with commercially available Propoflo® preparation.

| Individual Body Weight and dosing Records | | | | | | |
|---|---|---|---|---|---|---|
| Animal No. Prefix: CBG | USDA Number | Test Article | Body Weight (kg) | Dose (mg/kg) | Dose Concentration (mg/mL) | Dose Volume (mL) |
| | | | Day 1 | | | |
| 1M1 | 3643590 | PF1 | 19.80 | 6 | 10 | 11.9 |
| 1F2 | 4220196 | PF1 | 7.60 | 6 | 10 | 4.6 |

Individual Body Weight and dosing Records

| Animal No. Prefix: CBG | USDA Number | Test Article | Body Weight (kg) | Dose (mg/kg) | Dose Concentration (mg/mL) | Dose Volume (mL) |
|---|---|---|---|---|---|---|
| 3M5 | 3645771 | Propoflo | 12.60 | 6 | 10 | 7.6 |
| 3F6 | 4119177 | Propoflo | 10.05 | 6 | 10 | 6.1 |
| Day 2 | | | | | | |
| 2M3 | 3771687 | Propoflo | 15.25 | 6 | 10 | 9.2 |
| 2F4 | 4121538 | Propoflo | 9.10 | 6 | 10 | 5.5 |
| 3M5 | 3645771 | PF1 | 12.25 | 6 | 10 | 7.4 |
| 3F6 | 4119177 | PF1 | 10.15 | 6 | 10 | 6.1 |
| Day 3 | | | | | | |
| 1M1 | 3643590 | Propoflo | 19.85 | 6 | 10 | 12.0 |
| 1F2 | 4220196 | Propoflo | 7.55 | 6 | 10 | 4.6 |
| 2M3 | 3771687 | PF1 | 15.25 | 6 | 10 | 9.2 |
| 2F4 | 4121538 | PF1 | 9.00 | 6 | 10 | 5.4 |

Individual Predose Heart Rates

| Animal No. Prefix: CBG | USDA Number | Test Article | Heart Rate (BPM) |
|---|---|---|---|
| Day 1 | | | |
| 1M1 | 3643590 | PF1 | 90 |
| 1F2 | 4220196 | PF1 | 120 |
| 3M5 | 3645771 | Propoflo | 126 |
| 3F6 | 4119177 | Propoflo | 90 |
| Day 2 | | | |
| 1M1 | 3643590 | PF1 | 90 |
| 1F2 | 4220196 | PF1 | 120 |
| 3M5 | 3645771 | Propoflo | 120 |
| 3F6 | 4119177 | Propoflo | 90 |
| Day 3 | | | |
| 1M1 | 3643590 | Propoflo | 102 |
| 1F2 | 4220196 | Propoflo | 60 |
| 2M3 | 3771687 | PF1 | 76 |
| 2F4 | 4121538 | PF1 | 102 |

Individual Postdose Respiration Characteristics

| Animal No. Prefix: CBG | USDA Number | Test Article | Respiration Characteristics |
|---|---|---|---|
| Day 1 | | | |
| 1M1 | 3643590 | PF1 | Irregular respiration, rapid initially; then regular |
| 1F2* | 4220196 | PF1 | Period of dyspnea, irregular respiration, apnea |
| 3M5 | 3645771 | Propoflo | Regular respiration throughout episode |
| 3F6 | 4119177 | Propoflo | Regular respiration with occasional apnea |

*Regurgitation noted at approximately 2 minutes following injection

| | | | |
|---|---|---|---|
| Day 2 | | | |
| 2M3 | 3771687 | Propoflo | Regular respiration throughout episode |
| 2F4 | 4121538 | Propoflo | Initial period of apnea |
| 3M5* | 3645771 | PF1 | Irregular respiration followed by apnea. Regular respiration for remained of episode. |
| 3F6 | 4119177 | PF1 | Regular respiration throughout episode |

*Mild episode of regurgitation

| | | | |
|---|---|---|---|
| Day 3 | | | |
| 1M1 | 3643590 | Propoflo | Regular respiration throughout episode |
| 1F2 | 4220196 | Propoflo | Regular respiration throughout episode |
| 2M3 | 3771687 | PF1 | Initially, marked period of apnea followed by regular respiration |
| 2F4 | 4121538 | PF1 | Regular respiration throughout episode |

Anesthesia Log
Day 1

| Animal No. Prefix: CBG | USDA Number | Test Article | INJ to IND | IND to EMER | EMER to STER | STER to STAND |
|---|---|---|---|---|---|---|
| 1M1 | 3643590 | PF1 | 0:00:34 | 0:18:49 | 0:00:00 | 0:06:42 |
| 1F2 | 4220196 | PF1 | 0:00:41 | 0:10:27 | 0:00:00 | 0:04:26 |
| 3M5 | 3645771 | Propoflo | 0:00:40 | 0:07:33 | 0:00:16 | 0:03:31 |
| 3F6 | 4119177 | Propoflo | 0:00:29 | 0:10:29 | 0:00:10 | 0:01:23 |
| 1M1 | 3643590 | PF1 | 0:00:34 | 0:19:23 | 0:19:23 | 0:26:05 |
| 1F2 | 4220196 | PF1 | 0:00:41 | 0:11:08 | 0:11:08 | 0:15:34 |

-continued

Anesthesia Log
Day 1

| Animal No. Prefix: CBG | USDA Number | Test Article | INJ to IND | IND to EMER | EMER to STER | STER to STAND |
|---|---|---|---|---|---|---|
| 3M5 | 3645771 | Propoflo | 0:00:40 | 0:08:13 | 0:08:29 | 0:12:00 |
| 3F6 | 4119177 | Propoflo | 0:00:29 | 0:10:58 | 0:11:08 | 0:12:31 |

INJ = Injection time (start)
IND = Induction time
EMER = Emergence time
STER = Sternal posturing time
STAND = Standing time (four paws)
Format = HH:MM:SS Each test article was injected over approximately 30 seconds

Individual Anesthesia Log
Day 1

| Animal No. Prefix: CBG | USDA Number | Test Article | INJ to ABSENCE | INJ to PRESENCE | Duration |
|---|---|---|---|---|---|
| JAW TONE | | | | | |
| 1M1 | 3643590 | PF1 | 0:00:48 | 0:19:23 | 0:18:35 |
| 1F2 | 4220196 | PF1 | 0:01:48 | 0:04:53 | 0:03:05 |
| 3M5 | 3645771 | Propoflo | 0:00:55 | 0:05:57 | 0:05:02 |
| 3F6 | 4119177 | Propoflo | 0:00:52 | 0:07:14 | 0:06:22 |
| PALPEBRAL | | | | | |
| 1M1 | 3643590 | PF1 | 0:01:08 | 0:05:54 | 0:04:46 |
| 1F2 | 4220196 | PF1 | 0:01:29 | 0:04:34 | 0:03:05 |
| 3M5 | 3645771 | Propoflo | 0:01:55 | 0:03:50 | 0:01:55 |
| 3F6 | 4119177 | Propoflo | 0:01:10 | 0:05:28 | 0:04:18 |
| TOE PINCH | | | | | |
| 1M1 | 3643590 | PF1 | 0:00:57 | 0:18:59 | 0:18:02 |
| 1F2 | 4220196 | PF1 | 0:02:39 | 0:04:46 | 0:02:07 |
| 3M5 | 3645771 | Propoflo | 0:01:15 | 0:05:30 | 0:04:15 |
| 3F6 | 4119177 | Propoflo | 0:00:56 | 0:06:54 | 0:05:58 |

INJ = Injection time (start)
ABSENCE = Loss of reflex
PRESENCE = Regaining of reflex following loss
Format = HH:MM:SS Each test article was injected over approximately 30 seconds

Individual Anesthesia Log
Day 2

| Animal No. Prefix: CBG | USDA Number | Test Article | INJ to IND | IND to EMER | EMER to STER | STER to STAND |
|---|---|---|---|---|---|---|
| 2M3 | 3771687 | Propoflo | 0:00:15 | 0:09:35 | 0:02:52 | 0:2:40 |
| 2F4 | 4121538 | Propoflo | 0:00:30 | 0:05:05 | 0:00:30 | 0:01:45 |
| 3M5 | 3645771 | PF1 | 0:00:25 | 0:16:31 | 0:07:04 | 0:03:54 |
| 3F6 | 4119177 | PF1 | 0:00:20 | 0:19:47 | 0:02:47 | 0:02:20 |

| Animal No. Prefix: CBG | USDA Number | Test Article | INJ to IND | INJ to EMER | INJ to STER | INJ to STAND |
|---|---|---|---|---|---|---|
| 2M3 | 3771687 | Propoflo | 0:00:15 | 0:09:50 | 0:12:42 | 0:15:22 |
| 2F4 | 4121538 | Propoflo | 0:00:30 | 0:05:35 | 0:06:05 | 0:07:50 |

Individual Anesthesia Log
Day 2 (-continued)

| Animal No. Prefix: CBG | USDA Number | Test Article | | | |
|---|---|---|---|---|---|
| 3M5 | 3645771 | PF1 | 0:00:25 | 0:16:56 | 0:24:00 | 0:27:54 |
| 3F6 | 4119177 | PF1 | 0:00:20 | 0:20:07 | 0:22:54 | 0:25:14 |

INJ = Injection time (start)
IND = Induction time
EMER = Emergence time
STER = Sternal posturing time
STAND = Standing time (four paws)
Format = HH:MM:SS Each test article was injected over approximately 30 seconds

Individual Anesthesia Log
Day 2

| Animal No. Prefix: CBG | USDA Number | Test Article | INJ to ABSENCE | INJ to PRESENCE | Duration |
|---|---|---|---|---|---|
| JAW TONE | | | | | |
| 1M1 | 3643590 | PF1 | 0:00:57 | 0:18:59 | 0:18:02 |
| 1F2 | 4220196 | PF1 | 0:02:39 | 0:04:46 | 0:02:07 |
| 3M5 | 3645771 | Propoflo | 0:01:15 | 0:05:30 | 0:04:15 |
| 3F6 | 4119177 | Propoflo | 0:00:56 | 0:06:54 | 0:05:58 |
| PALPEBRAL | | | | | |
| 2M3 | 3771687 | Propoflo | 0:00:43 | 0:06:24 | 0:05:41 |
| 2F4 | 4121538 | Propoflo | 0:01:35 | 0:05:05 | 0:03:30 |
| 3M5 | 3645771 | PF1 | 0:01:57 | 0:09:30 | 0:07:33 |
| 3F6 | 4119177 | PF1 | 0:01:37 | 0:15:37 | 0:14:00 |

Individual Anesthesia Log
Day 2 (-continued)

| Animal No. Prefix: CBG | USDA Number | Test Article | INJ to ABSENCE | INJ to PRESENCE | Duration |
|---|---|---|---|---|---|
| TOE PINCH | | | | | |
| 2M3 | 3771687 | Propoflo | 0:00:58 | 0:06:24 | 0:05:26 |
| 2F4 | 4121538 | Propoflo | 0:00:45 | 0:05:05 | 0:04:20 |
| 3M5 | 3645771 | PF1 | 0:00:50 | 0:09:20 | 0:08:30 |
| 3F6 | 4119177 | PF1 | 0:00:40 | 0:16:00 | 0:15:20 |

INJ = Injection time (start)
ABSENCE = Loss of reflex
PRESENCE = Regaining of reflex following loss
Format = HH:MM:SS Each test article was injected over approximately 30 seconds

Individual Anesthesia Log
Day 3

| Animal No. Prefix: CBG | USDA Number | Test Article | INJ to IND | IND to EMER | EMER to STER | STER to STAND |
|---|---|---|---|---|---|---|
| 1M1 | 3643590 | Propoflo | 0:00:24 | 0:13:42 | 0:00:13 | 0:00:24 |
| 1F2 | 4220196 | Propoflo | 0:00:29 | 0:08:41 | 0:01:00 | 0:00:19 |
| 2M3 | 3771687 | PF1 | 0:00:22 | 0:16:01 | 0:06:45 | 0:00:31 |
| 2F4 | 4121538 | PF1 | 0:00:42 | 0:13:00 | 0:05:56 | 0:00:22 |
| 1M1 | 3643590 | Propoflo | 0:00:24 | 0:14:06 | 0:14:19 | 0:14:43 |
| 1F2 | 4220196 | Propoflo | 0:00:29 | 0:09:10 | 0:10:10 | 0:10:29 |
| 2M3 | 3771687 | PF1 | 0:00:22 | 0:16:23 | 0:23:08 | 0:23:39 |
| 2F4 | 4121538 | PF1 | 0:00:42 | 0:13:42 | 0:19:38 | 0:20:00 |

INJ = Injection time (start)
IND = Induction time
EMER = Emergence time
STER = Sternal posturing time
STAND = Standing time (four paws)
Format = HH:MM:SS Each test article was injected over approximately 30 seconds Individual Anesthesia Log
Day 3

| Animal No. Prefix: CBG | USDA Number | Test Article | INJ to ABSENCE | INJ to PRESENCE | Duration |
|---|---|---|---|---|---|
| JAW TONE | | | | | |
| 1M1 | 3643590 | Propoflo | 0:01:06 | 0:12:45 | 0:11:39 |
| 1F2 | 4220196 | Propoflo | 0:01:30 | 0:07:07 | 0:05:37 |
| 2M3 | 3771687 | PF1 | 0:00:44 | 0:14:15 | 0:13:31 |
| 2F4 | 4121538 | PF1 | 0:02:26 | 0:13:02 | 0:10:36 |
| PALPEBRAL | | | | | |
| 1M1 | 3643590 | Propoflo | 0:00:45 | 0:16:25 | 0:15:40 |
| 1F2 | 4220196 | Propoflo | 0:01:15 | 0:07:07 | 0:05:52 |
| 2M3 | 3771687 | PF1 | 0:00:44 | 0:13:00 | 0:12:16 |
| 2F4 | 4121538 | PF1 | 0:01:20 | 0:09:05 | 0:07:45 |
| TOE PINCH | | | | | |
| 1M1 | 3643590 | Propoflo | 0:00:53 | 0:09:54 | 0:09:01 |
| 1F2* | 4220196 | Propoflo | * | * | * |
| 2M3 | 3771687 | PF1 | 0:00:44 | 0:13:15 | 0:12:31 |
| 2F4 | 4121538 | PF1 | 0:01:18 | 0:09:50 | 0:08:32 |

*Toe Pinch reflex remained positive throughout episode
INJ = Injection time (start)
IND = Induction time
EMER = Emergence time
STER = Sternal posturing time
STAND = Standing time (four paws)
Format = HH:MM:SS Each test article was injected over approximately 30 seconds.

Example 20

A reversed cubic phase containing the anesthetic propofol was first prepared by mixing 1.496 grams of propofol (Albemarle Corporation, Baton Rouge, La. 1.346 gm of vitamin E (Aldrich Chemical Company, Milwaukee, Wis.), 3.902 gm of sterile water (Abbott Laboratories, Chicago, Ill.), and 8.255 gm of Pluronic L 122 (Ethox Chemicals, Greenville, S.C.). After thoroughly mixing this composition, it was checked that the material was optically isotropic and of high viscosity. Next, 0.504 gm of the anionic surfactant deoxycholic acid sodium salt (Aldrich Chemical Company, Milwaukee, Wis.) and 1.500 gm of glycine (Spectrum Chemical Company, Gardena, Calif.) was dissolved in 88 mL water. Then, 10.101 gm of the cubic phase was added to the 250 ml beaker containing the surfactant solution and dispersed using a homogenizer (Brinkmann Polytron PT 3000) at 29 k rpm for 20 minutes. The pH of the mixture was adjusted to 7.40 by the addition of 5 pipette droplets of 1M hydrochloric acid (Sigma Chemical Company, St. Louis, Mo.). The dispersion was injected into sterile vials using a 27 gauge needle attached to a 0.22 μm PVDF syringe filter (Millipore, Ireland). Each vial was sparged with nitrogen for 5 minutes to remove oxygen from the dispersion. Observation in a Reichert-Jung Polyvar microscope operating in differential interference contrast (DIC) mode demonstrated that a particle size on the order of 200 nanometers had been achieved. The dispersion was then analyzed using a Beckman Coulter DELSA 440SX for Doppler Electrophoretic Light Scattering Analysis, set in zeta potential measurement mode. The dispersion was diluted 4:1 water to dispersion in order to get the detector levels on scale. The resulting measured zeta potential distribution, using four angles of measurement, shows the distribution centered around −34 mV, which is a strong enough zeta potential to produce a stable dispersion. The concentration of propofol in this dispersion, referred to below as Lyotropic PF1(1%), was 1% or 10 mg/mL.

A reversed cubic phase containing the anesthetic propofol was first prepared by mixing 2.206 grams of propofol (Albemarle Corporation, Baton Rouge, La.) 1.982 gm of vitamin E (Aldrich Chemical Company, Milwaukee, Wis.), 5.739 gm of sterile water (Abbott Laboratories, Chicago, Ill.), and 12.100 gm of Pluronic L122 (Ethox Chemicals, Greenville, S.C.). After thoroughly mixing this composition, it was checked that the material was optically isotropic and of high viscosity. Next, 1.003 gm of the anionic surfactant deoxycholic acid sodium salt (Aldrich Chemical Company, Milwaukee, Wis.) and 1.502 gm of glycine (Spectrum Chemical Company, Gardena, Calif.) was dissolved in 77.5 mL water. Then, 19.989 gm of the cubic phase was added to the 250 ml beaker containing the surfactant solution and dispersed using a homogenizer (Brinkmann Polytron PT 3000) at 29 k rpm for 30 minutes. The pH of the mixture was adjusted to 7.40 by the addition of 6 pipette droplets of 1M hydrochloric acid (Sigma Chemical Company, St. Louis, Mo.). The dispersion was injected into sterile vials using a 27 gauge needle attached to a 0.22 μm PVDF syringe filter (Millipore, Ireland). Each vial was sparged with nitrogen for 5 minutes to remove oxygen from the dispersion. Observation in a Reichert-Jung Polyvar microscope operating in differential interference contrast (DIC) mode demonstrated that a particle size on the order of 200 nanometers had been achieved. The dispersion was then analyzed using a Beckman Coulter DELSA 440SX for Doppler Electrophoretic Light Scattering Analysis, set in zeta potential measurement mode. The dispersion was diluted 4:1 water to dispersion in order to get the detector levels on scale. The resulting measured zeta potential distribution, using four angles of measurement, shows the distribution centered around −32 mV, which is a strong enough zeta potential to produce a stable dispersion. The concentration of propofol in this dispersion, referred to below as Lyotropic PF1(2%), was 2% or 20 mg/mL.

Dogs were dosed with the above two formulations, and each was found to perform as well as or better than, and similarly to, a currently marketed, emulsion-based formulation of propofol, Propoflo® (Abbot Labs).

On 3 consecutive days, six beagle dogs (approximately 1.5-3.5 years of age) were dosed with either Propoflo® (a commercially available propofol formulation) or Lyotropic PF1(1%) or Lyotropic PF1(2%) in a 3-way randomized crossover design. The dogs were on a controlled feeding schedule, receiving approximately 500 grams of Certified Canine Diet (5507) for approximately 7 days prior to the initiation of dosing. Food was withheld overnight prior to each dosing session. Levels of contaminants known to be present in the feed and water were thought to be incapable of interfering with this study. The animals used in this study were acclimated to laboratory conditions for at least 14 days prior to animal phase initiation. Six dogs (3 male and 3 female) were selected on the basis of general appearance.

The cubic phase dispersion ("LyoCell®") test articles of the instant invention were stored at approximately 2-8° C. and protected from light. The Propoflo® was obtained from Abbott Laboratories and stored at room temperature. Body weights were obtained just prior to dose administration and were used as the basis for dosing, and all dogs were dosed at 6.0 mg/mL for each of the three formulations. Clinical observations for mortality and general appearance were performed at least twice a day following dose administration. Parameters for evaluation included post dosing observations. All animals were constantly attended from the induction of anesthesia until emergence (i.e. standing on all four paws). The length of time from injection (start to finish; approximately 30 seconds) to induction, emergence, sternal posturing and rising to four paws was recorded for each dog. The animals were continually monitored to assess level of anesthesia using jaw tone, palpebral and toe pinch reflexes. No mortality occurred during the dosing or post dosing periods. Relevant respiration characteristics or disturbances included the occurrence of irregular respiration, apnea, dyspnea, and mild regurgitation (in 1 dog only). Induction of anesthesia occurred within 1 minute after the start of the injection and could be described as a smooth induction regardless of test article. In most cases, dogs injected with the cubic phase preparations behaved similar (i.e., respiration characteristics, reflex events, and post dosing observations) to those injected with commercially available Propoflo®.

| Individual Post dose respiration characteristics | | | | |
|---|---|---|---|---|
| Day | USDA Number | Test Article | Pre-Dose Heart Rate (bpm) | Respiration Characteristics |
| 1 | 4365500 | PF1 (1%) | 90 | Initial period of rapid shallow breathing; then regular breathing pattern |
| 1 | 4175654 | PF1 (1%) | 96 | Regular breathing pattern |
| 1 | 4169859 | PF1 (2%) | 108 | Regular breathing pattern. Regurgitation at 30 sec post dose, at 35 min 45 sec post dose, and 1:17:00 post dose |
| 1 | 4372646 | PF1 (2%) | 72 | Initial period of apnea, then regular breathing pattern |
| 2 | 4365500 | Propoflo ® | 90 | Regular breathing pattern |
| 2 | 4175654 | Propoflo ® | 96 | Regular breathing pattern |
| 2 | 4169859 | PF1 (1%) | 102 | Initial period of rapid shallow breathing; then regular breathing pattern |
| 2 | 4372646 | PF1 (1%) | 66 | Initial period of rapid shallow breathing; then regular breathing pattern |
| 2 | 4361270 | PF1 (2%) | 96 | Initial period of rapid shallow breathing; then regular breathing pattern |
| 2 | 4360206 | PF1 (2%) | 78 | Initial period of rapid shallow breathing; then regular breathing pattern |
| 3 | 4365500 | PF1 (2%) | 102 | Initial period of apnea, then regular breathing pattern |
| 3 | 4175654 | PF1 (2%) | 78 | Initial period of rapid shallow breathing; then regular breathing pattern |
| 3 | 4169859 | Propoflo ® | 90 | Regular breathing pattern |
| 3 | 4372646 | Propoflo ® | 72 | Regular breathing pattern |
| 3 | 4361270 | PF1 (1%) | 66 | Initial period of apnea, then rapid shallow breathing, then regular breathing pattern |
| 3 | 4360206 | PF1 (1%) | 84 | Regular breathing pattern |
| 4 | 4361270 | Propoflo ® | 78 | Regular breathing pattern |
| 4 | 4360206 | Propoflo ® | 72 | Regular breathing pattern |

| Anesthesia Log | | | | |
|---|---|---|---|---|
| Animal Number | USDA Number | Test Article | INJ to IND | INJ to EMER |
| | | Propoflo ® | | |
| 1M1 | 4365500 | Propoflo ® | 0:00:33 | 0:08:09 |
| 1F4 | 4175654 | Propoflo ® | 0:00:25 | 0:06:58 |
| 2M2 | 4169859 | Propoflo ® | 0:00:32 | 0:20:49 |
| 2F5 | 4372646 | Propoflo ® | 0:00:24 | 0:15:43 |
| 3M3 | 4361270 | Propoflo ® | 0:00:25 | 0:13:22 |
| 3F6 | 4360206 | Propoflo ® | 0:00:24 | 0:08:05 |
| | | AVERAGE | 0:00:27 | 0:12:11 |
| | | STD DEV | 0:00:04 | 0:05:27 |
| | | PF1 (1%) | | |
| 1M1 | 4365500 | PF1 (1%) | 0:00:33 | 0:22:30 |
| 1F4 | 4175654 | PF1 (1%) | 0:00:30 | 0:19:01 |
| 2M2 | 4169859 | PF1 (1%) | 0:00:30 | 0:17:00 |
| 2F5 | 4372646 | PF1 (1%) | 0:00:27 | 0:18:01 |
| 3M3 | 4361270 | PF1 (1%) | 0:00:25 | 0:19:23 |
| 3F6 | 4360206 | PF1 (1%) | 0:00:37 | 0:18:38 |
| | | AVERAGE | 0:00:30 | 0:19:05 |
| | | STD DEV | 0:00:04 | 0:01:52 |
| | | PF1 (2%) | | |
| 2M2 | 4169859 | PF1 (2%) | 0:00:44 | 0:34:19 |
| 2F5 | 4372646 | PF1 (2%) | 0:00:26 | 0:33:50 |

-continued

| | | Individual Post dose respiration characteristics | | |
|---|---|---|---|---|
| 3M3 | 4361270 | PF1 (2%) | 0:00:40 | 0:20:39 |
| 3F6 | 4360206 | PF1 (2%) | 0:00:35 | 0:29:12 |
| 1M1 | 4365500 | PF1 (2%) | 0:00:34 | 0:09:22 |
| 1F4 | 4175654 | PF1 (2%) | 0:00:26 | 0:17:06 |
| | | AVERAGE | 0:00:34 | 0:24:05 |
| | | STD DEV | 0:00:07 | 0:10:02 |

| | Summary of Anesthesia Log | | |
|---|---|---|---|
| | Propoflo ® | PF1 (1%) | PF1 (2%) |
| INJ to IND | 0:00:27 | 0:00:30 | 0:00:34 |
| INJ to EMER | 0:12:11 | 0:19:05 | 0:24:05 |

INJ = Injection time (start)
IND = Induction time
EMER = Emergence time
Format = HH:MM:SS Each test article was injected over approximately 30 seconds

Example 21

The following example describes a charge-stabilize liquid crystalline dispersion containing the local anesthetic drug bupivacaine. Working in a laminar flow hood, 0.900 grams of the local anesthetic bupivacaine, in its free base form, were dissolved in 3.64 gm of alpha-tocopherol (Aldrich Chemical Company, Milwaukee, Wis.) by heating to 55° C. Following dissolution, 1.820 gm of sterile water (Abbott Laboratories, Chicago, Ill.) and 3.640 gm of Pluronic P123 (BASF Corporation, Mt. Olive, N.J.) was added to the vitamin E. The components were mixed to form a reversed cubic phase that was optically isotropic and of high viscosity. Next, 0.402 gm of sodium deoxycholate (Aldrich Chemical Company, Milwaukee, Wis.) was dissolved in 39.6 ml of sterile water. An amount 8.048 gm of cubic phase was dispersed in the sodium deoxycholate solution, first using the homogenizer (Brinkmann Polytron PT 3000) at 29 k rpm for 1 minute, then using the microfluidizer (Micofluidics Model M110L) at approximately 15,000 psi for five 1.5 minute runs. The dispersion, referred to as "Lyotropic/F4C," was injected into sterile vials using a 27 gauge needle attached to a 0.45 μm PVDF syringe filter (Millipore, Ireland).

Figure 15:
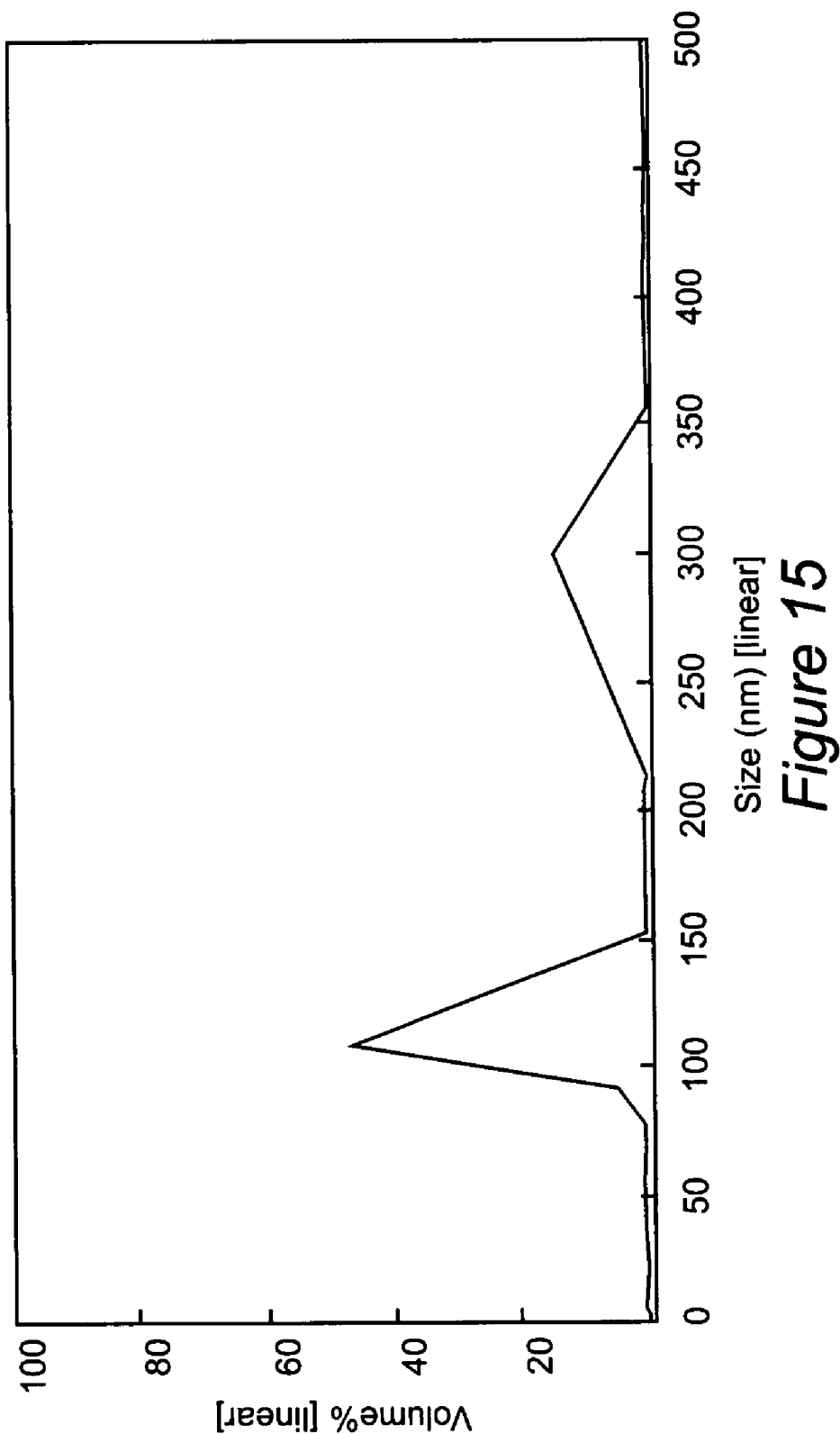
FIG. 15 shows the particle size data for the dispersion described in Example 21.
Figure 16:
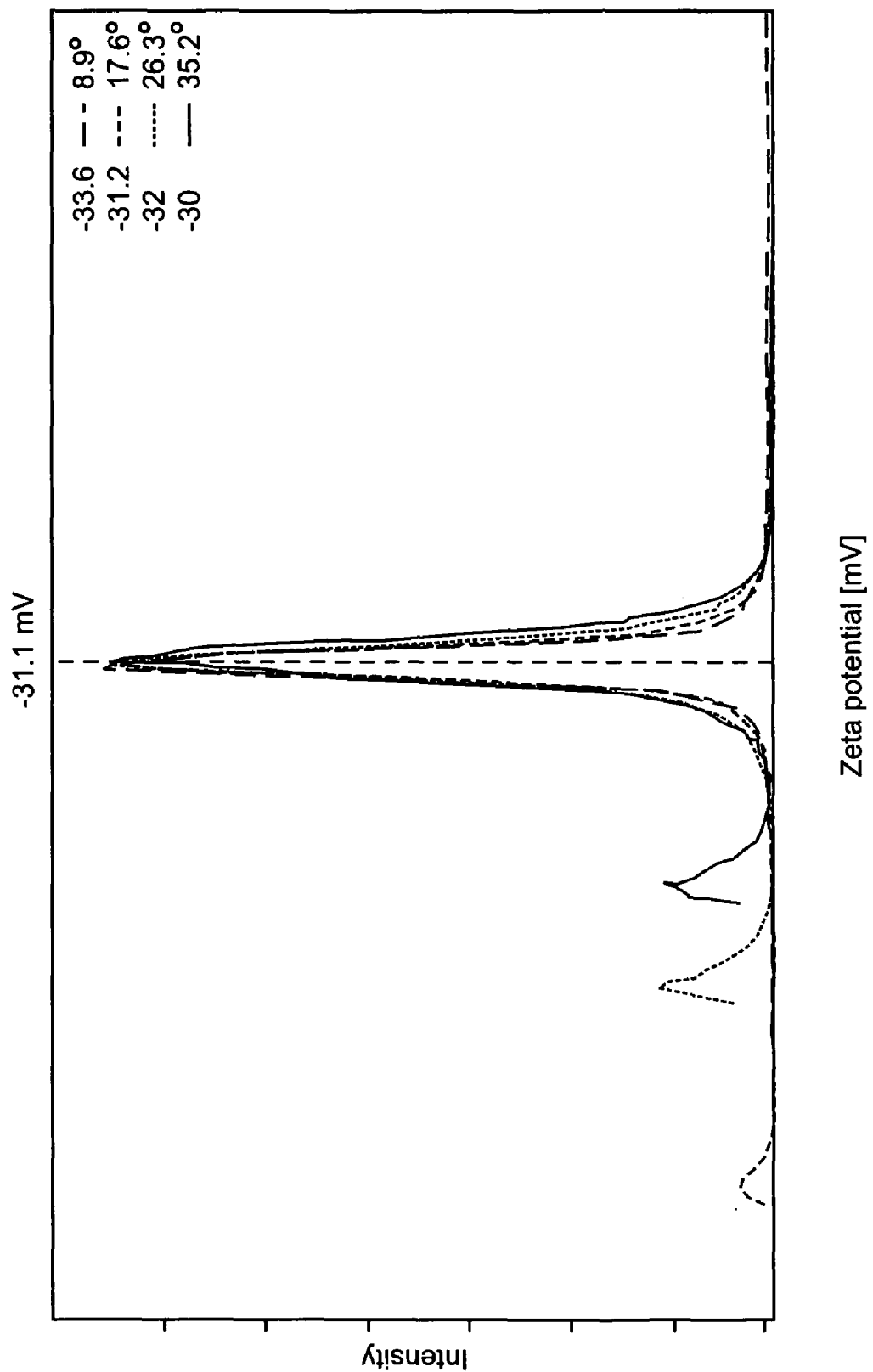
FIG. 16 shows the zeta potential data for the dispersion described in Example 21.

Lyotropic/F4C was analyzed using a Beckman Coulter N4 PLUS submicron particle size analyzer. A drop of the dispersion was diluted in water until an adequate measurement intensity level was obtained. FIG. 15 illustrates the results of a particle size analysis with a five minute equilibration time and a three minute run time. All of the particles in the dispersion are less than 400 nm. Additionally, Lyotropic/F4C was analyzed using a Beckman Coulter DELSA 440SX for Doppler Electrophoretic Light Scattering Analysis, set in zeta potential measurement mode. FIG. 16 shows the measured zeta potential distribution, using four angles of measurement. At all four angles, the distribution is centered at −31 mV, which is a strong enough zeta potential to produce a stable dispersion.

The above formulation was tested in the rat "Paw Withdrawal" model to determine the duration of analgesia. Male Sprague-Dawley rats, weighing 400-450 gm, were studied at two dose levels: 1.0 mg/kg and 3.0 mg/kg. All rats were housed under standard conditions in accordance to AALAC guidelines, with access to food and water ad libitum. Six hours prior to evaluation, food was withheld.

PROCEDURES: Each rat was briefly anesthetized by exposure to the inhalational agent halothane in order to facilitate animal handling and to ensure precise injection of the test and control agents. Once unconscious, a small incision in the region of the popliteal fossa of the hind limb was made. Exposure of the sciatic nerve was obtained with minimal retraction. Utilizing an appropriately sized needle and syringe, either the bupivacaine-LyoCell® formulation or the standard bupivacaine hydrochloride was injected into the perineurium of the sciatic nerve. The incision was then closed with an appropriately sized surgical clip.

Local anesthetic blockade to thermal nociception was determined by exposure of the hind paw of the treated hind limb to the heated surface of a thermal plantar testing apparatus. Surface temperatures were maintained in a range from 50 to 54 degree C. The latency period to pay withdrawal from the heated surface was recorded by digital timer. Baseline latency period was found to be approximately 1 to 3 seconds in non-anesthetized hind paws. In an attempt to minimize thermal injury to the hind paw, maximum exposure to the thermal plantar testing apparatus was limited to 12 seconds. Latency periods exceeding 6 seconds were considered indicative of analgesia to thermal testing.

Six rats were tested for latency withdrawal of the treated hind limb after 30 minutes and 60 minutes, and then hourly for an additional five hours. At a dose of 1 mg/kg dose of the cubic phase formulation, the sensor blocking effect lasted over 5 hours, for 4 of the 6 rats tested and over 6 hours for two of the six rats tested.

Example 22

This Example demonstrates the long-term physical stability of dispersions of the instant invention. A cubic phase was first prepared by mixing 5.7176 grams of propofol, 7.8170 grams of water, and 16.5300 grams of the poloxamer surfactant Ethox L-122 into a 50 mL test tube and stirring with a spatula until it was all one phase. In a 600 mL beaker were placed 1.0533 grams of sodium deoxycholic acid, 400 mL of distilled water, and 21.0682 grams of the cubic phase. This was homogenized with a Brinkmann PT 10/35 homogenizer until the material was dispersed. This was then microfluidized using a Microfluidics M110L for 10 runs of 1.5 minutes each run. The dispersion was then injected into sterile vials via an 18 gauge needle.

Analysis of the pH, particle size (measured as described herein by a Beckmann N4 Plus particle sizer), and zeta potential (as described, with a DELSA analyzer) was performed at regular intervals over a period of six months. The 6-month data, reported in the table below, indicate excellent stability for the particle dispersion.

| Test | Day 0 | 6 Months |
|---|---|---|
| pH | 8.1 | 7.9 |
| Particle Size | 132 nm | 135 nm |
| Zeta Potential | −48 mV | −34 mV |

Example 23

A reversed cubic phase containing the anesthetic etomidate was prepared by dissolving 0.0200 grams of etomidate (Sigma Chemical Company, St. Louis, Mo.) in 0.300 gm of vitamin E (Aldrich Chemical Company, Milwaukee, Wis.) and adding 0.190 gm of distilled water and 0.488 gm of Pluronic L122 (Ethox Chemicals, Greenville, S.C.). After thoroughly mixing this composition, it was checked that the material was optically isotropic and of high viscosity. Next, 0.024 gm of the anionic surfactant docusate sodium (Aldrich Chemical Company, Milwaukee, Wis.) was dissolved in 5.992 gm of distilled water. Then, 0.605 gm of the cubic phase was added to the 50 mL beaker containing the surfactant solution and dispersed using a homogenizer (Brinkmann PT 10/35) at speed 10 for 10 minutes. The dispersion was injected into a sterile vial using a 27 gauge needle attached to a 0.20 µm PTFE syringe filter (Millipore, Ireland). Observation in a Reichert-Jung Polyvar microscope operating in differential interference contrast (DIC) mode demonstrated that a particle size on the order of 200 nanometers had been achieved. The dispersion was then analyzed using a Beckman Coulter DELSA 440SX for Doppler Electrophoretic Light Scattering Analysis, set in zeta potential measurement mode. The resulting measured zeta potential distribution, using four angles of measurement, shows the distribution centered on −48.5 mV, which is a strong enough zeta potential to produce a stable dispersion. The concentration of etomidate in this dispersion was 0.2% or 2 mg/mL.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A pharmaceutical composition, comprising:
   a plurality of uncoated, ionically charged particles of a single thermodynamic equilibrium reversed cubic phase material, wherein said single thermodynamic equilibrium reversed cubic phase material has an anionic charge; and
   a liquid comprising a polar solvent, said uncoated, ionically charged particles being stabilized in dispersion in said liquid due to a particle zeta potential created by said anionic charge, wherein said uncoated, ionically charged particles have a size of from 10 nm to 100 microns.

2. The composition of claim 1 wherein said particle zeta potential has a magnitude greater than 25 millivolts.

3. The composition of claim 1 wherein said single thermodynamic equilibrium reversed cubic phase material includes or has associated therewith at least one active pharmaceutical ingredient dissolved therein and at least one bilayer-associated second ingredient dissolved therein, and wherein at least one of said active pharmaceutical ingredient and said second ingredient has an anionic charge.

4. The composition of claim 1 wherein said anionic charge of said particle is due to the presence of at least one charged, bilayer-associated ingredient and wherein the weight ratio of the total of all the charged, bilayer-associated ingredients to the single thermodynamic equilibrium reversed cubic phase material is between 0.01:1 and 0.15:1.

5. The composition of claim 1 wherein said composition is pharmaceutically acceptable for injection in a human or animal.

6. The composition of claim 1 wherein said single thermodynamic equilibrium reversed cubic phase material is formed from at least one active ingredient dissolved therein and at least one second ingredient dissolved therein, wherein at least one of said at least one active ingredient and said at least one second ingredient has said anionic charge.

7. The composition of claim 4 wherein said charged, bilayer-associated ingredient is selected from the group consisting of albumin, casein, stearylamine, tocopherol succinate, salt of 2-ethylhexanoic acid, salt of riboflavin, salt of riboflavin phosphate, salt of oligolactic acid, sodium dodecylsulfate, benzethonium chloride, salt of gentisic acid, salt of N-acetyltryptophan, salt of tryptophan, salt of tyrosine, salt of phenylalanine, aspartic acid, cystine, salt of oxyquinoline, salt of docusate, salt of a lactic acid-glycol acid oligomer, stearic acid and other 18-carbon fatty acids including oleic, linoleic, and linolenic acids, myristyl gamma-picolinium chloride, phosphatidylserine, phosphatidylinositol, phosphatidylglycerol, benzalkonium chloride, tocopheryl dimethylaminoacetate hydrochloride, CYTOFECTIN GS™ (dioleoylphosphatidylethanolamine, CAS#2462-63-7 and dimyristylamidoglycyl-N-α-isopropoxycarbonyl-arginine dihydrochloride), 1,2-dioleoyl-sn-glycero-3-trimethylammonium-propane, dimethyldioctadecyl ammonium bromide, trimethyl aminoethane carbamoyl cholesterol iodide, O,O'-ditetradecanoyl-N-(alpha-trimethyl ammonioacetyl)diethanolamine chloride, N-[(1-(2,3-dioleyloxy)propyl)]-N—N—N-trimethylammonium chloride, N-methyl-4-(dioleyl)methylpyridinium chloride, 1,2-dimyristyloxypropyl-3-dimethylhydroxyethyl ammonium bromide, bis[2-(11-phenoxyundecanoate)ethyl]-dimethylammonium bromide, N-hexadecyl-N-10-[O-(4-acetoxy)-phenylundecanoate] ethyl-dimethylammonium bromide, 3-beta-[N—(N',N'-dimethylaminoethane)carbamoyl, salt of deoxycholic acid and related cholates including glycocholate.

8. The composition of claim 3 wherein said active pharmaceutical ingredient is a pharmaceutical compound selected from the group consisting of general anesthetics, local anesthetics, anticancer compounds, muscle relaxants, hypnotics, sedatives, analgesics, antipyretics, anti-inflammatories, steroids, steroidal anti-inflammatories, opiates, cannabinoids, proteins, and antibiotics including antifungals and antimicrobials.

9. The composition of claim 3 wherein said active pharmaceutical ingredient is a general anesthetic that is selected from the group consisting of propofol, eugenol, alphaxalone, alphadalone, alphadolone, eltanolone, propanidid, ketamine, etomidate, and pregnanolone.

10. The composition of claim 1 wherein said single thermodynamic equilibrium reversed cubic phase material includes a surfactant and wherein said surfactant is selected from the group consisting of phosphatidylcholine, phosphatidylethanolamine, ARLATONE® G (polyoxyethylene hydrogenated castor oil or polyoxyethylene fatty glyceride, CAS#61788-85-0), TWEEN™ 85 (polyoxyethylenesorbitan trioleate, CAS#900506506), glycerol monooleate, long-chain unsaturated monoglycerides, sorbitan monooleate, zinc docusate, calcium docusate, and poloxamers with less than about 30% polyethylene glycol (PEG) groups by weight.

11. A material, which, when combined with a medium, forms a plurality of uncoated particles each with an anionic charge and comprising a single thermodynamic equilibrium reversed cubic phase material with an active dissolved therein, and wherein said uncoated particles with an anionic charge are stable in dispersion in said medium due to a particle zeta potential created by said anionic charge, wherein said uncoated, ionically charged particles have a size of from 10 nm to 100 microns.

12. The composition of claim 1 wherein said single thermodynamic equilibrium reversed cubic phase material includes a phospholipid.

13. The composition of claim 3 wherein said active pharmaceutical ingredient is etomidate.

14. The composition of claim 1 wherein said single thermodynamic equilibrium reversed cubic phase material includes a polaxamer.

15. The composition of claim 1 wherein said particle zeta potential has a magnitude greater than or equal to 30 millivolts.

16. The composition of claim 1 wherein said particle zeta potential has a magnitude greater than or equal to 45 millivolts.

17. The composition of claim 1 wherein said particle zeta potential has a magnitude greater than or equal to 55 millivolts.

18. The composition of claim 1 further comprising a targeting moiety associated with said particles.

19. The composition of claim 1 wherein said composition is pharmaceutically acceptable for topical, buccal, oral, sublingual or inhalation administration in a human or animal.

20. The composition of claim 3 wherein the active pharmaceutical ingredient is a component of said single thermodynamic equilibrium reversed cubic phase material.

21. The composition of claim 3 wherein the active pharmaceutical ingredient is preferentially located in the bilayer of the single thermodynamic equilibrium reversed cubic phase material.

22. The material of claim 11 further comprising a targeting moiety.

23. The material of claim 11 wherein said material is pharmaceutically acceptable for topical, buccal, oral, sublingual or inhalation administration in a human or animal.

24. The material of claim 11 wherein the active is etomidate.

25. The material of claim 11 wherein the active preferentially locates in the bilayer of single thermodynamic equilibrium reversed cubic phase material.

26. The composition of claim 11 wherein said particle zeta potential has a magnitude greater than or equal to 30 millivolts.

27. The composition of claim 11 wherein said particle zeta potential has a magnitude greater than or equal to 45 millivolts.

28. The composition of claim 11 wherein said particle zeta potential has a magnitude greater than or equal to 55 millivolts.

29. The material of claim 11 wherein said material is pharmaceutically acceptable for injection in a human or animal.

* * * * *